United States Patent
Tyler et al.

(10) Patent No.: US 12,144,987 B2
(45) Date of Patent: Nov. 19, 2024

(54) METHODS AND APPARATUSES FOR TRANSDERMAL STIMULATION OF THE OUTER EAR

(71) Applicant: IST, LLC, Dover, DE (US)

(72) Inventors: William J. Tyler, Cave Creek, AZ (US); Wing Law, Cupertino, CA (US); Douglas Jeffery, San Jose, CA (US); Rafal Piersiak, Los Gatos, CA (US)

(73) Assignee: IST, LLC, Dover, DE (US)

( * ) Notice: Subject to any disclaimer, the term of this patent is extended or adjusted under 35 U.S.C. 154(b) by 0 days.

(21) Appl. No.: 18/146,021

(22) Filed: Dec. 23, 2022

(65) Prior Publication Data
US 2023/0125579 A1    Apr. 27, 2023

Related U.S. Application Data

(63) Continuation of application No. 16/588,925, filed on Sep. 30, 2019, now Pat. No. 11,534,608, which is a
(Continued)

(51) Int. Cl.
*A61N 1/36* (2006.01)
*A61M 21/02* (2006.01)
(Continued)

(52) U.S. Cl.
CPC ......... *A61N 1/36025* (2013.01); *A61M 21/02* (2013.01); *A61N 1/0408* (2013.01);
(Continued)

(58) Field of Classification Search
CPC ............ A61N 1/36025; A61N 1/36034; A61N 1/36036; A61N 1/0476; A61M 21/02
See application file for complete search history.

(56) References Cited

U.S. PATENT DOCUMENTS

| | | |
|---|---|---|
| 3,255,753 A | 6/1966 | Wing |
| 3,388,699 A | 1/1968 | Webb et al. |
| (Continued) | | |

FOREIGN PATENT DOCUMENTS

| | | |
|---|---|---|
| CN | 1204268 A | 1/1999 |
| CN | 1607970 A | 4/2005 |
| (Continued) | | |

OTHER PUBLICATIONS

Adelman et al.; Relation between body structure and hearing during soft tissue auditory stimulation; BioMed Research International; vol. 2015; 6 pages; (http://dx.doi.org/10.1155/2015/172026; Apr. 16, 2015.
(Continued)

*Primary Examiner* — Catherine M Voorhees
(74) *Attorney, Agent, or Firm* — Shay Glenn LLP

(57) ABSTRACT

Transdermal electrical stimulation (TES) applicators that are wearable and configured to attached to a subject's pinna (ear) and adapted to apply TES to modulate the subject's cognitive and/or physiological state. These apparatuses may be configured so that they can be worn against the ear (e.g., the cymba of the ear) to deliver TES. Also described herein are methods of using them to modulate a subject's cognitive state. These TES applicators may also be adapted to function as audio headphones for concurrent delivery of TES and audible signals (e.g., music).

19 Claims, 27 Drawing Sheets

Related U.S. Application Data continuation-in-part of application No. 15/536,148, filed as application No. PCT/US2016/012054 on Jan. 4, 2016, now Pat. No. 10,426,945.

(60) Provisional application No. 62/099,547, filed on Jan. 4, 2015, provisional application No. 62/168,598, filed on May 29, 2015, provisional application No. 62/190,205, filed on Jul. 8, 2015, provisional application No. 62/200,250, filed on Aug. 3, 2015, provisional application No. 62/168,615, filed on May 29, 2015, provisional application No. 62/200,256, filed on Aug. 3, 2015.

(51) Int. Cl.
*A61N 1/04* (2006.01)
*A61M 21/00* (2006.01)

(52) U.S. Cl.
CPC ..... *A61N 1/36034* (2017.08); *A61N 1/36036* (2017.08); *A61M 2021/0072* (2013.01); *A61M 2210/0662* (2013.01); *A61N 1/0476* (2013.01)

(56) References Cited

U.S. PATENT DOCUMENTS

| | | | |
|---|---|---|---|
| 3,620,219 | A | 11/1971 | Barker |
| 3,648,708 | A | 3/1972 | Haeri |
| 3,762,396 | A | 10/1973 | Ballentine et al. |
| 4,418,687 | A | 12/1983 | Matsumoto et al. |
| 4,431,000 | A | 2/1984 | Butler et al. |
| 4,646,744 | A | 3/1987 | Capel |
| 4,664,117 | A | 5/1987 | Beck |
| 4,865,048 | A | 9/1989 | Eckerson |
| 5,144,952 | A | 9/1992 | Frachet et al. |
| 5,183,041 | A | 2/1993 | Toriu et al. |
| 5,335,657 | A | 8/1994 | Terry et al. |
| 5,342,410 | A | 8/1994 | Braverman |
| 5,397,338 | A | 3/1995 | Grey et al. |
| 5,476,481 | A | 12/1995 | Schondorf |
| 5,487,759 | A | 1/1996 | Bastyr et al. |
| 5,514,175 | A | 5/1996 | Kim et al. |
| 5,540,736 | A | 7/1996 | Haimovich et al. |
| 5,573,552 | A | 11/1996 | Hansjurgens |
| 5,578,065 | A | 11/1996 | Hattori et al. |
| 5,593,427 | A | 1/1997 | Gliner et al. |
| 5,738,647 | A | 4/1998 | Bernhard et al. |
| 5,792,067 | A | 8/1998 | Karell |
| 6,066,163 | A | 5/2000 | John |
| 6,280,454 | B1 | 8/2001 | Wang |
| 6,324,432 | B1 | 11/2001 | Rigaux et al. |
| 6,445,955 | B1 | 9/2002 | Michelson et al. |
| 6,463,328 | B1 | 10/2002 | John |
| 6,516,227 | B1 | 2/2003 | Meadows et al. |
| 6,526,318 | B1 | 2/2003 | Ansarinia |
| 6,567,702 | B1 | 5/2003 | Nekhendzy et al. |
| 6,731,987 | B1 | 5/2004 | McAdams et al. |
| 6,983,184 | B2 | 1/2006 | Price |
| 7,120,499 | B2 | 10/2006 | Thrope et al. |
| 7,146,217 | B2 | 12/2006 | Firlik et al. |
| 7,263,501 | B2 | 8/2007 | Tirinato et al. |
| 7,315,761 | B2 | 1/2008 | De Ridder |
| 7,376,467 | B2 | 5/2008 | Thrope et al. |
| 7,422,555 | B2 | 9/2008 | Zabara |
| 7,577,481 | B2 | 8/2009 | Firlik et al. |
| 7,613,519 | B2 | 11/2009 | De Ridder |
| 7,660,636 | B2 | 2/2010 | Castel et al. |
| 7,801,600 | B1 | 9/2010 | Carbunaru et al. |
| 7,891,615 | B2 | 2/2011 | Bevirt |
| 7,949,403 | B2 | 5/2011 | Palermo et al. |
| 8,029,431 | B2 | 10/2011 | Tononi |
| 8,034,294 | B1 | 10/2011 | Goldberg |
| 8,086,318 | B2 | 12/2011 | Strother et al. |
| 8,097,926 | B2 | 1/2012 | De Graff et al. |
| 8,116,875 | B2 | 2/2012 | Osypka et al. |
| 8,121,695 | B2 | 2/2012 | Gliner et al. |
| 8,150,537 | B2 | 4/2012 | Tanaka et al. |
| 8,190,248 | B2 | 5/2012 | Besio et al. |
| 8,197,276 | B2 | 6/2012 | Egloff et al. |
| 8,204,601 | B2 | 6/2012 | Moyer et al. |
| 8,239,030 | B1 | 8/2012 | Hagedorn et al. |
| 8,265,761 | B2 | 9/2012 | Siever |
| 8,280,502 | B2 | 10/2012 | Hargrove et al. |
| 8,346,337 | B2 | 1/2013 | Heller et al. |
| 8,380,315 | B2 | 2/2013 | DeGiorgio et al. |
| 8,428,738 | B2 | 4/2013 | Valencia |
| 8,460,356 | B2 | 6/2013 | Rogers et al. |
| 8,463,383 | B2 | 6/2013 | Sakai et al. |
| 8,494,625 | B2 | 7/2013 | Hargrove |
| 8,494,627 | B2 | 7/2013 | Bikson et al. |
| 8,506,469 | B2 | 8/2013 | Dietrich et al. |
| 8,532,758 | B2 | 9/2013 | Silverstone |
| 8,560,075 | B2 | 10/2013 | Covalin |
| 8,571,651 | B2 | 10/2013 | Ben-Ezra et al. |
| 8,583,238 | B1 | 11/2013 | Heldman et al. |
| 8,583,256 | B2 | 11/2013 | Tracey et al. |
| 8,612,005 | B2 | 12/2013 | Rezai et al. |
| 8,639,343 | B2 | 1/2014 | De Vos |
| 8,660,644 | B2 | 2/2014 | Jaax et al. |
| 8,688,239 | B2 | 4/2014 | Hartlep et al. |
| 8,843,210 | B2 | 9/2014 | Simon et al. |
| 8,874,219 | B2 | 10/2014 | Trier et al. |
| 8,903,494 | B2 | 12/2014 | Goldwasser et al. |
| 8,983,621 | B2 | 3/2015 | Hou et al. |
| 9,002,458 | B2 | 4/2015 | Pal et al. |
| 9,014,811 | B2 | 4/2015 | Pal et al. |
| 9,067,054 | B2 | 6/2015 | Simon et al. |
| 9,168,374 | B2 | 10/2015 | Su |
| 9,205,258 | B2 | 12/2015 | Simon et al. |
| 9,233,244 | B2 | 1/2016 | Pal et al. |
| 9,248,292 | B2 | 2/2016 | Trier et al. |
| 9,333,334 | B2 | 5/2016 | Jeffery et al. |
| 9,364,674 | B2 | 6/2016 | Cook et al. |
| 9,393,401 | B2 | 7/2016 | Goldwasser et al. |
| 9,393,430 | B2 | 7/2016 | Demers et al. |
| 9,399,126 | B2 | 7/2016 | Pal et al. |
| 9,415,219 | B2 | 8/2016 | Simon et al. |
| 9,440,070 | B2 | 9/2016 | Goldwasser et al. |
| 9,446,242 | B2 | 9/2016 | Griffith |
| 9,474,891 | B2 | 10/2016 | Demers et al. |
| 9,474,905 | B2 | 10/2016 | Doan et al. |
| 9,517,351 | B2 | 12/2016 | Charlesworth et al. |
| 9,655,772 | B2 | 5/2017 | Smith et al. |
| 9,656,076 | B2 | 5/2017 | Trier et al. |
| 9,700,725 | B2 | 7/2017 | Zhu |
| 9,731,116 | B2 | 8/2017 | Chen |
| 9,744,347 | B2 | 8/2017 | Chen et al. |
| 9,764,133 | B2 | 9/2017 | Thomas et al. |
| 9,782,587 | B2 | 10/2017 | Trier et al. |
| 9,956,405 | B2 | 5/2018 | Goldwasser et al. |
| 9,968,780 | B2 | 5/2018 | Pal et al. |
| 10,258,788 | B2 | 4/2019 | Jeffery |
| 10,293,161 | B2 | 5/2019 | Charlesworth et al. |
| 10,426,945 | B2 * | 10/2019 | Tyler ................ G10L 15/02 |
| 10,485,972 | B2 | 11/2019 | Pal et al. |
| 10,537,703 | B2 | 1/2020 | Tyler et al. |
| 10,556,108 | B1 | 2/2020 | Katsnelson et al. |
| 10,589,105 | B2 * | 3/2020 | Hyde ................ A61H 23/0245 |
| 11,534,608 | B2 * | 12/2022 | Tyler ................ A61N 1/36025 |
| 2001/0000187 | A1 | 4/2001 | Peckham et al. |
| 2002/0116036 | A1 | 8/2002 | Daignault et al. |
| 2003/0088279 | A1 | 5/2003 | Rissmann et al. |
| 2003/0134545 | A1 | 7/2003 | McAdams et al. |
| 2003/0171685 | A1 | 9/2003 | Lesser et al. |
| 2003/0225323 | A1 | 12/2003 | Kiani et al. |
| 2004/0019370 | A1 | 1/2004 | Gliner et al. |
| 2004/0098065 | A1 | 5/2004 | Hagglof et al. |
| 2004/0158305 | A1 | 8/2004 | Axelgaard |
| 2004/0267333 | A1 * | 12/2004 | Kronberg ........... A61N 1/36021 607/72 |
| 2005/0085751 | A1 | 4/2005 | Daskal et al. |
| 2005/0165460 | A1 * | 7/2005 | Erfan ................ A61N 1/0472 607/57 |

(56) References Cited

U.S. PATENT DOCUMENTS

| | | |
|---|---|---|
| 2005/0267388 A1 | 12/2005 | Hanna |
| 2005/0283259 A1 | 12/2005 | Wolpow |
| 2006/0047215 A1 | 3/2006 | Newman et al. |
| 2006/0064139 A1 | 3/2006 | Chung et al. |
| 2006/0149119 A1 | 7/2006 | Wang |
| 2006/0190057 A1 | 8/2006 | Reese |
| 2006/0195159 A1 | 8/2006 | Bradley et al. |
| 2006/0206163 A1 | 9/2006 | Wahlstrand et al. |
| 2006/0247985 A1 | 11/2006 | Liamos et al. |
| 2007/0053466 A1 | 3/2007 | Klostermann |
| 2007/0088419 A1 | 4/2007 | Fiorina et al. |
| 2007/0097593 A1 | 5/2007 | Armstrong |
| 2007/0100275 A1 | 5/2007 | Fischer et al. |
| 2007/0173890 A1 | 7/2007 | Armstrong |
| 2007/0213790 A1 | 9/2007 | Nolan et al. |
| 2007/0276451 A1 | 11/2007 | Rigaux |
| 2008/0015641 A1 | 1/2008 | Armstrong et al. |
| 2008/0045882 A1 | 2/2008 | Finsterwald |
| 2008/0071626 A1 | 3/2008 | Hill |
| 2008/0097564 A1 | 4/2008 | Lathrop |
| 2008/0132974 A1 | 6/2008 | Strother et al. |
| 2008/0207985 A1 | 8/2008 | Farone |
| 2008/0208266 A1 | 8/2008 | Lesser et al. |
| 2008/0215113 A1 | 9/2008 | Pawlowicz |
| 2008/0275293 A1 | 11/2008 | Lattner et al. |
| 2008/0281368 A1 | 11/2008 | Bulkes et al. |
| 2008/0319505 A1 | 12/2008 | Boyden et al. |
| 2009/0048642 A1 | 2/2009 | Goroszeniuk |
| 2009/0054952 A1 | 2/2009 | Glukhovsky et al. |
| 2009/0076559 A1 | 3/2009 | Libbus et al. |
| 2009/0092271 A1 | 4/2009 | Fay et al. |
| 2009/0099623 A1 | 4/2009 | Bentwich |
| 2009/0112280 A1 | 4/2009 | Wingeier et al. |
| 2009/0177243 A1 | 7/2009 | Lebedev et al. |
| 2009/0200692 A1 | 8/2009 | Chang |
| 2009/0210028 A1 | 8/2009 | Rigaux et al. |
| 2009/0240303 A1 | 9/2009 | Wahlstrand et al. |
| 2009/0270947 A1 | 10/2009 | Stone et al. |
| 2009/0287108 A1 | 11/2009 | Levy |
| 2010/0057154 A1 | 3/2010 | Dietrich et al. |
| 2010/0076533 A1 | 3/2010 | Dar et al. |
| 2010/0094375 A1 | 4/2010 | Donders et al. |
| 2010/0145399 A1 | 6/2010 | Johari et al. |
| 2010/0145428 A1 | 6/2010 | Cameron et al. |
| 2010/0152817 A1 | 6/2010 | Gillbe |
| 2010/0222734 A1 | 9/2010 | Jayes et al. |
| 2010/0256436 A1 | 10/2010 | Partsch et al. |
| 2010/0318168 A1 | 12/2010 | Bignetti |
| 2011/0029045 A1 | 2/2011 | Cevette et al. |
| 2011/0034756 A1 | 2/2011 | Hacking et al. |
| 2011/0077660 A1 | 3/2011 | Janik et al. |
| 2011/0082326 A1 | 4/2011 | Mishelevich et al. |
| 2011/0082515 A1 | 4/2011 | Libbus et al. |
| 2011/0093033 A1 | 4/2011 | Nekhendzy |
| 2011/0106220 A1 | 5/2011 | DeGiorgio et al. |
| 2011/0112394 A1 | 5/2011 | Mishelevich |
| 2011/0112590 A1 | 5/2011 | Wu et al. |
| 2011/0114191 A1 | 5/2011 | Wheater et al. |
| 2011/0137381 A1 | 6/2011 | Lee et al. |
| 2011/0144716 A1 | 6/2011 | Bikson et al. |
| 2011/0160811 A1 | 6/2011 | Walker |
| 2011/0172752 A1 | 7/2011 | Bingham et al. |
| 2011/0190846 A1 | 8/2011 | Ruffini et al. |
| 2011/0230701 A1 | 9/2011 | Simon et al. |
| 2011/0230702 A1 | 9/2011 | Honour |
| 2011/0230938 A1 | 9/2011 | Simon et al. |
| 2011/0270345 A1 | 11/2011 | Johnston et al. |
| 2011/0276112 A1 | 11/2011 | Simon et al. |
| 2011/0288610 A1 | 11/2011 | Brocke |
| 2011/0301683 A1 | 12/2011 | Axelgaard |
| 2011/0307029 A1 | 12/2011 | Hargrove |
| 2011/0319950 A1 | 12/2011 | Sullivan |
| 2012/0016431 A1 | 1/2012 | Paul et al. |
| 2012/0029591 A1 | 2/2012 | Simon et al. |
| 2012/0029601 A1 | 2/2012 | Simon et al. |
| 2012/0109251 A1 | 5/2012 | Lebedev et al. |
| 2012/0149973 A1 | 6/2012 | Holloway |
| 2012/0165759 A1 | 6/2012 | Rogers et al. |
| 2012/0182924 A1 | 7/2012 | Gaines et al. |
| 2012/0184801 A1 | 7/2012 | Simon et al. |
| 2012/0185020 A1 | 7/2012 | Simon et al. |
| 2012/0209340 A1 | 8/2012 | Escribano |
| 2012/0209346 A1 | 8/2012 | Bikson et al. |
| 2012/0245409 A1 | 9/2012 | Liang |
| 2012/0245653 A1 | 9/2012 | Bikson et al. |
| 2012/0296390 A1 | 11/2012 | Nakashima et al. |
| 2012/0302912 A1 | 11/2012 | Moffitt et al. |
| 2012/0306628 A1 | 12/2012 | Singhal |
| 2013/0023951 A1 | 1/2013 | Greenspan |
| 2013/0035734 A1 | 2/2013 | Soler et al. |
| 2013/0041235 A1 | 2/2013 | Rogers et al. |
| 2013/0060304 A1 | 3/2013 | La Tendresse et al. |
| 2013/0066395 A1 | 3/2013 | Simon et al. |
| 2013/0079659 A1 | 3/2013 | Akhadov et al. |
| 2013/0096641 A1 | 4/2013 | Strother et al. |
| 2013/0131551 A1 | 5/2013 | Raghunathan et al. |
| 2013/0158627 A1 | 6/2013 | Gozani et al. |
| 2013/0184779 A1 | 7/2013 | Bikson et al. |
| 2013/0204315 A1 | 8/2013 | Wongsarpigoon et al. |
| 2013/0226275 A1 | 8/2013 | Duncan |
| 2013/0253613 A1 | 9/2013 | Salahovic et al. |
| 2013/0267761 A1 | 10/2013 | Bentwich |
| 2013/0282095 A1 | 10/2013 | Mignolet et al. |
| 2013/0304175 A1 | 11/2013 | Voegele et al. |
| 2013/0318168 A1 | 11/2013 | Demain et al. |
| 2013/0325096 A1 | 12/2013 | Dupelle et al. |
| 2013/0333094 A1 | 12/2013 | Rogers et al. |
| 2014/0031895 A1 | 1/2014 | Rahimi et al. |
| 2014/0057232 A1 | 2/2014 | Wetmore et al. |
| 2014/0128939 A1 | 5/2014 | Embrey et al. |
| 2014/0128944 A1 | 5/2014 | Stem et al. |
| 2014/0163645 A1 | 6/2014 | Dinsmoor et al. |
| 2014/0182350 A1 | 7/2014 | Bhavaraju et al. |
| 2014/0186807 A1 | 7/2014 | Rastatter et al. |
| 2014/0222102 A1 | 8/2014 | Lemus et al. |
| 2014/0257449 A1 | 9/2014 | Helmer |
| 2014/0275933 A1 | 9/2014 | Meyer et al. |
| 2014/0277324 A1 | 9/2014 | DiUbaldi et al. |
| 2014/0309709 A1 | 10/2014 | Gozani et al. |
| 2014/0336728 A1 | 11/2014 | Franke et al. |
| 2014/0371814 A1 | 12/2014 | Spizzirri et al. |
| 2015/0066104 A1 | 3/2015 | Wingeier et al. |
| 2015/0224310 A1 | 8/2015 | Sharma et al. |
| 2015/0230863 A1 | 8/2015 | Youngquist et al. |
| 2015/0238762 A1* | 8/2015 | Pal ............... A61N 1/36034 607/45 |
| 2015/0257970 A1 | 9/2015 | Mucke et al. |
| 2015/0335877 A1 | 11/2015 | Jeffery et al. |
| 2015/0360030 A1* | 12/2015 | Cartledge ........... A61N 1/3603 607/136 |
| 2016/0008632 A1 | 1/2016 | Wetmore et al. |
| 2016/0074657 A1 | 3/2016 | Kwan et al. |
| 2016/0106975 A1 | 4/2016 | Shore et al. |
| 2016/0279022 A1 | 9/2016 | Hyde et al. |
| 2016/0279435 A1 | 9/2016 | Hyde et al. |
| 2016/0346530 A1 | 12/2016 | Jeffery et al. |
| 2017/0027812 A1 | 2/2017 | Hyde et al. |
| 2017/0076414 A1 | 3/2017 | Egnal et al. |
| 2017/0224990 A1 | 8/2017 | Goldwasser et al. |
| 2017/0368297 A1 | 12/2017 | Tyler et al. |
| 2018/0001077 A1 | 1/2018 | Cook et al. |
| 2018/0169411 A1 | 1/2018 | Goodall et al. |
| 2018/0036533 A1 | 2/2018 | Yoo et al. |
| 2018/0050171 A1 | 2/2018 | Tabert et al. |
| 2018/0272118 A1 | 9/2018 | Goldwasser et al. |
| 2019/0001117 A1 | 1/2019 | Ben-David et al. |
| 2019/0151646 A1 | 5/2019 | Cakmak |
| 2019/0321636 A1 | 10/2019 | Law et al. |
| 2019/0336765 A1 | 11/2019 | Charlesworth et al. |
| 2020/0188660 A1 | 6/2020 | Franke et al. |
| 2022/0118253 A1 | 4/2022 | Wetmore et al. |
| 2022/0160995 A1 | 5/2022 | Wetmore et al. |

(56) References Cited

U.S. PATENT DOCUMENTS

FOREIGN PATENT DOCUMENTS

| | | |
|---|---|---|
| CN | 1704131 A | 12/2005 |
| CN | 1842356 A | 10/2006 |
| CN | 101234233 A | 8/2008 |
| CN | 101244314 A | 8/2008 |
| CN | 201353374 Y | 12/2009 |
| CN | 102245253 A | 11/2011 |
| CN | 102725021 A | 10/2012 |
| CN | 102906752 A | 1/2013 |
| CN | 103517732 A | 1/2014 |
| EP | 502919 B1 | 11/1993 |
| EP | 801957 A1 | 10/1997 |
| EP | 09965358 A2 | 12/1999 |
| EP | 1529550 A1 | 5/2005 |
| EP | 1502623 B1 | 11/2007 |
| EP | 1922989 A2 | 5/2008 |
| EP | 1551290 B1 | 8/2008 |
| EP | 2024018 A2 | 2/2009 |
| EP | 2314346 A1 | 4/2011 |
| EP | 1559369 B1 | 3/2012 |
| EP | 2069001 B1 | 2/2013 |
| EP | 1556135 B1 | 9/2017 |
| JP | 49061984 A | 6/1974 |
| JP | 05031197 A | 2/1993 |
| JP | 06339531 A | 12/1994 |
| JP | 10108913 A | 4/1998 |
| JP | 2001129100 A | 5/2001 |
| JP | 2001293097 A | 10/2001 |
| JP | 2002306604 A | 10/2002 |
| JP | 200310230 A | 1/2003 |
| JP | 2006192302 A | 7/2006 |
| JP | 3129187 U | 1/2007 |
| JP | 2007535372 A | 12/2007 |
| JP | 200985901 A | 4/2009 |
| JP | 2009513248 A | 4/2009 |
| JP | 2011118293 A | 6/2011 |
| JP | 2011519654 A | 7/2011 |
| JP | 2013512076 A | 4/2013 |
| WO | WO92/06737 A1 | 4/1992 |
| WO | WO93/17628 A1 | 9/1993 |
| WO | WO94/00188 A1 | 1/1994 |
| WO | WO94/00189 A1 | 1/1994 |
| WO | WO01/08071 A1 | 2/2001 |
| WO | WO01/78834 A1 | 10/2001 |
| WO | WO03/018120 A1 | 3/2003 |
| WO | WO03/105945 A2 | 12/2003 |
| WO | WO2004/017675 A1 | 2/2004 |
| WO | WO2005/110531 A1 | 11/2005 |
| WO | WO2006/113801 A2 | 10/2006 |
| WO | WO2006/138702 A2 | 12/2006 |
| WO | WO2008/155114 A1 | 12/2008 |
| WO | WO2009/089014 A1 | 7/2009 |
| WO | WO2009/137683 A2 | 11/2009 |
| WO | WO2009/147599 A1 | 12/2009 |
| WO | WO2010/047834 A1 | 4/2010 |
| WO | WO2010/067145 A1 | 6/2010 |
| WO | WO2010/120823 A2 | 10/2010 |
| WO | WO2011/044176 A1 | 4/2011 |
| WO | WO2011/147546 A1 | 12/2011 |
| WO | WO-2012082960 A2 * 6/2012 ........... A61N 1/0456 | |
| WO | WO2012/089588 A1 | 7/2012 |
| WO | WO2012/116407 A1 | 9/2012 |
| WO | WO2012/129574 A2 | 9/2012 |
| WO | WO2012/150600 A2 | 11/2012 |
| WO | WO2012/156051 A1 | 11/2012 |
| WO | WO2012/156052 A2 | 11/2012 |
| WO | WO2013/071307 A1 | 5/2013 |
| WO | WO2013/192582 A1 | 12/2013 |
| WO | WO2014/107624 A1 | 7/2014 |
| WO | WO2014/195516 A1 | 12/2014 |
| WO | WO2015/036420 A1 | 3/2015 |
| WO | WO2015/061663 A1 | 4/2015 |
| WO | WO2015/143053 A1 | 9/2015 |
| WO | WO2017/098300 A1 | 6/2017 |
| WO | WO2017/132573 A1 | 8/2017 |
| WO | WO2017/201525 A1 | 11/2017 |
| WO | WO2018/227165 A1 | 12/2018 |
| WO | WO2020/150733 A1 | 7/2020 |
| WO | WO2020/150737 A1 | 7/2020 |

OTHER PUBLICATIONS

Akbari et al.; Development and evaluation of buccoadhesive propranolol hydrochloride tablet formulations: effects of fillers; IL Farmaco; 59(2); pp. 155-161; Feb. 2004.

Aston-Jones et al.; An integrative theory of locus coeruleus-norepinephrine function: adaptive gain and optimal performance; Annu. Rev. Neurosci.; 28: pp. 403-450; Jul. 21, 2005.

Aston-Jones et al.; Role of locus coeruleus in attention and behavioral flexibility; Biological Psychiatry; 46(9); pp. 1309-1320; Nov. 1, 1999.

Axelgaard Manufacturing Co. Ltd.; Little PALS® (product information); 2 pgs.; printed Feb. 11, 2013 from http://www.axelgaard.com/prod_little-pals.html.

Axelgaard Manufacturing Co. Ltd.; PALS® Platinum Blue (product information); 2 pgs.; printed Feb. 11, 2013 from http://www.axelgaard.com/prod_pals-platinum-blue.html.

Backhaus et al.; Sleep disturbances are correlated with decreased morning awakening salivary cortisol; Psychoneuroendocrinology; 29(9): pp. 1184-1191; Oct. 31, 2004.

Basta et al.; Chronic Insomnia and the Stress System; Sleep Medicine Clinics; 2(2): pp. 279-291; (Author Manuscript, 20 pages); Jun. 30, 2007.

Ben-Menachem et al.; Surgically implanted and no-invasive vagus nerve stimulation: a review of efficacy, safety and tolerability; Euorpean Journal of Neurology; 22(9); pp. 1260-1268; Sep. 2015.

Berlad et al.; Power spectrum analysis and heart rate variability in Stage 4 and REM sleep: evidence for state-specific changes in autonomic dominance; Journal of Sleep Research; 2(2): pp. 88-90; Jun. 1, 1993.

Berridge et al.; The locus coeruleus-noradrenergic system: modulation of behavioral state and state-dependent cognitive processes; Brain Research Reviews; 42(1); pp. 33-84; Apr. 30, 2003.

Brown et al.; Control of sleep and wakefulness; Physiological reviews; 92(3); pp. 1087-1187; Jul. 1, 2012.

Brown et al.;Locus ceruleus activation suppresses feedforward interneurons and reduces beta-gamma electroencephalogram frequencies while it enhances theta frequencies in rat dentate gyrus; Journals of Neuroscience; 25(8): pp. 1985-1991; Feb. 23, 2005.

Buchanan et al.; Salivary alpha-amylase levels as a biomarker of experienced fear; Communicative and Integrative Biology; 3(6); pp. 525-527; Nov. 1, 2010.

Buckley et al.; On the Interactions of the Hypothalamic-Pituitary-Adrenal (HPA) Axis and Sleep: Normal HPA Axis Activity and Circadian Rhythm, Exemplary Sleep Disorders; The Journal of Clinical Endocrinology and Metabolism; 90(5); pp. 3106-3114; May 1, 2005.

Buysse et al.; The Pittsburgh Sleep Quality Index: a new instrument for psychiatric practice and research; Psychiatric Research; 28(2); pp. 193-213; May 31, 1989.

Caporale et al.; Spike timing-dependent plasticity: a hebbian learing rule; Annu. Rev. Neurosci.; 31; pp. 25-46; Jul. 2008.

Carter et al.; Tuning arousal with optogenetic modulation of locus coeruleus neurons; Nature Neuroscience; 13(12); pp. 1526-1533; Dec. 1, 2010.

Chaieb et al.; Transcranial alternating current stimulation in the low kHz range increases motor cortex excitability; Restor Neurol Neurosci; 29(3); pp. 167-175; Mar. 2011.

Clancy et al.; Non-invasive vagus nerve stimulation in healthy humans reduces sympathetic nerve activity; Brain Stimulation; 7(6); pp. 871-877; Nov. 2014.

Cook et al.; Trigeminal nerve stimulation in major depressive disorder: acute outcomes in an open pilot study; Epilepsy and Behavior; 28(2): pp. 221-226; Aug. 31, 2013.

(56) References Cited

OTHER PUBLICATIONS

Coutinho et al.; Musical emotions: predicting second-by-second subjective feelings of emotion from low-level psychoacoustic features and physiological measurements; Emotion; 11(4); pp. 921-937; Aug. 2011.
Couto et al.; Descriptive and functiional neuroanatomy of locus coeruleus-nonsdrenaline-containing neutrons involvement in bradykinin-induced antinociception on principal sensory trigeminal nucleus; Journal of Chemical Neuroanatomy; 32(1); pp. 28-45; Aug. 2006.
Dan et al.; Spike timing-dependent plasticity: from synapse to perception; Physiological Reviews; 86(3); pp. 1033-1048; Jul. 2006.
DaSilva et al.; Electrode positioning and montage in transcranial direct current stimulation; J Vis Exp; 51; e2744; 11 pgs.; May 2011.
De Ridder et al.; Multitarget surgical neuromodulation: combined C2 and auditory cortex implantation for tinnitus; Neuroscience Letters; 30(591); pp. 202-206; Mar. 2015.
De Ridder et al.; Placebo-controlled vagus nerve stimulation paired with tones in a patient with refractory tinnitus: a case report; Otology and Neurotology; 36(4); pp. 575-580; Apr. 2015.
Degiorgio et al., Trigeminal nerve stimulation for epilepsy: long-term feasibility and efficacy; Neurology; 72(10): pp. 936-938; Mar. 10, 2009.
Degiorgio et al.; Randomized controlled trial of trigeminal nerve stimulation for drug-resistant epilepsy; Neurology; 80(9); pp. 786-791; Feb. 26, 2013.
Dehmel et al.; Cross-model interactions of auditory and somatic inputs in the brainstem and midbrain and their imbalance in tinnitus and deafness; American Journal of Audiology; 17(2); pp. S193-S209; 40 pages; (Author Manuscript); Dec. 2008.
Digitimer Ltd.; DS2 and DS3 Isolated Stimulator (product information); 2 pgs.; downloaded from http://www.digitimer.com/research/stimulators/index.htm on Feb. 10, 2014.
Elder et al.; The cortisol awakening response—applications and implications for sleep medicine; Sleep Medicine Reviews; 18(3): pp. 215-224; Jun. 30, 2014.
Electozyme; Company and Product Information; 3 pgs.; printed Feb. 11, 2014 from http://electrozyme.com/applications/.
Engelberg et al.; Transcutaneous electrical stimulation for tinnitus; The Laryngoscope; 95(10); pp. 1167-1172; Oct. 1985.
Eschenko et al.; Noradrenergic neurons of the locus coeruleus are phase locked to cortical up-down states during sleep; Cerebral Cortex; 22(2); pp. 426-435; Feb. 1, 2012.
Fang et al.; Transcutaneous vagus nerve stimulation modulates default mode network in major depressive disorders; Biological Psychiatry; 79(4); pp. 266-273; 18 pages (Author Manuscript); Feb. 2016.
Feurra et al.; Frequency specific modulation of human somatosensory cortex; Front Psychol; 2(13); 6 pgs.; Feb. 2011.
Frangos et al; Non-invasive access to the vagus nerve central projections via electrical stimulation of the external ear: fMRI evidence in humans; Brain Stimulation; 8(3); pp. 624-636; 13 pages (Author Manuscript); May 2015.
Franowicz et al.; Treatment with the noradrenergic alpha-2 agonist clonidine, but not diazepam, improves spatial working memory in normal young rhesus monkeys; Neuropsychopharmacology; 21(5); pp. 611-621; Nov. 1, 1999.
Garcia-Rill et al.; Pedunculopontine arousal system physiology—implications for insomnia; Sleep Science; 8(2); pp. 92-99; Apr. 2015.
Garraway et al.; Modulatory actions of serotonin, norepinephrine, dopamine, and acetylcholine in spinal cord deep dorsal horn neurons; Journal of Neurophysiology; 86(5); pp. 2183-2194; Nov. 1, 2001.
GoFLOW; tDCS Kit; product information; 9 pgs..; printed Feb. 10, 2014 (http://flowstateengaged.com/).
Golestanirad et al; Analysis of fractal electrodes for efficient neural stimulation; Frontiers in Neurengineering; 6(3); 10 pages; Jul. 2013.
Gracenote; Timeline-metadata-api; 3 pages; retrieved from the internet Jul. 7, 2015; (https://github.com/gracenote/timeline-metadata-api/blob/master/README.md).
Granger et al.; Salivary alpha-amylase in biobehavioral research: recent developments and applications; Annals of the New York Academy of Sciences; 1098(1); pp. 122-144; Mar. 1, 2007.
Grindhouse Wetware; Thinking Cap; product information; 1 pg.; printed Feb. 10, 2014 (http://www.grindhousewetware.com/thinkingcap.html).
Gummadaveli et al.; Neurostimulation to improve level of consciousness in patients with epilepsy; Neurosurgical Focus; 38(6); E10, 15 pages; Jun. 2015.
Gummadavelli et al.; Neurostimulation to improve level of consciousness in patients with epilepsy. Neurosurgical Focus; 38(6); pp. E10; (manuscript version, 14 pages); Jun. 2015.
Hagenow et al.; Histamine H4 receptor antagonists: a new approach for tinnitus treatment?; Recent Patents on CNS Drug Discovery; 10(1); pp. 6-9; Apr. 2015.
Hajos et al.; Norepinephrine but not serotonin reuptake inhibitors enhance theta and gamma activity of the septo-hippocampal system; Neuropsychopharmacology; 28(5); pp. 857-864; May 1, 2003.
Hass et al.; Waking with the hypothalamus. Pflugers Arch R Eur. J. Physiol.; 463(1): pp. 31-42; Jan. 1, 2012.
Herwig et al.; Intracortical excitability is modulated by a norepinephrine-reuptake inhibitor as measured with paired-pulse transcranial magnetic stimulation; Psychopharmacology (Berl); 164(2): pp. 228-232; Nov. 18, 2002.
Hirotsu et al.; Interactions between sleep, stress, and metabolism; From physiological to pathological conditions; Sleep Science; 8(3); pp. 143-152; Nov. 2015.
Horvath et al.; Evidence that transcranial direct current stimulation (tDCS) generates little-to-no reliable neurophysiologic effect beyond MEP amplitude modulation in healthy human subjects: A systematic review; Neuropsychologia; 66: pp. 213-236; Jan. 31, 2015.
Hyvarinen et al.; Transcutaneous vagus nerve stimulation modulates tinnitus-related beta and gamma-band activity; Ear and Hearing; 36(3); pp. e76-e85; 10 pages (Author Manuscript); May 2015.
Just et al.; Bold responses to trigeminal nerve stimulation; Magnetic Resonance Imaging; 28(8): pp. 1143-1151; Oct. 31, 2010.
Kanai et al.; Frequency-dependent electrical stimulation of the visual cortex; Curr. Biol.; 18(23); pp. 1839-1843; Dec. 9, 2008.
Krahl et al.; Vagus nerve stimulation for epilepsy: a review of central mechanisms; Surgical Neurology International; 3(Suppl4); S255-S259; Oct. 2012.
Kraus et al.; Bold fMRI deactivation of limbic and temporal brain structures and mood enhancing effect by transcutaneous vagus nerve stimulation; Journal of Neural Transmission; 114(11); pp. 1485-1493; Nov. 2007.
Kubota et al.; Role of the brain stem in cardiovascular changes induced by stimulation of the trigeminal nerve; Anesthesia Progress; 36(4-5); pp. 236-237; Jul. 1989.
Lee et al.; Neuromodulation of Brain States; Neuron; 76(1): pp. 209-222. Oct. 4, 2012.
Lemaire et al.; Electrical modulation of neuronal networks in brain-injured patients with disorders of consciousness: a systematic review; Annales francaises d'anesthesie et de reanimation; 33(2); pp. 88-97; Feb. 2014.
Lenhardt; Ultrasonic hearing in humans: applications for tinnitus treatment; Tinnitus Journal; 9(2); pp. 69-75; (year of pub. sufficiently earlier than effective US filing date and any foreign priority date) 2003.
Leproult et al.; Sleep loss results in an elevation of cortisol levels the next evening; Sleep; 20(10): pp. 865-870; Oct. 1997.
Lovibond et al.; The structure of negative emotional states: Comparison of the Depression Anxiety Stress Scales (DASS) with the Beck Depression and Anxiety Inventories; Behaviour Research and Therapy; 33(3); pp. 335-343; Mar. 31, 1995.
Lu et al.; A putative flip-flop switch for control of REM sleep; Nature; 441 (7093): pp. 589-594; Jun. 1, 2006.
Magis et al.; Safety and patients' satisfaction of transcutaneous supraorbital neurostimulation (ISNS) with the Cefaly(R) device in headache treatment: a survey of 2,313 headache sufferers in the general population; The Journal of Headache and Pain, 14(1); pp. 95; (manuscript version, 8 pages) Dec. 1, 2013.

(56) References Cited

OTHER PUBLICATIONS

Mahalingam et al; Transbuccal delivery of 5-Aza-2'-deoxycytidine: effects of drug concentration, buffer solution, and bile salts on permeation: AAPS PharmSci Tech.; 8(3); E28-E33, 10 pages (Author manuscript); Sep. 2007.
Mccreery et al.; Charge density and charge per phase as cofactors in neural injury induced by electrical stimulation; IEEE Transactions on Biomedical Engineering; 37(10); pp. 996-1001; Oct. 1990.
Mcgough et al.; An eight-week, open-trial, pilot feasibility study of trigeminal nerve stimulation in youth with attention-deficit/hyperactivity disorder; Brain Stimulation; 8(2); pp. 299-304; Apr. 30, 2015.
Meltzer et al; Direct comparison of two new actigraphs and polysomnography in children and adolescents; Sleep; 35(1); pp. 159-166; Jan. 1, 2012.
Michiels et al.; The effect of physical therapy treatment in patients with subjective tinnitus: a systematic review; Frontiers in Neuroscience; 10; article 545, 8 pages; Nov. 2016.
Mueller et al.; A quantitative overview of biophysical forces impinging on neural function; Physical Biology; 11(5); 051001, 13 pages; Aug. 2014.
Nash et al.; Differential activation of the human trigeminal nuclear complex by noxious and non-noxious orofacial stimulation; Human Brain Mapping; 30(11); pp. 3772-3782; Nov. 1, 2009.
Nieuwenhuis et al.; Decision making, the P3, and the locus coeruleus-norepinephrine system; Psychological Bulletin; 131(4); pp. 510-532; Jul. 2005.
Parvizi et al.; Consciousness and the brainstem; Cognition; 79(1): pp. 135-160; Apr. 30, 2001.
Paulus, W.; Transcranial electrical stimulation (tES-tDCS; tRNS, tACS) methods; Neuropsychol Rehabil.; 21(5); pp. 602-617; Oct. 2011.
Penzel et al.; Dynamics of Heart Rate and Sleep Stages in Normals and Patients with Sleep Apnea; Neuropsychopharmacology; 28(S1); pp. S48-S53; Jul. 1, 2003.
Piquet et al.; Supraorbital transcutaneous neurostimulation has sedative effects in healthy subjects; BMC Neurology; 11(1); p. 135; (manual transcript, 8 pages); Oct. 28, 2011.
Plewnia et al.; Enhancement of human cortico-motoneuronal excitability by the selective norepinephrine reuptake inhibitor reboxetine; Neuroscience Letters; 330(3); pp. 231-234; Sep. 27, 2002.
Prausnitz; The effects of electric current applied to skin: a review for transdermal drug delivery; Advanced Drug Delivery Reviews; vol. 18; pp. 395-425; Feb. 8, 1996.
Pusch et al.; Electrical stimulation of the vestibular system prevents postoperative nausea and vomiting; Acta Annesthesiol Scand.; 44(9); pp. 1145-1148; Oct. 2000.
Raval et al.; Trigeminal nerve ganglion stimulation-induced neurovascular reflexes in the anaesthetized cat: role of endothelin(B) receptors in cardotid vasodilatation; British Journal of Pharmacology: 126(2); pp. 485-493; Jan. 1999.
Riemann et al.; The hyperarousal model of insomnia: A review of the concept and its evidence; Sleep Medicine Reviews; 14(1); pp. 19-31; Feb. 28, 2010.
Rill et al.; Pedunculopontine arousal system physiology—implications for insomnia; Sleep Science; 8(2); pp. 92-99; Jun. 30, 2015.
Rohleder et al.; Psychosocial stress-induced activation of salivary alpha-amylase: an indicator of sympathetic activity; Annals of the New York Academy of Sciences; 1032(1); pp. 258-263; Dec. 1, 2004.
Saiote et al.; High-frequency TRNS reduces BOLD activity during visuomotor learning; PLOS one; 8(3); e59669; 8 pgs.; Mar. 2013.
Sandri et al.; Mucoadhesive and penetration enhancement properties of three grades of hyaluronic acid using porcine buccal and vaginal tissue, caco-2 cell lines, and rat jejunum; Journal of Pharmacy and Pharmacology; 56(9); pp. 1083-1090; Sep. 2004.
Sara; The locus coeruleus and noradrenergic modulation of cognition; Nature Reviews Neuroscience; 10(3): pp. 211-223. Mar. 1, 2009.
Schmidt et al.; Adrenaline rush: the role of adrenergic receptors in stimulant-induced behaviors; Molecular Pharmacology; 85(4): pp. 640-650; Apr. 1, 2014.
Schutter et al.; Brain oscillations and frequency-dependent modulation of cortical excitability; Brain Stimulation; 4(2); pp. 97-103; Apr. 2011.
Seugnet et al.; Identification of a biomarker for sleep drive in flies and humans; Proceedings of the National Academy of Sciences; 103(52); pp. 19913-19918; Dec. 26, 2006.
Shiozawa et al.; Transcutaneous vagus and trigeminal nerve stimulation for neuropsychiatric disorders: a systematic review; Arquivos de neuro-psiquiatria; 72(7): pp. 542-547; Jul. 2014.
Shore; Multisensory intelgration in the dorsal cochlear nucleus: unit responses to acoustic and trigeminal ganglion; European Journal of Neuroscience; 21(12); pp. 3334-3348; Jun. 2005.
Siegal; Brain mechanisms that control sleep and waking; Die naturwissenshaften; 91(8); pp. 355-365; Aug. 2004.
Siegel; Brain mechanisms that control sleep and waking. Naturwissenschaften; 91(8); pp. 355-365; Aug. 1, 2004.
Sjostrom et al.; Spike timing, calcium signals and synaptic plasticity; Current opinion in Neurobiology; 12(3); pp. 305-314; Jun. 2002.
Somana et al.; Cerebellar afferents from the trigeminal sensory nuclei in the cat. Brain Res.; 38(1); pp. 57-64; Jan. 1980.
Song et al.; Cortical development and remapping through spike timing-dependent plasticity; Neuron; 32(2); pp. 339-350; Oct. 2001.
STD Pharmaceutical Products; Idrostar intophoresis machine (product and use information); 9 pgs.; Dec. 2011 (printed Feb. 11, 2014 from http://www.iontophoresis.info/instructions/).
Strassman et al; Response of brainstem trigeminal neurons to electrical stimulation of the dura; Brain Research; 379(2): pp. 242-250; Aug. 6, 1986.
Tanaka et al.; Salivary alpha-amylase and cortisol responsiveness following electrically stimulated physical stress in bipolar disorder patients; Neuropsychiatric Disease and Treatment; 8; pp. 1899-1905; Jan. 1, 2013.
Terney et al.; Increasing human brain excitability by transcranial high-frequency random noise stimulation; The Journal of Neuroscience; 28(52); pp. 14127-14155; Dec. 2008.
Thoma et al.; Acute stress responses in salivary alpha-amylase predict increases of plasma norepinephrine; Biological Psychology; 91(3): pp. 342-348; Dec. 31, 2012.
Tremblay et al.; Uncertain Outcome of Prefrontal tDCS; Brain Stimulation; 7(6): pp. 773-783; Dec. 31, 2014.
Trevizol et al.; Trigeminal Nerve Stimulation (TNS) for Generalized Anxiety Disorder: A Case Study; Brain Stimulation; 8(3): pp. 659-660; Jan. 1, 2015.
Trevizol et al.; Trigeminal Nerve Stimulation (TNS) for Post-traumatic Stress Disorder: A Case Study; Brain Stimulation; 8(3): pp. 676-678; Jan. 1, 2015.
Turi et al.; Both the cutaneous sensation and phosphene perception are modulated in a frequency-specific manner during transcranial alternating current stimulation; Restor. Neurol. Neurosci.; 31(3); pp. 275-285; Jan. 2013.
Tyler et al.; Experience-dependent modification of primary sensory synapses in the mammalian olfactory bulb; Journal of Neuroscience; 27(35); pp. 9427-9438; Aug. 2007.
Tyler et al.; Transdermal neuromodulation of noradrenergic activity suppresses psychophysiological and biochemical stress responses in humans; Scientific Reports; 5; (manual transcript, 22 pages); Feb. 8, 2015.
Tyler et al.; U.S. Appl. No. 61/550,334 entitled "Improvement of Direct Communication," filed Oct. 21, 2011.
Tyler et al.; U.S. Appl. No. 61/663,409 entitled "Device and Methods for Noninvasive Neuromodulation Using Targeted Transcranial Electrical Stimulation," filed Jun. 22, 2012.
Tyler et al.; U.S. Appl. No. 62/166,674 entitled "Systems and Methods for Suppression of Stress Responses by Transdermal Electrical Neuromodulation," filed May 26, 2015.
Tyler; The mechanobiology of brain function; Neuroscience; 13(12); pp. 867-878; Dec. 2012.

(56) References Cited

OTHER PUBLICATIONS

Upadhyay et al.; Noninvasive mapping of human trigeminal brainstem pathways; Magnetic Resonance in Medicine; 60(5): pp. 1037-1046; Nov. 1, 2008.
Van Stegeren et al.; Salivary alpha amylase as marker for adrenergic activity during stress: effect of betablockade; Psychoneuroendocrinology; 31(1); pp. 137-141; Jan. 31, 2006.
Vanneste et al.; Do tDCS and TMS influence tinnitus transiently via a direct cortical and indirect somatosensory modulating effect? A combined TMS-tDCS and TENS study; Brain Stimulation; 4(4); pp. 242-252; Oct. 2011.
Vanneste et al.; Noninvasive and invasive neuromodulation for the treatment of tinnitus: an overview; Neuromodulation: Technology at the Neural Interface; 15(4); pp. 350-360; Jul. 2012.
Vanneste et al.; Transcutaneous electrical nerve stimulation (TENS) of upper servical nerve (C2) for the treatment of somatic tinnitus; Experimental Brain research; 204(2); pp. 283-287; Jul. 2010.
Voisin et al.; Nociceptive stimulation activates locus coeruleus neurones projecting to the somatosensory thalamus in the rat; The Journal of Physiology; 566( 3); pp. 929-937; Aug. 1, 2005.
Voss et al.; Induction of self awareness in dreams through frontal low current stimulation of gamma activity; Nature Neuroscience; 17(6); pp. 810-812; Jun. 1, 2014.
Watson et al.; Development and validation of brief measures of positive and negative affect: the PANAS scales; Jouranl of Personality and Social Psychology; 54(6); pp. 1063-1070; Jun. 1988.
Weiss et al; Validity of Activity-Based Devices to Estimate Sleep; Journal of Clinical Sleep Medicine : 6(4); pp. 336-342; Aug. 2010.
Wu et al.; Trancutaneous induction of stimulus-timing-dependent plasticity in dorsal cochlear nucleus; Frontiers in Systems Neuroscience; vol. 9; Article 116; 10 pages, doi10.3389/fnsys.2015.00116; Aug. 2015.
Ylikoski et al.; Non-inasive vagus nerve stimulation reduces sympathetic preponderance in patients with tinnitus; Acta Oto Laryngologica; 137(4); pp. 426-431; 6 pages, doi.org/10.1080/00016489.2016.1269197; Apr. 2017.
Zeng et al.; Tinnitus treatment with precise and optimal electric stimulation: opportunities and challenges; Current Opinion in Otolaryngology and Head and Neck Surgery; 23(5); pp. 382-387, 12 pages (Author Manuscript); Oct. 2015.
Adelman et al.; Air conduction, bone conduction, and soft tissue conduction audiograms in normal hearing and stimulated hearing losses; American Academy of Audiology; 26(1); pp. 101-108; Jan. 2015.
Adelman et al.; Investigation of the mechanism of soft tissue conduction explains several perplexing auditory phenomena; Journal of Basic and Clinical Physiology and Pharmacology; 25(3); pp. 269-272; Sep. 2014.
Artusi et al.; Buccal delivery of thiocolchicoside: in vitro and in vivo permeation studies; International Journal of Pharmaceutics; 250(1); pp. 203-213; Jan. 2003.
Berge; Pharmaceutical salts; Journal of Pharmaceutical Sciences; 66(1); p. 1-19; Jan. 1977.
El Kashian et al.; Effects of trigeminal ganglion stimulation on the central auditory system; Hearing Research; 189(1-2); pp. 25-30; Mar. 2004.
Evans; Sleep consciousness and the spontaneous and evoked electrical activity of the brain. Is there a cortical integrating mechanism?; Neurophysiologie Clinique/Clinical Neurophysiology; 33(1); pp. 1-10; Feb. 2003.
French; The reticular formation: the nature of the reticular activating system; Journal of Neurosurgery; 15; pp. 97-115; Jan. 1958.
Fujikado et al.; Two pathways from the facial skin to the superior colliculus in the rat; Brain Research; 212(1); pp. 131-135; May 1981.
Garcia-Rill; The pedunculopotine nucleus; Progress in Neurobiology; 36(5); pp. 363-389; Jan. 1991.
Grunwerg et al.; Somatosensory input and thalamic projection of pedunculopontine tegmental neurons; Neuroreport; 3(8); pp. 673-675; Aug. 1992.
Harting et al.; Spatial relationships of axons arising from the substantia nigra spinal trigeminal nucleus and pedunculopontine tegmental nucleus within the intermediate gray of the cat superior colliculus; journal of Comparative Neurology; 305(4); pp. 543-558; Mar. 1991.
Henry et al.; General review of tinnitus prevalence, mechanisms, effects, and management; Journal of speech, Language, and Hearing research; 48(5); pp. 1204-1235; Oct. 2005.
Herraiz et al.; Trans-electrical nerve stimulation (TENS) for somatic tinnitus; Progress in Brain Research; 166; pp. 389-394; Jan. 2007.
Kaitin et al.; Sleep disturbance produced by electrical stimulation of the locus coeruleus in a human subject; Biological Psychiatry; 21(8-9); pp. 710-716; Jul. 1986.
Kapkin et al.; Transcutaneous electrical stimulation of subjective tinnitus; ORL; Journal for Oto-Rhino-Laryngology and its Related Specialities; 70(3); pp. 156-161; Apr. 2008.
Kreuzer et al.; Feasibility, safety and efficacy of transcutaneous vagus nerve stimulation in chronic tinnitus: an open pilot study; Brain Stimulation; 7(5); pp. 740-747; Sep. 2014.
Laurikainen et al.; Betahistine-induced vascular effects in the rat cochiea; The American Journal of Otology; 14(1); pp. 24-30; Jan. 1993.
Laurikainen et al.; The tonic sympathetic input to the cochlear vasculature in guinea pig; Hearing Research; 105(1-2); pp. 141-145; Mar. 1997.
Lee et al.; Combined effect of oleic acid and polyethylene glycol 200 on buccal permeation of [D-ala2, D-leu5] enkephalin from a cubic phase of glyceryl monooleate; International Journal of Pharmaceutics; 204(1-2); pp. 137-144; Jun. 2000.
Li et al.; High spatiotemporal resolution imaging of the neurovascular response to electrical stimulation of rat peripheral trigeminal nerve as revealed by in vivo temporal laser speckle contrast; Journal of Neuroscience Methods; 176(2); pp. 230-236; Jan. 2009.
Nicolazzo et al; Modification of buccal drug delivery following pretreatment with skin penetration enhancers; journal of Pharmaceutical Sciences; 93(8); pp. 2054-2063; Aug. 2004.
Rubinstein et al.; Electrical suppression of tinnitus with high-rate pulse trains; Otology and Neurology; 24(3); pp. 478-485; May 2003.
Schoenen et al.; Migraine prevention with supraorbital transcutaneous stimulator: a rondomized controlled trial; Neurology; 80(8); pp. 697-704; Feb. 2013.
Seidman et al.; Mechanisms of alterations in the microcirculation of the cochlea; New York Acedemy of Sciences; 884(1); pp. 226-232; Nov. 1995.
Senel et al.; Drug permeation enhancement via buccal route: possibilites and limitations; journal of Controlled Release; 72(1-3); pp. 133-144; May 2001.
Shulman; External electrical tinnitus suppression: a review; The American Journal of Otology; 8(6); pp. 479-484; Nov. 1987.
Sillman et al.; Electrically stimulated increases in cochlear blood flow: II. Evidence of neural mediation; Otolaryngology—Head and Neck Surgery; 101(3); pp. 362-374; Sep. 1989.
Sillman et al.; Electrically timulated increases in cochlear blood flow: I. frequency and intensity effects; Otolarynology—Head and Neck Surgery; 100(4); pp. 308-316; Apr. 1989.
Smith; Axonal projections and connections of the principal sensory trigeminal nucleus in the monkey; Journal of Comparative Neurology; 163(3); pp. 347-375; Oct. 1975.
Starokadomskyy et al.; New absorption promoter for the buccal delivery: preparation and characterization of lysalbinic acid; International Journal of Pharmaceutics; 308(1-2); pp. 149-154; Feb. 2006.
Sudhakar et al.; Buccal bioadhesive drug delivery—a promising option for orally less efficient drugs; journal of Controlled Release; 114(1); pp. 15-40; Aug. 2006.
Tachibana et al.; Effect of transcutaneous electrostimulation on noise-induced temporary threshold shift; Acta Oto Laryngogica; 112(4); pp. 595-598; Jan. 1992.
Pal et al.; U.S. Appl. No. 14/956,193 entitled "Transdermal electrical stimulation devices for modifying or inducing cognitive state," filed Dec. 1, 2015.

(56) References Cited

OTHER PUBLICATIONS

Liu et al.; Recent developments in tough hydrogels for biomedical applications; Gels; 4(2):46; doi:10.3390/gels4020046; 30 pages; May 22, 2018.

* cited by examiner

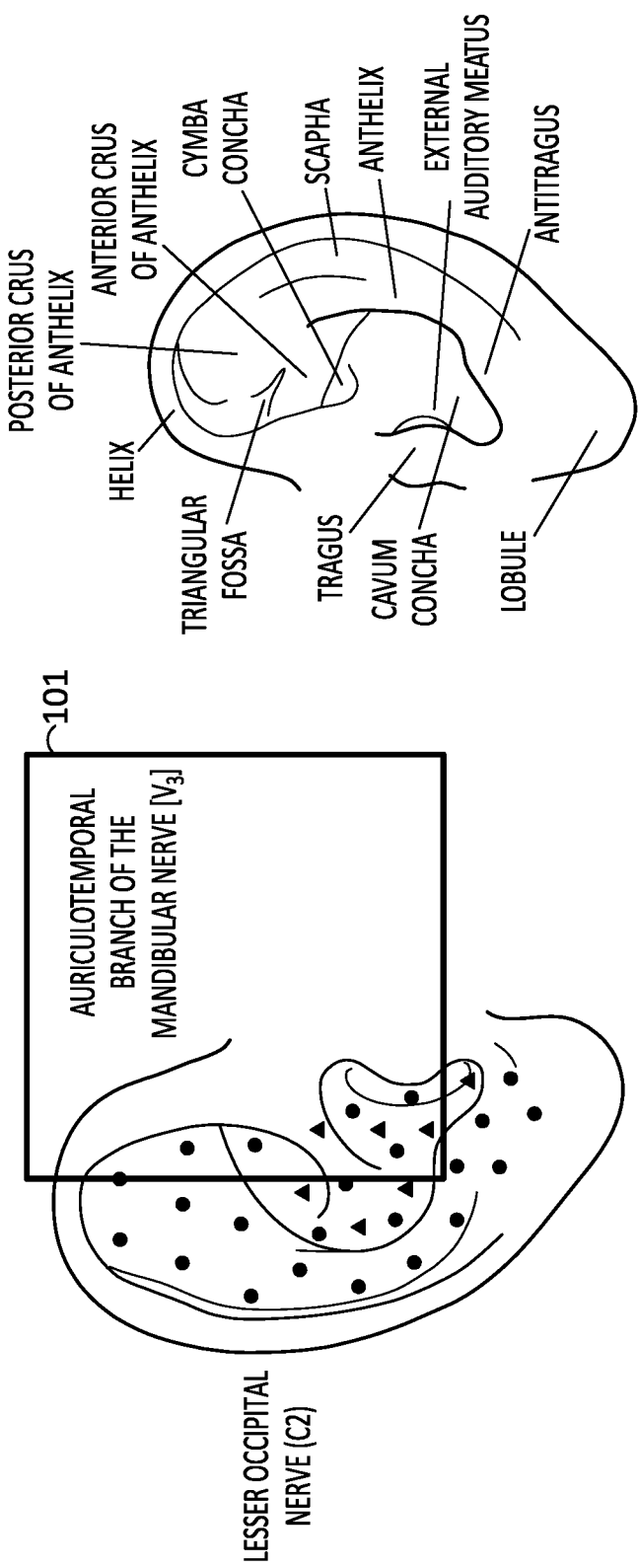

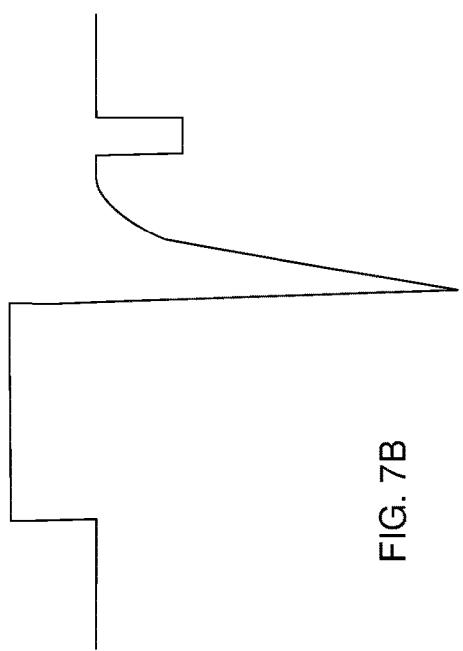
FIG. 7A
FIG. 7B
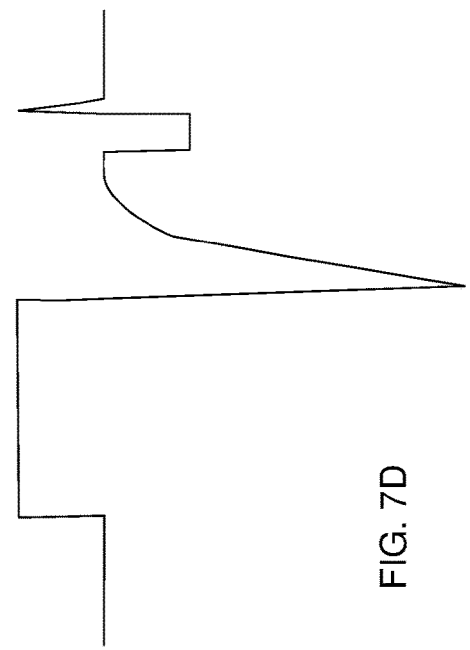
FIG. 7C
FIG. 7D
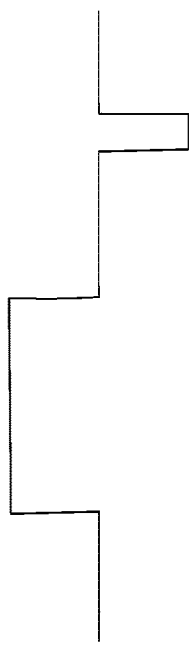
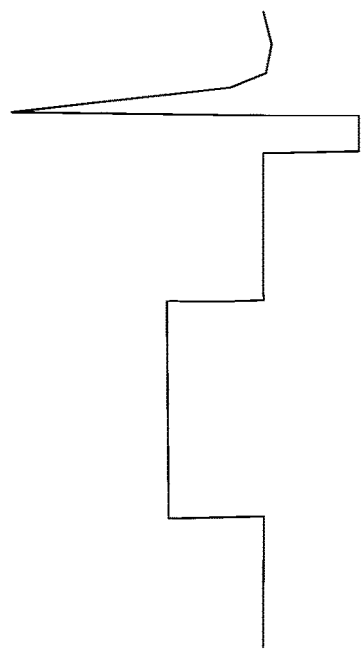

Concentric Concha Stimulating Electrode

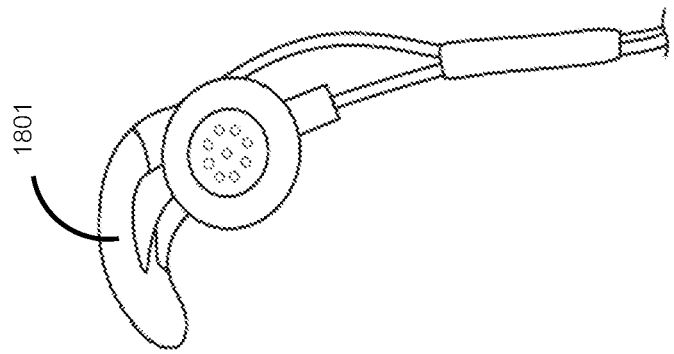
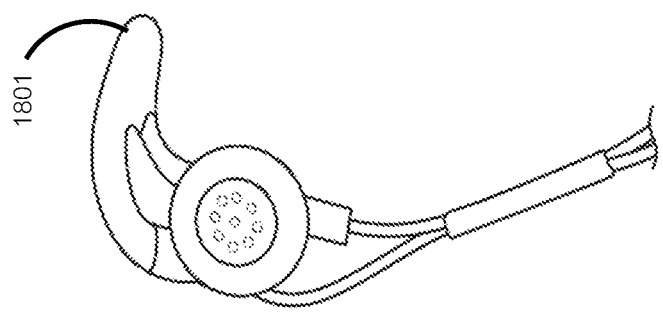
FIG. 18
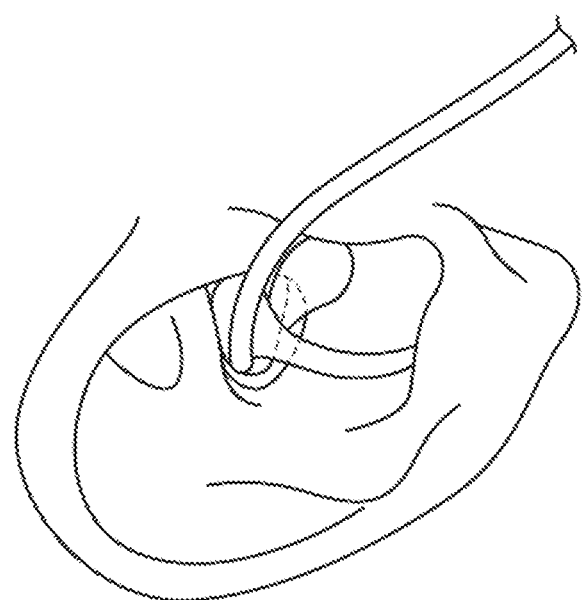
FIG. 17

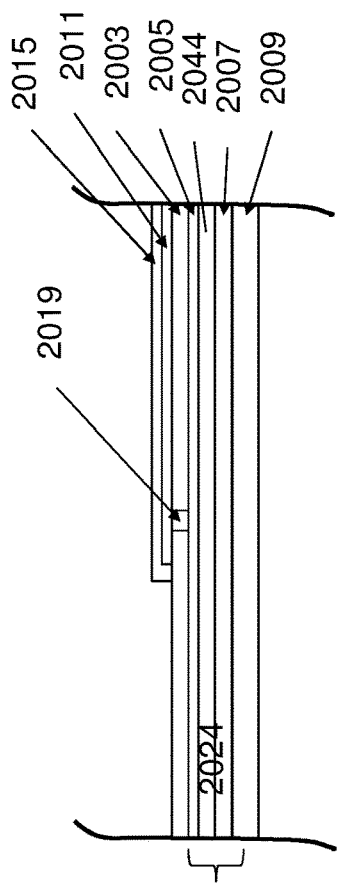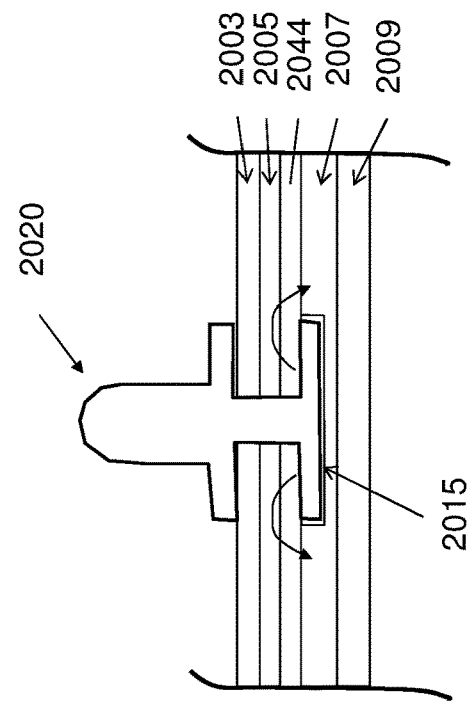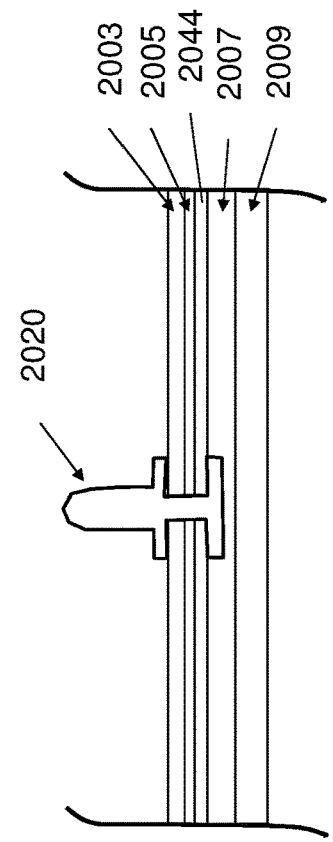

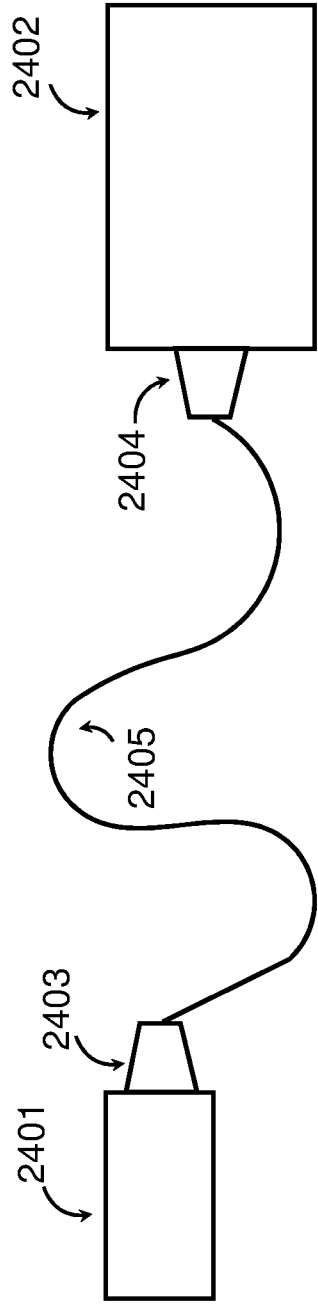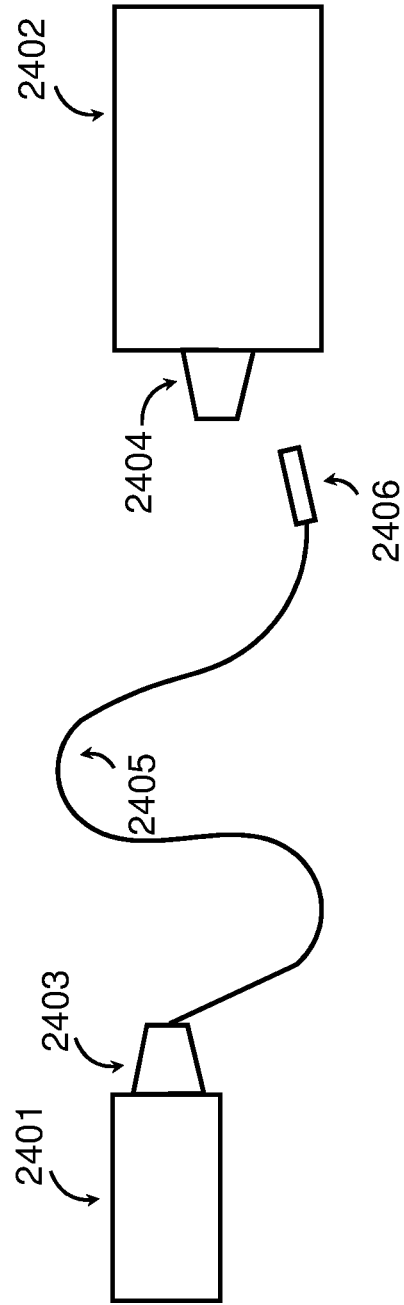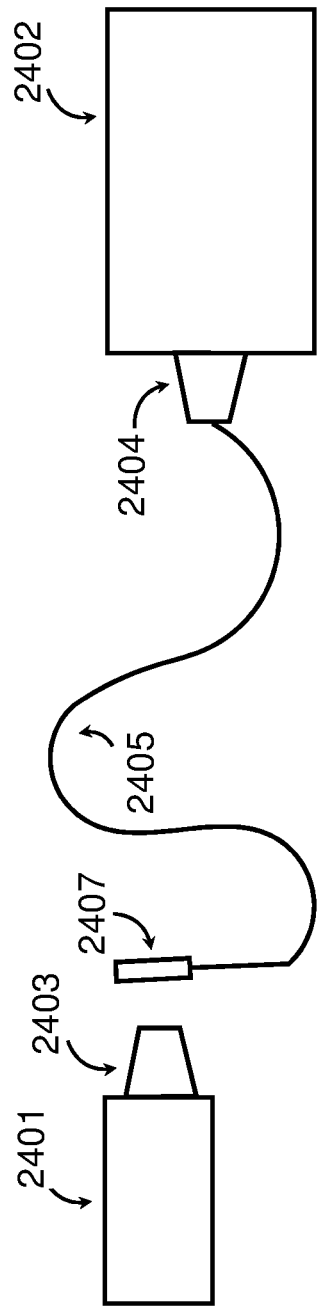

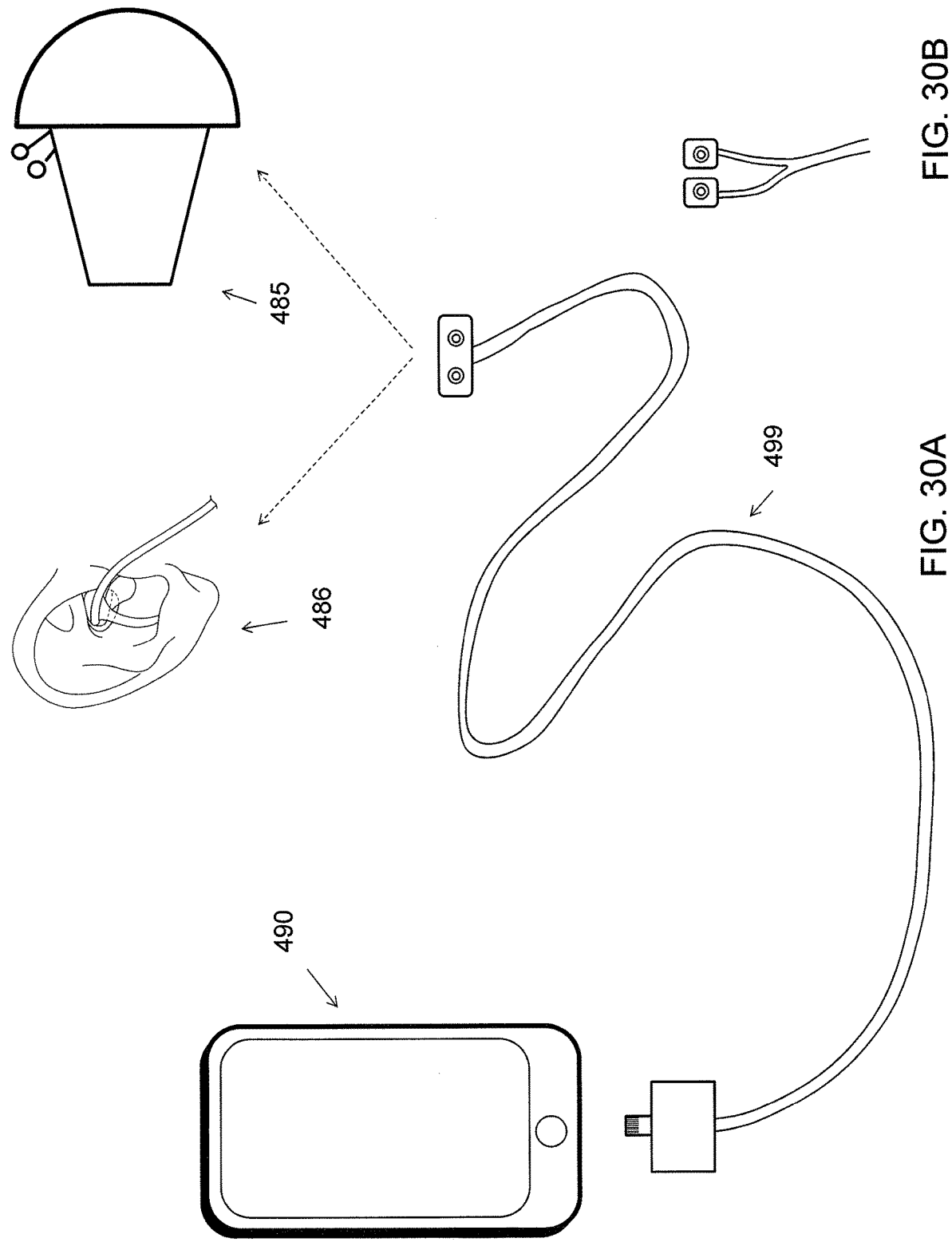

METHODS AND APPARATUSES FOR TRANSDERMAL STIMULATION OF THE OUTER EAR

CROSS REFERENCE TO RELATED APPLICATIONS

This application is a continuation of U.S. patent application Ser. No. 16/588,925, titled "METHODS AND APPARATUSES FOR TRANSDERMAL STIMULATION OF THE OUTER EAR," filed Sep. 30, 2019, now U.S. Pat. No. 11,534,608, which claims priority as a continuation-in-part to U.S. patent application Ser. No. 15/536,148, titled "METHODS AND APPARATUSES FOR TRANSDERMAL STIMULATION OF THE OUTER EAR," which was filed on Jun. 15, 2017, now U.S. Pat. No. 10,426,945, which is a national phase application under 35 USC 371 of International Patent Application No. PCT/US2016/012054, titled "METHODS AND APPARATUSES FOR TRANSDERMAL STIMULATION OF THE OUTER EAR," filed Jan. 4, 2016, now International Publication No. WO 2016/109851, which claims priority to U.S. Provisional Patent Applications: U.S. App. No. 62/099,547, filed on Jan. 4, 2015, titled "SYSTEMS FOR TRANSDERMAL STIMULATION OF THE PINNA AND METHODS OF USING THEM"; U.S. App. No. 62/168,598 filed on May 29, 2015 and titled "METHODS AND APPARATUSES FOR MODIFYING A SUBJECT'S COGNITIVE STATE BY TRANSDERMAL STIMULATION OF THE OUTER EAR"; U.S. App. No. 62/190,205, filed on Jul. 8, 2015, and titled "METHODS AND APPARATUSES FOR MODIFYING A SUBJECT'S COGNITIVE STATE BY TRANSDERMAL ELECTRICAL STIMULATION OF THE OUTER EAR"; U.S. App. No. 62/200,250, filed on Aug. 3, 2015, and titled "METHODS AND APPARATUSES FOR MODIFYING A SUBJECT'S COGNITIVE STATE BY TRANSDERMAL STIMULATION OF THE OUTER EAR"; U.S. App. No. 62/168,615, filed on May 29, 2015, and titled "METHODS AND APPARATUSES FOR TRANSDERMAL ELECTRICAL STIMULATION METHODS AND APPARATUSES FOR TRANSDERMAL ELECTRICAL STIMULATION"; and U.S. App. No. 62/200,256, filed on Aug. 3, 2015, and titled "METHODS AND APPARATUSES FOR TRANSDERMAL ELECTRICAL STIMULATION". All of these patents and patent applications are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods and apparatuses described herein relate to transdermal electrical neuromodulation through the ear. In particular described herein are wearable neurostimulator apparatuses configured to target cranial and/or cervical spinal nerve branches in the pinna to modulate a wearer's cognitive state and/or to treat or diagnose a medical condition in a patient.

BACKGROUND

Electrical stimulation of cranial nerves and/or spinal nerves is a strategy for diagnosing and treating various medical conditions based on the principle that neuromodulation of these nerves induces significant and consistent changes in the brain through brainstem projections. Many of these stimulation techniques act by modulating the activity of cervical spinal and cranial nerve sensory afferents and other fibers projecting back to brainstem regions (e.g., to regulate the activity of the reticular activating system and other bottom-up pathways known to affect cortical gain and psychophysiological arousal). Vagal nerve stimulation at various sites in the head, neck, and upper body is known to have widespread clinical application including for neurological, cardiovascular, pulmonary, renal, hepatic, and immunological disorders.

Implanted cranial or spinal nerve electrical stimulators are generally well localized to targeted nerves, including those in areas of the head generally covered by hair, and can use lower stimulation intensities due to the proximity of the targeted nerve and absence of insulating skin. Though effective, surgical implantation of electrodes is costly and is associated with normal surgical risks. In at least some instances, implanted cranial and/or cervical spinal nerve stimulators cause side effects including difficulty swallowing and hoarseness of the voice.

Transdermal cranial and/or cervical spinal nerve electrical stimulators require less intervention, lower cost, and offer a better safety profile relative to implanted systems. However, transdermal stimulation strategies are believed to be less than optimal in some circumstances, for instance: the targeting of cranial and/or cervical spinal nerves that vary between patients; the difficulty of delivering current comfortably and efficiently through the skin; and skin discomfort mediated by sensory receptors that limits the intensity (or other parameters) of stimulation.

For example, the Electrocore gammaCore® stimulator is a handheld device that targets the vagal nerve in the neck. U.S. Pat. No. 8,843,210 to inventors Simon et al. describe a neck-based stimulation system. This form factor is lacking in terms of miniaturization and ease of use, particularly hands-free use, limiting the activity of users during stimulation and the available contexts for stimulation (i.e. it is difficult to apply handheld stimulation while driving, holding a child, riding a bike, or even eating a meal).

Targeting transdermal electric stimulation (TES) to the pinna may overcome some of these limitations. The pinna generally has little or no hair and several cranial and cervical spinal nerves project to this portion of the ear. Electrical stimulation of branches of the vagal, trigeminal, and facial nerves in the pinna has been described previously. Fewer descriptions exist for targeting cervical spinal nerves (for example the greater auricular nerve) projecting to this region to modulate brain activity. Existing Pinna Electrical Nerve Stimulation (PENS, also referred to as auricular electrical stimulation, auricular TES, auricular stimulation, or auricular electrical nerve stimulation) and methods are not optimal at least because they have not proven effective and reliable for regular use, particularly by untrained users. The waveforms, electrode composition, and mechanical-geometric structures for dermal application of electrodes on the pinna have not yet been able to effectively deliver comfortable waveforms that induce beneficial and significant cognitive effects, and, in some cases, non-cognitive effects. Additionally, systems and methods optimized for stimulating combinations of cranial nerves (trigeminal, facial, and/or vagal) and cervical spinal nerves (greater auricular nerve; C2-3) projecting to this region to modulate brain function do not presently exist. For example, electrode compositions for pinna nerve stimulation that distribute charge uniformly on the targeted skin area and buffer pH changes in the skin would be beneficial improvements on available systems.

Various therapeutic and diagnostic applications of auricular electrical stimulation have been described. In some instances, consumer applications (i.e. 'lifestyle' applications not intended to diagnose or treat any medical condition) for auricular electrical stimulation would be beneficial. For these applications in particular, though also for many therapeutic and diagnostic applications, it may be beneficial for stimulation to be more comfortable—and to induce noticeable and beneficial effects in healthy users. Existing systems and methods are lacking in this regard.

For example, U.S. Pat. No. 5,144,952 to inventors Frachet and David describes an earring pierced through the pinna for transcutaneous electrical stimulation. Though this form factor is minimally invasive (at least with respect to individuals with cosmetic ear piercings), less invasive apparatuses for electrical stimulation of the pinna would be more comfortable and avoid the potential for infection. In at least some instances, this method may be limited because it delivers highly localized stimulation of particular afferents, whereas broader stimulation of zones innervated by cranial and cervical spinal nerves could induce more robust cognitive effects.

Electrostimulation via ear clips is one standard noninvasive means for TES of the pinna. However, the ear clips are generally positioned on the ear lobe, a region with more fatty tissue that causes ear clips to generally have high impedance and limit the intensity of stimulation, as well as the efficacy of neuromodulation of the branches of cranial nerves in the pinna more distant from the ear lobe. Again, the highly localized site of stimulation may preclude some outcomes where more diffuse and global stimulation of several regions of the pinna simultaneously could overcome this limitation. For example, systems and methods for simultaneously stimulating the helix, triangular fossa, and cymba conchae may be beneficial for inducing more prominent changes in psychophysiological arousal than simply stimulating the tragus or ear lobe.

U.S. Pat. No. 5,514,175 to inventors Kim et al. describes a lightweight, portable auricular TES system using bipolar waveforms including those with frequencies of 15 Hz, 500 Hz, and 15,000 Hz and, for example, peak intensity of 150 $\mu A$. A key feature of the system described by Kim et al. is low voltage operation (i.e. 2 volts or less, 10 volts or less). The inventors in the present case have found that such low peak stimulation intensities are limiting for robust neuromodulation of cranial and/or cervical spinal nerves and are not able to induce significant and beneficial physiological and/or cognitive effects. Moreover, the low voltage operation of the systems described by Kim et al. are unsuitable for higher current intensities (e.g. above about 1 mA) due to high skin impedance for small electrodes in the relatively well insulated pinna.

In yet another example, Cerbomed GmBH sells the Nemos® transcutaneous vagal nerve stimulator with an earphone-style assembly containing a pair of electrodes targeting vagal nerve endings in the conch of the ear. Patients carry out stimulation autonomously about 4 hours per day for the treatment of epilepsy. The intensity of stimulation is set by the user and delivered at (for example) 250 $\mu sec$ pulses at 25 Hz at an intensity that causes slight tingling, generally 2 mA or less.

Patents originally assigned to Cerbomed describe auricular stimulation systems and methods for using them that are lacking in at least some instances for delivering comfortable transdermal electrical stimulation that induces a significant and beneficial cognitive effect. In at least some instances, the auricular stimulation systems disclosed by Cerbomed are lacking because they do not incorporate the use of transducers or speakers (headphones for example) for introducing naturalistic stimulation, such as music or sounds.

U.S. Pat. No. 8,506,469 to Deitrich et al describes "a monophasic-modified rectangle impulse with a pulse width of 250 ms, electrical current amplitude between 4 mA and 8 mA stimulation frequency of 25 Hz is used." Also described are pinna stimulation waveforms that are either monopolar or bipolar and in a preferable frequency range of 0.01 to 1000 Hz. However, these auricular transdermal electrical stimulation waveforms are suboptimal in at least some instances for comfortable stimulation at high peak intensities (and with other appropriate waveform parameters) that induce a significant and beneficial cognitive effect.

U.S. Pat. No. 8,688,239 to Hartlep et al. shows an auricular electrical stimulation apparatus with mechanical and geometric features for stable placement in a patient's ear (in the conch) for targeting the auricular branch of the vagal nerve. However, these apparatuses are not configured to use disposable electrodes, including disposable electrodes that include consumptive electrochemistry to improve skin comfort at higher peak stimulation intensities that induce stronger cognitive effects, in at least some instances.

Erfan disclosed a bilateral headset auricular stimulator in U.S. application US2005/0165460 wherein the hardware device hangs as a necklace from a patient's ears similar to a marketed product from Auri-Stim Medical, Inc.

U.S. Pat. No. 8,639,343 to de Vos describes an apnoea treatment that couples measurement of breathing to auricular electrical stimulation at less than 500 Hz.

The products and patent art of Cerbomed, de Vos, and Auri-Stim Medical, Inc. are lacking in the effects induced by stimulation of the pinna, as well as the intensity of stimulation achievable without skin discomfort. New systems for stimulation of cranial and/or cervical spinal nerve projections in the pinna (also referred to as the auricle) that are comfortable at higher peak stimulation intensities and induce beneficial cognitive effects would be desirable.

It would generally be advantageous to provide devices and methods that allow transdermal electrical stimulation of the pinna in a manner that overcomes the problems with pain and efficacy. In particular, it would be beneficial to provide auricular TES devices and methods for modulating (e.g., inducing, enhancing, reversing, or otherwise increasing or changing) a cognitive effect and/or mental state. For example, TES stimulation protocols and electrode configurations that induce a relaxing, calming, anxiolytic, dissociated, high mental clarity, or worry-free state of mind in a subject would be advantageous for improving the subject's experiences and state of mind, as well as addressing insomnia and mitigating negative responses to stress. Similarly TES stimulation protocols and apparatuses that increase a subject's motivation, alertness, subjective (and/or physiological) energy level, or focus would be advantageous for improving a subject's productivity, frequency of physical activity, and providing beneficial states of mind. Due to the way the brain integrates multimodal sensory information, it would be beneficial to provide devices and methods that enable the stimulation of cranial and cervical spinal nerves projecting to the pinna simultaneously combined with naturalistic auditory stimulation, such as music to affect motivation, mood, psychophysiological arousal, and cognition. Described herein are methods and apparatuses (including devices and systems) and methods that may address the problems and opportunities discussed above. Also described herein are methods for treating or diagnosing a subject with auricular TES systems. Electrical stimulation waveforms that activate nerves in the ear (pinna) while causing minimal or limited discomfort would be beneficial for pinna electrical stimulation and are described herein. Conductive form factors that fit comfortably in the ear and provide a generally uniform and/or pH buffering electrode composition would provide an additional benefit and are also described herein.

The various disclosed auricular stimulation systems are further lacking with regard to miniaturization and portability. For lifestyle applications, as well as clinical (i.e. therapeutic or diagnostic) applications, hands-free application with a lightweight, minimally-distracting or intrusive form factor would enhance the ease-of-use and applications for the auricular stimulation system. Systems that are small, lightweight and wearable in an ear (i.e. within the concha and/or triangular fossa), on an ear, or adhesively attached on or near the ear would provide additional benefit relative to handheld systems and systems that require a dedicated handheld or table-top control unit. One system design that enables a smaller neurostimulator control unit is to offload some of the control software and/or power source requirements to a portable user computing device (i.e. a smartphone, smartwatch, or tablet) by coupling to a connector of the portable user computing device with a cable.

SUMMARY OF THE DISCLOSURE

Generally described herein are transdermal electrical stimulators (e.g., neurostimulators configured to modify a subject's cognitive and/or physiological state) that may be worn on a subject's ear or ears. These apparatuses (which may be devices and/or systems) may include a wearable component (such as a headphone component) including in some variations a pair of electrodes for delivering TES to the subject's ear (e.g., pinna) and particularly to the cymba region of the ear, as well as control circuitry such as a processor and/or waveform generator, and a power supply (e.g., battery). In some variations the apparatus may include audio output (e.g., speakers, as for a headphone/headset). The control circuitry and/or battery may be separate from (though connectable to) or integrated with the pair of electrodes. In some variations the electrodes are configured to be worn on/in the subject's ear, and attached or coupled (via a wire or wirelessly) to a body including the control circuitry.

For example, described herein are methods of inducing or enhancing attention, alertness, or mental focus or inducing or enhancing a calm or relaxed mental state, the method comprising: placing a first electrode of a portable transdermal electrical stimulation (TES) applicator into the subject's first ear in contact with a first pinna, and placing a second electrode of a portable TES applicator on the subject; activating the TES applicator to deliver pulsed electrical stimulation between the first and second electrodes at an intensity of 0.25 mA or greater, a duty cycle of greater than 10% and a frequency of greater than 250 Hz; and delivering the pulsed electrical stimulation between the first and second electrodes for 10 seconds or longer.

A method of inducing or enhancing attention, alertness, or mental focus or inducing or enhancing a calm or relaxed mental state, may include: placing a first electrode of a portable transdermal electrical stimulation (TES) applicator into the subject's first ear in contact with a first pinna and placing a second electrode of a portable TES applicator into the subject's second ear in contact with a second pinna; activating the TES applicator to deliver pulsed electrical stimulation between the first and second electrodes with an intensity of 0.25 mA or greater, a duty cycle of greater than 10% and a frequency of greater than 250 Hz; and modifying the subject's cognitive state to induce a calm cognitive state by delivering the pulsed electrical stimulation between the first and second electrodes for 10 seconds or longer.

A method of inducing or enhancing attention, alertness, or mental focus or inducing or enhancing a calm or relaxed mental state may include: placing a portable transdermal electrical stimulation (TES) applicator into a subject's first ear so that a first and second electrode of a portable TES applicator contact a skin of the subject's pinna so that at least one of the first and second electrodes are in contact with the subject's cymba; activating the portable TES applicator to deliver a pulsed electrical stimulation having an intensity of greater than 0.25 mA between the first electrode positioned on the subject's pinna and the second electrode on the subject's pinna; delivering audio output to the subject from a speaker coupled to the portable TES applicator concurrently with delivery of the pulsed electrical stimulation; and applying the transdermal electrical stimulation between the first and second electrodes for 10 seconds or longer.

For example, described herein are methods of modifying a subject's cognitive state, the method comprising: placing a portable transdermal electrical stimulation (TES) applicator into the subject's ear so that a first and second electrode of a portable TES applicator contact the skin of the subject's pinna; activating the TES applicator to deliver pulsed electrical stimulation with an intensity of 0.25 mA or greater; and modifying the subject's cognitive state by applying the pulsed electrical stimulation between the first and second electrodes for 10 seconds or longer.

Any of the methods of modifying a subject's cognitive state described herein may be methods of modifying a subject's cognitive state to induce or enhance attention, alertness, or mental focus or to induce or enhance a calm or relaxed mental state. For example, such a method may include: placing a portable transdermal electrical stimulation (TES) applicator into the subject's ear so that a first and second electrode of a portable TES applicator contact the skin of the subject's pinna so that at least one of the first and second electrodes are in contact with the subject's pinna (e.g., the concha, such as the cymba and/or cavum region of the pinna); activating the portable TES applicator to deliver a pulsed electrical stimulation having an intensity of greater than 0.25 mA between the first electrode positioned on the subject's pinna and the second electrode on the subject's pinna; delivering audio output to the subject from a speaker coupled to the portable TES applicator; and modifying the subject's cognitive state by applying the transdermal electrical stimulation between the first and second electrodes for 10 seconds or longer.

Also described herein are methods of stimulation the vagus nerve non-invasively by TES. In particular, described herein are methods of non-invasively stimulating the vagus nerve to induce or enhance attention, alertness, or mental focus or inducing or enhancing a calm or relaxed mental state. For example any of these method may include: placing a first electrode of a portable transdermal electrical stimulation (TES) applicator into the subject's first ear in contact with a first pinna, and placing a second electrode of portable TES applicator on the subject (e.g., on the same ear, a different ear, or some other portion of the subject's head and/or neck); stimulating the vagus nerve by activating the TES applicator to deliver pulsed electrical stimulation between the first and second electrodes (e.g., at an intensity of 0.25 mA or greater, a duty cycle of greater than 10% and a frequency of greater than 250 Hz); and delivering the pulsed electrical stimulation between the first and second electrodes for a duration (e.g., a duration of 10 seconds or longer, 30 seconds or longer, 1 min or longer, 2 min or longer, 5 min or longer, etc.).

Any of these methods may include placing the portable transdermal electrical stimulation (TES) applicator so that the applicator is held in the ear by a friction fit.

In general, any of these methods may also include connecting the portable transdermal electrical stimulation (TES) applicator to a portable computing device worn or held by the subject via a cable. Alternatively or additionally the portable TES applicator may be wirelessly connected.

The user may adjust the delivered pulsed electrical stimulation, e.g., by manipulating a control on the portable TES applicator and/or by a portable computing device coupled to the portable TES applicator. Any of these methods may also include adjusting the delivered pulsed electrical stimulation from a portable computing device coupled to the portable transdermal electrical stimulation (TES) applicator.

Activating the portable TES applicator may include triggering activation of the portable TES applicator from a portable computing device held or worn by the subject. Activating may include delivering a pulsed electrical stimulation having a frequency of 10 Hz or greater. Activating may comprise delivering a pulsed electrical stimulation electrical stimulation having a frequency of 150 Hz or greater (e.g., 300 Hz or greater, 750 Hz or greater, etc.). Any of these methods may also include delivering a pulsed electrical stimulation waveform that is asymmetric, biphasic and transdermal.

Any of these methods may include activating the TES applicator to deliver the transdermal electrical stimulation having a duty cycle of greater than 10 percent.

In general, modifying the subject's cognitive state may comprise enhancing attention, alertness, or mental focus. Modifying the subject's cognitive state may comprise enhancing a calm or relaxed mental state. Specific examples of modifying the subject's cognitive state include, but are not limited to: enhance attention, alertness, or mental focus during skill training, such as in the learning of a computer language or foreign language, learning to use an autonomous vehicle or unmanned aerial vehicle (e.g., drone), learning proficiency on a weapon (e.g., marksmanship training), learning of information presented through digital media, such as streaming audio or video information from a tablet, phone, computer, screen, or across a network.

Placing the first electrode and the second electrode may include the subject wearing the first electrode and the second electrode on the pinna so that at least one of the electrodes is in contact with a cymba of the ear. The electrodes may be built into the portable TES applicator so that the positioning is automatic when the apparatus is placed in or on (over) the ear.

Any of these methods may include varying the applied transdermal electrical stimulation while the biphasic transdermal stimulation is applied. Any of these methods may include ramping the transdermal electrical stimulation during the application by decreasing one or more of the intensity, frequency, or duty cycle and then increasing one or more of the intensity, frequency, or duty cycle. In any of these variations, the electrical stimulation waveform may be biphasic.

In any of these variations, modifying the subject's cognitive state may include applying the transdermal electrical stimulation between the first and second electrodes for 15 minutes or longer.

In any of these variations, the electrical stimulation may be paired (including coordinated) with an audible signal. The audible signal (e.g., music, spoken words, nature sounds, etc.) may be provided to the subject from the TES applicator. For example, delivering the audio output may include delivering music. Delivering audio output may comprise delivering audio output concurrent with delivery of the pulsed electrical stimulation. Any of these methods may include delivering an audio output to the subject from the TES applicator wherein the TES applicator is configured as an earbud TES applicator comprising a speaker.

Also described herein are methods of modifying a subject's cognitive state (e.g., to induce or enhance attention, alertness, or mental focus or to induce or enhance a calm or relaxed mental state) by applying TES to the subject's ear (pinna). For example, a method of modifying a subject's cognitive state may include: placing a first and second electrode of a portable transdermal electrical stimulation (TES) applicator on the skin of the subject's pinna; activating the TES applicator to deliver a transdermal electrical stimulation having a frequency of 250 Hz or greater and a peak intensity of 0.25 mA or greater; and modifying the subject's cognitive state by applying the biphasic transdermal electrical stimulation between the first and second electrodes for 10 seconds or longer. In variations, the pinna electrodes may be either bilateral with unipolar electrodes on each pinna or unilateral with at least two (bipolar) electrodes on one pinna. In some variations, the electrical stimulation waveform may be asymmetric and biphasic.

Thus, a method of modifying a subject's cognitive state to induce or enhance attention, alertness, or mental focus or to induce or enhance a calm or relaxed mental state, may include: activating a portable transdermal electrical stimulation (TES) applicator to deliver a pulsed transdermal electrical stimulation having a frequency of 250 Hz or greater and an intensity of greater than 0.25 mA between a first and second electrode positioned on the subject's pinna so that at least one of the first and second electrodes are in contact with the subject's cymba; and modifying the subject's cognitive state by applying the biphasic transdermal electrical stimulation between the first and second electrodes for 10 seconds or longer. In some variations the electrodes may be positioned bilaterally with unipolar electrodes or unilateral with a bipolar electrode. In some variations, the electrical stimulation waveform may be asymmetric and biphasic.

Activating may include activating the TES applicator to deliver the transdermal electrical stimulation having a duty cycle of greater than 10 percent. Modifying the subject's cognitive state may be experienced as a change in physiology and may comprise enhancing attention, alertness, or mental focus, and/or enhancing a calm or relaxed mental state.

In general, modifying the subject's cognitive state and/or physiology may be mediated through the vagal nerve and affect one or more organ system, including but not limited to the gastric, intestinal, renal, hepatic, pulmonary, cardiac, circulatory, immunological, and nervous systems. Accordingly, transdermal stimulation of auricular vagal nerve branches with the systems and methods described herein may be applied for the treatment or diagnosis of various medical conditions, including but not limited to: alcohol addiction, Alzheimer's disease, anaphylaxis, anxiety disorders, apnea, atrial fibrillation, autism spectrum disorders, bulimia nervosa, burn-induced organ dysfunction, chronic heart failure, chronic intractable hiccups, comorbid personality disorders, concussion and post-concussive syndrome, coronary artery disease, Dravet syndrome, drop-attacks, eating disorders, epilepsy, fibromyalgia, genital self-stimulation after complete spinal cord injury, heatstroke, immune disorders, intestinal epithelial barrier breakdown, Lennox-Gastaut syndrome, memory disorders, migraines, minimally conscious or persistently vegetative states, mood disorders, myocarditis, multiple sclerosis, obsessive compulsive disorder, peripheral arterial occlusion disease, obesity, psychiatric disorders, Rasmussen's encephalitis, sepsis, sleep disorders, tinnitus, transient focal cerebral ischemia, trauma-hemorrhagic shock, and traumatic brain injury.

In some variations, placing the first electrode and the second electrode may comprise the subject wearing the first electrode and the second electrode on the pinna so that at least one of the electrodes is in contact with a cymba of the ear.

Placing the first electrode and the second electrode may comprise the subject wearing the first electrode and the second electrode unilaterally on one pinna so that at least one of the electrodes is in contact with a cymba of the ear.

Placing the first electrode and the second electrode may comprise the subject wearing the first electrode and the second electrode bilaterally on both pinnae so that at least one of the electrodes is in contact with a cymba of the ear. In variations, placing the second electrode may comprise unfurling or otherwise extending a conductive wire or cable between the first electrode (and, optionally, any housing or assembly connected thereto that may contain all or some of the components of the TES control apparatus) and the second electrode (and, optionally, any housing or assembly connected thereto that may contain all or some of the components of the TES control apparatus).

Activating the portable TES applicator may include triggering activation of the portable TES applicator and/or triggering activation of the portable TES applicator from a handheld device wirelessly or via a wired connection (e.g. via a one, two, or three channel headphone jack or via a multi-pin communication and power exchange connector such as a lightning connector on an iPhone 6).

Activating the portable TES applicator may include triggering activation of the portable TES applicator by a voice command, by pressing a button or other user interface on the portable TES applicator, by sending a control signal via an application interface on a user computing device configured to control the TES applicator in a wired or wireless (e.g. Bluetooth Low Energy) fashion, or automatically as soon as skin contact of the two or more electrodes is detected (i.e. an electrode impedance below a threshold value is measured, indicating dermal placement).

Any of the methods described herein may also include varying the applied transdermal electrical stimulation while the transdermal stimulation is applied to apply neurostimulation using ensemble waveforms. In general, an ensemble waveform typically includes a series or ordered set of waveform parameters, where the set of waveform parameters may specify peak current amplitude (also referred to as peak current intensity, and which in general may refer to the peak positive-going current intensity and/or the peak negative-going current intensity), frequency, duty cycle, percent charge imbalance, and optionally, capacitive discharge state. Each set may also include a time specifying the duration that these waveform parameters are valid, and in some variations, a ramping value indicating the value that the parameter is ramped over and, optionally, the pattern of ramping (i.e., linear, step-wise linear, exponential, etc.). The set of these waveform parameters, duration, and ramping values may together define a stimulation protocol having a plurality of different waveform parameters that are arranged sequentially. For example, an ensemble waveform may include a series of 3 or more (e.g., 4 or more, 5 or more, 6 or more, 7 or more, 8 or more, 9 or more, 10 or more, etc.) component waveforms, wherein component waveforms are typically biphasic and each has a duration and a predefined set of waveform parameters including a frequency, an intensity, a duty cycle and a percent charge imbalance, wherein at least one of the waveform parameters of each component waveform is different from the waveform parameters of a component waveform preceding it, following it, or preceding and following it in the series. Each component waveform may also include a ramping time or ramping indicator, indicating that any waveform parameter that changes from a preceding component waveform parameter is to be ramped to the new value over the duration of the component waveform (or over the duration of the ramping time in some variations). Functionally, a waveform ensemble may be created to evoke a particular cognitive effect, such as relaxation, calmness, energy, etc. A waveform ensemble may also be created to be comfortable and effective with a particular neurostimulator device and electrodes. Examples of waveform ensembles are described herein.

Any of these methods may also include ramping the transdermal electrical stimulation during the application by decreasing one or more of the intensity, frequency, duty cycle, charge imbalance, bursting frequency, or bursting duty cycle and then increasing one or more of the intensity, frequency, duty cycle, charge imbalance, bursting frequency, or bursting duty cycle. In any of these methods, the electrical stimulation waveform may also be biphasic and may be asymmetric.

In general, the portable TES applicator may be worn on or in the ear. In variations, the TES applicator may comprise one or more housings on or in only one ear. In alternative variations, the TES applicator may comprise one or more housings on or in both ears, connected by a wire or cable (which may incorporate inline electronic components such as a battery, microcontroller, current source, safety circuitry, etc. in one or more housing) so that the assemblies worn on or in an ear are smaller for improved fit, comfort, and discreteness.

In variations, the TES applicator worn on or in one or both ears may be standalone and contain a power source, a current source, microcontroller, safety circuitry, etc. In other variations, the TES applicator worn on or in one or both ears may be wired and connected to a portable TES controller (e.g. user computing device such as a smartphone or tablet; or a dedicated portable electronic apparatus), or the TES applicator worn on or in one or both ears may be in wireless communication with a portable TES controller.

Modifying the subject's cognitive state may comprise applying the biphasic transdermal electrical stimulation between the first and second electrodes for 30 seconds or longer, (e.g. 1 minute or longer, 2 minutes or longer, 3 minutes or longer, 4 minutes or longer, 5 minutes or longer, 6 minutes or longer, 7 minutes or longer, 8 minutes or longer, 9 minutes or longer, 10 minutes or longer, 11 minutes or longer, 12 minutes or longer, 13 minutes or longer, 14 minutes or longer, 15 minutes or longer, 16 minutes or longer, 17 minutes or longer, 18 minutes or longer, 19 minutes or longer, 20 minutes or longer, 25 minutes or longer, 30 minutes or longer, etc.).

An advantage of the ear-based TES systems and methods described herein may include concurrent electrical stimulation and an audible signal (e.g., which may be transduced by air or via bone conduction). Novel cognitive effects may be induced by aligning in time (in some cases, with a temporal offset) an auricular TES waveform with an audible signal through coordinated activation of auditory pathways with cranial and/or cervical spinal nerve downstream pathways. For example, any of these methods may include delivering an audible signal to the subject from the TES applicator. Any audible signal may be used, including one or more of: a song (e.g., music), a tone or tones, a chant, spoken language, instrumental music, white noise, structured noise (e.g. pink noise, brown noise, frequency-modulated noise), binaural beats, recorded or synthesized sounds (e.g. ocean noise, wind noise, running water, etc.), or the like. In variations, the audible signals may take the form of instructions or advisements about the TES applicator (e.g. 'recharge device', 'one minute remaining', 'adjust intensity for optimal experience', etc.); may take the form of music, chants, recorded sounds, and/or synthesized sounds timed and temporally sequenced to match, enhance, or otherwise modulate the cognitive effects induced from auricular TES alone; or may take the form of binaural beats in bilateral variations of the system (i.e. higher frequency audible signals (generally frequencies above 200 Hz)) with phase offsets at frequencies of brain rhythms (generally frequencies less than 200 Hz).

For example, any of these methods may include delivering an audible signal to the subject from the TES applicator wherein the audible signal is delivered from an earbud TES applicator.

Also described herein are wearable pinna transdermal electrical stimulation (TES) applicators for modifying a subject's cognitive state by applying TES to the subject's pinna. For example a wearable pinna TES (e.g., PENS) apparatus may include: a first body adapted to be worn in a pinna region of a first ear; a second body adapted to be worn in a pinna region of a second ear; a first electrode on the first body; a second electrode on the second body; and a wearable TES controller coupled to the first and second bodies and comprising a power source, a processor, a timer, and a waveform generator, wherein the TES controller is adapted to deliver an electrical stimulation signal of 10 seconds or longer between the first and second electrodes having a peak intensity of greater than 0.25 mA.

A wearable pinna transdermal electrical stimulation (TES) applicator for modifying a subject's cognitive state by applying TES to the subject's pinna may include: a body adapted to be worn by the subject in the subject's ear; a first electrode coupled to the body and configured to be worn in a pinna region of the subject's ear; a second electrode coupled to the body; and a wearable TES controller coupled to the first and second bodies and comprising a power source, a processor, a timer, and a waveform generator, wherein the TES controller is adapted to deliver an electrical stimulation signal of 10 seconds or longer between the first and second electrodes having a peak intensity of 0.25 mA or greater, a duty cycle of greater than 10% and a frequency of greater than 250 Hz.

A wearable pinna transdermal electrical stimulation (TES) applicator for modifying a subject's cognitive state by applying TES to the subject's pinna may include a first body adapted to be worn in a pinna region of a first ear; a second body adapted to be worn in a pinna region of a second ear; a first electrode removably attached to the first body; a second electrode removably attached to the second body; and a wearable TES controller coupled to the first and second bodies and comprising a power source, a processor, a timer, and a waveform generator, wherein the TES controller is adapted to deliver an electrical stimulation signal of 10 seconds or longer between the first and second electrodes having a peak intensity of greater than 0.25 mA.

For example a wearable ear-attaching TES apparatus may include: a body adapted to be worn by the subject; a first electrode comprising a core conductive layer covered by a conductive polymer layer; a second electrode comprising a core conductive layer covered by a conductive polymer layer; a TES control module (controller) comprising a power source, a processor, a timer, and a waveform generator, wherein the TES controller is adapted to deliver an electrical stimulation signal of 10 seconds or longer between the first and second electrodes having a frequency of between 10 Hz and 50 kHz (e.g., between 100 Hz and 1 kHz; between 3 kHz and 50 kHz, etc.) a duty cycle of between 10 and 80 percent, a peak intensity of at least 0.25 mA; and (optionally) a wireless receiver connected to the TES controller. Any of the electrodes described herein may be formed of multiple layers, as will be described in greater detail below, including a carbon black layer, and other layers.

The first electrode may be on an outer surface of a wearable applicator and configured to deliver TES from the TES controller to the subject's pinna. In some variation the second electrode and the first electrode may be on separate applicators, for example where each applicator is configured to connect to a separate ear (e.g., allowing TES between the ears/across the wearer's head) and connected by a cable, wire, or other contoured or flexible assembly containing a conductive element; alternatively in some variations the first and second electrode are on the same applicator that connects to the same ear.

Either the first electrode, the second electrode, or both may be coupled to the body by a cord. Either or both the first and second electrode may be part (e.g., a component) of a removable electroconductive earbud attachment of the wearable applicator.

Any of these apparatuses may include an adhesive on the body of the apparatus to secure the body to the subject's skin (including, but not limited to, the ear). Alternatively or additionally, the apparatus may be secured to the ear(s) and to the user's skin, garment, or not secured, but held by the user (including in the user's pocket).

The power source may be at least one battery, and may be rechargeable or reusable or single-use.

Any of these apparatuses may include a manual control on the body coupled to the controller (e.g., knob, touchscreen, switch, button, slider, etc.).

Any of these apparatuses may include voice activation functionality.

Any of these apparatuses may commence electrical stimulation automatically as soon as skin contact of the two or more electrodes is detected (i.e. an electrode impedance below a threshold value is measured, indicating dermal placement).

Any of these apparatuses may include a wireless communication system (i.e. antenna, chipset, etc.) so that the TES applicator may be controlled by a user computing device (i.e. an app stored in a machine-readable memory on the user computing device).

Any of these apparatuses may connect by a wired connection to a user computing device. The one or more TES applicators may connect via a one, two, or three channel headphone jack or via a multi-pin communication and power exchange connector such as a lightning connector on an iPhone 6. Connecting by a wired connection to a user computing device may reduce the size, complexity, and cost of a TES applicator by reducing required components. For example, power for the TES applicator may be supplied by the user computing device instead of having a battery and related circuitry on the TES applicator—or the microcontroller needs of the TES applicator may be reduced by offloading some or all of the processing to the user computing device.

Any of these apparatuses may include a capacitive discharge circuit, wherein the TES controller is configured to occasionally trigger the capacitive discharge circuit to discharge capacitance on the electrodes during the delivery of the biphasic electrical stimulation. Any of these apparatuses may alternatively or additionally include a current limiter. Any of these apparatuses may also include a memory connected to the TES controller and adapted to store information on the operation of the TES applicator.

The first and/or second electrodes may be on an outer surface of a wearable applicator and configured to deliver TES from the TES controller to the subject's pinna and wherein the wearable applicator is in contact with at least one region of the wearer's pinna. A region of the wearable applicator may be covered with a malleable and conductive material for contacting a region of the subject's pinna. A region of the first electrode may be covered with a malleable and conductive material for contacting a region of the subject's pinna. A region of the second electrode may be covered with a malleable and conductive material for contacting a region of the subject's pinna. The malleable and conductive material may comprise a conductive polymer, such as (but not limited to): conductive foam, conductive silicone, or conductive rubber.

In any of the apparatuses described herein, an electrode may comprise conductive silicone tubing (e.g. about 3 mm or smaller in diameter having about 40 Ohms/cm resistance) with a metal wire contained in its center to provide uniform current distribution along the tubing as well as structural integrity so that the wire-tubing electrode assembly conforms to individual concha anatomy for comfortable fit. In variations of this electrode apparatus, a resistive layer may be coated at positions along the length of the core conductive wire to permit control of current distribution spatially.

The first and/or second electrodes may be integrated with a first and/or second wearable applicator.

As mentioned, any of the wearable applicators described herein may include a speaker configured to deliver an auditory signal. The first and/or second electrode may be coupleable and/or uncoupleable from the wearable applicator (e.g., may be removeably attached so that they can be repeatedly attached on, then removed from the applicator).

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1 is an illustration of a human pinna indicating the approximate positions of various cranial and cervical spinal nerve branches.

FIG. 2 is an anatomical illustration of a human pinna.

FIG. 7A is an example showing a first potential variation of the transdermal electrical stimulation waveform with varied amplitudes for positive and negative peak currents and period cycle length compared to the waveform shown in FIG. 6.

FIG. 7B is an example showing a second potential variation of the transdermal electrical stimulation waveform with a sharp negative peak form (e.g., from applied capacitive discharge current after the first, positive-going, pulse of this unit waveform).

FIG. 7C is an example showing a third potential variation of the transdermal electrical stimulation waveform with a sharp positive peak form (e.g., from applied capacitive discharge current after the second, negative-going, pulse of this unit waveform).

FIG. 7D is an example showing a fourth potential variation of the transdermal electrical stimulation waveform with both a sharp positive and a sharp negative peak form (e.g., from applied capacitive discharge current after both the positive- and negative-going pulses of this unit waveform).

FIG. 17 is a schematic illustrating a pinna module such as the one shown in FIG. 16 within a wearer's ear.

FIG. 18 is schematic illustrating the wearer-facing side of another variation of a pinna electrical nerve stimulation system where the pinna electrical nerve stimulation electrode is integrated with a pair of earbud headphones.

FIG. 22D illustrates another example (not to scale) of a section view though an active region of an electrode fed by a conductive trace; in this example, the active region includes a weakly insulating layer (e.g., a thin carbon layer between the silver and silver chloride layers). FIG. 22E shows a section view though an active region directly connected to a (snap) connector for coupling to a neurostimulator and including a weakly insulating layer (e.g., carbon); FIG. 22F is a slightly enlarged view of FIG. 22E.

FIGS. 27A-27C show schematic representations of a TES apparatus having two modules connected by a durable cable that can be disconnected.

FIG. 30A is an example of a smart cable (TES cable neurostimulator) for use with an electrode assembly to be worn on the subject. The TES cable neurostimulator may connect (and receive power and control instructions) from a portable computing device such as a smartphone, and also connect directly to the connectors (e.g., snap connectors are shown) of an electrode assembly. The cable may be reused with multiple disposable (single-use or limited-use) electrode assemblies.

FIG. 30B illustrates another example of distal end of a TES cable neurostimulator having a pair of connectors that may be independently connected to an electrode assembly.

DETAILED DESCRIPTION

Figure 3:
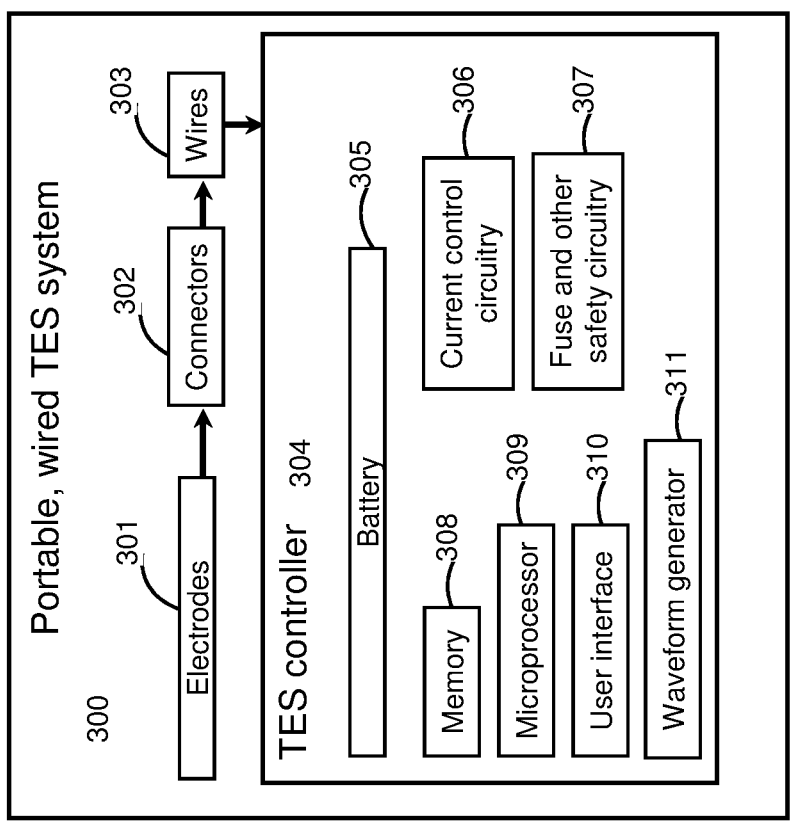
FIG. 3 is a diagram of the components of a portable, wired pinna TES neurostimulator system.

In general, described herein are pinna electrical nerve stimulation (PENS) apparatuses (devices and systems) that may generally be used to apply transdermal electrical stimulation (TES) through at least one electrode in contact with a portion of the subject's pinna (e.g., outer ear). These apparatuses may be configured to be worn on the outer ear and may include a controller that is adapted to deliver electrical waveforms (TES doses) within a predetermined range of values that have been identified as effective for modulating a subject's cognitive state to induce or enhance a particular cognitive state, without resulting in pain or undue discomfort. Modulation of a subject's cognitive state may comprise a physiological change.

As used herein, the term "pinna" typically refers to the external part of the ear in humans and other mammals. A "subject" may refer to a user, wearer, person, patient, etc. Subjects may be human or non-human mammals.

Examples of the general components and principles of pinna electrical nerve stimulation devices are described herein in the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, a variety of pinna electrical nerve stimulation device examples are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

Transdermal electrical stimulation (TES) of the pinna is a beneficial strategy for targeting cranial nerves. The pinna generally has little or no hair, so stimulating electrodes can make relatively uniform, low impedance contact. Also, branches of several cranial and cervical spinal nerves are present in a compact area, permitting forms of neuromodulation not possible by stimulating other areas of the body (i.e. head) where cranial and/or cervical nerve branches may be spaced more broadly or covered in hair.

The innervation of the pinna forms the basis of auriculotherapy and ear acupuncture techniques, which are designed to improve mood, relieve pain, promote relaxation, reduce stress, and treat substance abuse disorders or neuropsychiatric diseases. Improved TES of the pinna could provide great benefit for the treatment and diagnosis of a variety of cognitive and non-cognitive disorders. Neuromodulation in healthy subjects to induce cognitive effects would be another beneficial application of TES of the pinna.

The innervation of the pinna and external ear is achieved by several nerves including branches of cranial nerves V (trigeminal), VII (facial), and X (vagus), as well as the greater auricular nerve and auriculo-temporal nerve, which are branches of the cervical plexus (spinal nerves C2 and C3). These nerves carry motor signals and sensory signals from and to the brain, respectively. Several of these nerves provide communication between the external world and key arousal regions of the brainstem including the reticular nucleus, locus coeruleus, and nucleus of the solitary tract. Systems for stimulation of nerves of the pinna would be advantageous for inducing reliable forms of neuromodulation to induce beneficial cognitive effects that may in at least some cases be associated with physiological changes in the user or patient. Both lifestyle applications and therapeutic treatments are possible with the PENS systems and methods described herein.

FIG. 1 shows locations of innervation for the vagus nerve with triangles (localized largely to the concha) and facial nerve with circles, as well as innervation by the auriculotemporal branch of the mandibular nerve in the area outlined by rectangle 101 and the cervical nerves (outside of the area inside of rectangle 101). FIG. 2 shows anatomy of the pinna.

Any of the methods or devices described herein may include electrically contacting the subject's skin at any location on one or both pinnae, including in particular one or more of those illustrated in FIGS. 1 and 2. Thus, any of the apparatuses described herein may be configured to electrically connect to the pinna in a region at or near one or more of the locations/regions shown in FIGS. 1 and/or 2. Similarly, any of these methods may be configured to position an electrode (or electrodes) at one or more of these locations/regions and/or apply TES at one or more of these locations/regions.

The PENS apparatuses described herein typically include electrodes, e.g., a first electrode and a second electrode, wherein at least one electrode is configured to attach to the pinna, as well as a controller including a signal generator to generate the waveforms to be delivered to the subject by the electrodes. The controller generally includes circuitry to generate and deliver these waveforms. These apparatuses may also be referred to herein as neurostimulators or PENS neurostimulators.

The neurostimulator may be capable of autonomous function and/or controllable in a wired or wireless manner by a computerized user device (e.g. smartphone, tablet, laptop, smartwatch, other wearable device). The neurostimulator is configured specifically to deliver stimulation within a range of parameters, including intensity and frequency, determined to be effective for inducing, enhancing, or promoting (collectively, "modifying") a desired cognitive state and/or effect (also including predominantly non-cognitive physiological effects) while minimizing pain and discomfort due to the relatively large magnitude stimulation provided. For example, an apparatus (such as an applicator) may include a controller having circuitry (e.g., hardware), software, and/or firmware that allows the apparatus to apply signals within an effective range, including, for example, one or more processors, timers, and waveform generators.

Relative to existing systems for transdermal electrical stimulation of the ear (e.g., pinna), the systems and methods described herein induce more powerful cognitive effects for treatment, diagnosis, and/or lifestyle (i.e. not for treatment of diagnosis of any medical condition) applications. In some examples described herein, by using replaceable, disposable (e.g., consumable, pH buffering) electrodes and appropriate electrical stimulation parameters, discomfort from the relatively sensitive skin of the pinna can be mitigated, enabling higher peak currents to be delivered for stimulating pinna nerves.

Nerve branches in the pinna may be targeted broadly (e.g., branches of more than one cranial and/or cervical spinal nerve) or specifically. The specificity of which single cranial nerve, single cervical spinal nerve, or set of cranial and/or cervical spinal nerve branches is stimulated can be achieved by the placement of two or more electrodes; by the stimulation parameters selected (e.g., frequency, duty cycle, peak intensity, percent charge imbalance, bursting parameters (e.g., frequency and duty cycle), and presence or absence of capacitive discharge); or by both electrode placement and stimulation parameters.

Beneficial aspects of the systems and methods for pinna stimulation described here include: (1) miniaturized and wearable neuromodulation devices configured to deliver electrical stimulation waveforms that are sufficiently comfortable and effective for inducing a cognitive effect by stimulation of one or more cranial and/or cervical spinal nerves in the pinna (The devices may include wireless and battery-powered form factors controlled by a remote controller that may be a smartphone, tablet, or other connected wearable device; fully autonomous battery-powered form factors that fit on or in an ear and do not require any external controller or user interface; and form factors that connect to a portable user computing device (e.g. smartphone, tablet, smartwatch, etc.) via a cable for transmission of control signals and/or power from the battery of the user computing device); (2) structural, mechanical, and electrode systems for placement of dermal electrodes targeting one or more cranial and/or cervical spinal nerves in the pinna; (3) replaceable and/or consumable (i.e. disposable or semi-disposable) dermal electrodes, including those that buffer pH for charge imbalanced waveforms; and (4) ensemble waveforms (including intermittent waveforms, i.e. those having a low frequency (<1 Hz) bursting frequency) and/or waveforms comprising a capacitive discharge pulse to improve the efficacy of stimulation.

In general, the devices described herein include a wearable neurostimulator to deliver TES via two or more electrodes in contact with the dermis of one or both pinna to target one or more cranial and/or cervical spinal nerves. The devices and systems described herein may also include assemblies configured to couple electrodes to appropriate locations in the pinna for targeting one or more cranial and/or cervical spinal nerves. The devices and systems described may also include replaceable and/or disposable (i.e. consumable) dermal electrodes configured to reduce skin irritation and provide a sufficiently uniform and low impedance connection (and, in some embodiments, consumptive pH buffering electrochemistry) to the skin of the pinna for comfortable and efficacious pinna TES.

Exemplary TES Systems

FIG. 3 shows one example of a schematic 300 for a portable, wearable TES neurostimulator configured to connect to subject's pinna. In this example, electrodes (which may include adhesive and/or structural components for contacting the skin of the pinna relatively uniformly) 301 connect to pinna TES controller 304 via connectors 302 and wires 303. Pinna TES controller 304 has several components including battery 305, fuse and other safety circuitry 307, memory 308, microprocessor 309, user interface 310, current control circuitry 306, and waveform generator 311. The adherent electrodes may be adapted specifically to attach to the pinna, as described herein. The electrodes are to be worn in contact with the subject (e.g., at least one of them in contact with at least a portion of the subject's pinna), and are connected via one or more wire, cable, flex circuit, connector, etc. to the TES controller 304. The electrodes may be part of an earplug/earbud type structure to be worn in and/or secured on the ear. Electrodes may therefore be adhered to the ears by mechanical connection (e.g., expandable foam, wires, structural components, including those with spring functionality for forming stable connections, etc.) and/or adhesive (e.g., biocompatible adhesive), or the like. The phrase adherent refers to the placement of the electrodes in electrical contact with the subject's skin and does not require an adhesive connection (e.g., sticking to the skin), and includes connections that are held to the skin by mechanical rather than adhesive means.

Figure 4:
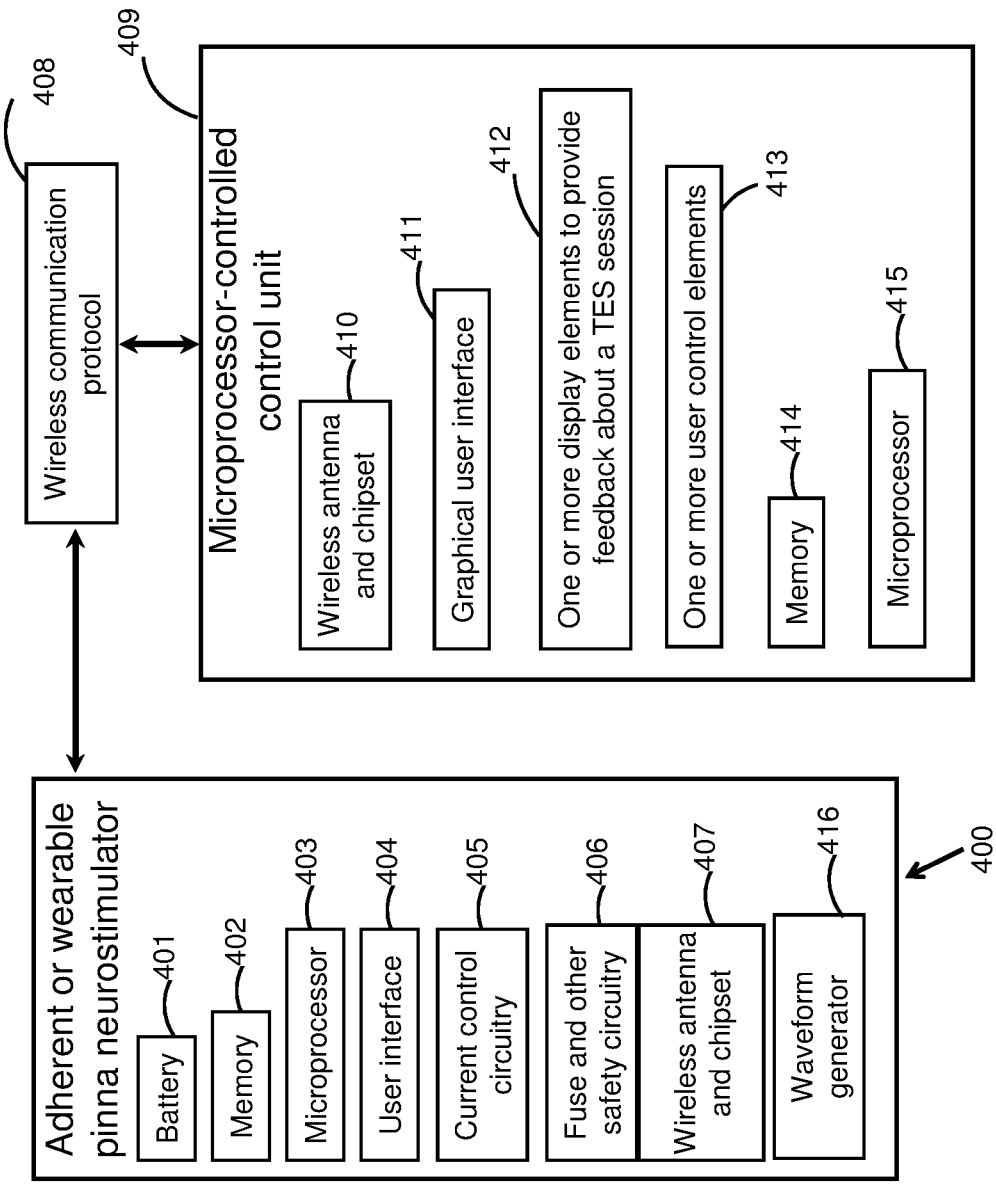
FIG. 4 is a diagram of components of a pinna TES neurostimulator system that connects wirelessly to a control unit comprising a microprocessor.

FIG. 4 shows another example of a pinna TES system comprising adherent or otherwise wearable pinna TES neurostimulator 400 that communicates wirelessly with microprocessor-controlled control unit 409 (e.g. a smartphone running an Android or iOS operating system such as an iPhone or Samsung Galaxy, a tablet such as an iPad, a personal computer including, but not limited to, laptops and desktop computers, or any other suitable computing device). In this exemplar embodiment, adherent or wearable pinna neurostimulator 400 holds two or more electrodes in dermal contact with a subject with an adhesive and/or a shaped form factor that fits on or is worn on a portion of a user's body (e.g., a headband or around-the-ear 'eyeglass' style form factor). In an exemplary embodiment, adherent or wearable pinna neurostimulator 400 comprises components: battery 401, memory 402, microprocessor 403, user interface 404, current control circuitry 405, fuse and other safety circuitry 406, wireless antenna and chipset 407, and waveform generator 416. Microprocessor-controlled control unit 409 includes components: wireless antenna and chipset 410, graphical user interface 411, one or more display elements to provide feedback about a pinna TES session 412, one or more user control elements 413, memory 414, and microprocessor 415. In an alternate embodiment the pinna neurostimulator 400 may include additional or fewer components. One of ordinary skill in the art would appreciate that neurostimulator could be comprised of a variety of components, and embodiments of the present invention are contemplated for use with any such component.

An adherent or wearable pinna neurostimulator 400 may be configured to communicate bidirectionally with wireless communication protocol 408 to microprocessor-controlled system 409. The system can be configured to communicate various forms of data wirelessly, including, but not limited to, trigger signals, control signals, safety alert signals, stimulation timing, stimulation duration, stimulation intensity, other aspects of stimulation protocol, electrode quality, electrode impedance, and battery levels. In other variations, the pinna neurostimulator may connect via a wired connection to a user computing device for bidirectional communication (including the above listed forms of data) and, optionally, power for the pinna neurostimulator apparatus (in which case the pinna neurostimulator apparatus may not require a battery or may function with a smaller power reservoir (e.g. smaller battery or capacitor(s)). Communication may be made with devices and controllers using methods known in the art, including but not limited to, RF, WIFI, WiMax, Bluetooth, BLE, UHF, NHF, GSM, CDMA, LAN, WAN, or another wireless protocol. Pulsed infrared light as transmitted for instance by a remote control is an additional wireless form of communication. Near Field Communication (NFC) is another useful technique for communicating with a neuromodulation system or neuromodulation puck. One of ordinary skill in the art would appreciate that there are numerous wireless communication protocols that could be utilized with embodiments of the present invention, and embodiments of the present invention are contemplated for use with any wireless communication protocol.

An adherent or wearable pinna neurostimulator 409 may but does not need to include user interface 404 and may be controlled exclusively through wireless communication protocol 408 (or wired communication) to control unit 409. In an alternate embodiment, adherent or wearable pinna neurostimulator 409 does not include wireless antenna and chipset 407 and is controlled exclusively through user interface 404 or wired connection to a user computing device. One skilled in the art will recognize that alternative pinna neurostimulator systems can be designed with multiple configurations while still being capable of delivering electrical stimulation transdermally into a subject.

Figure 5:
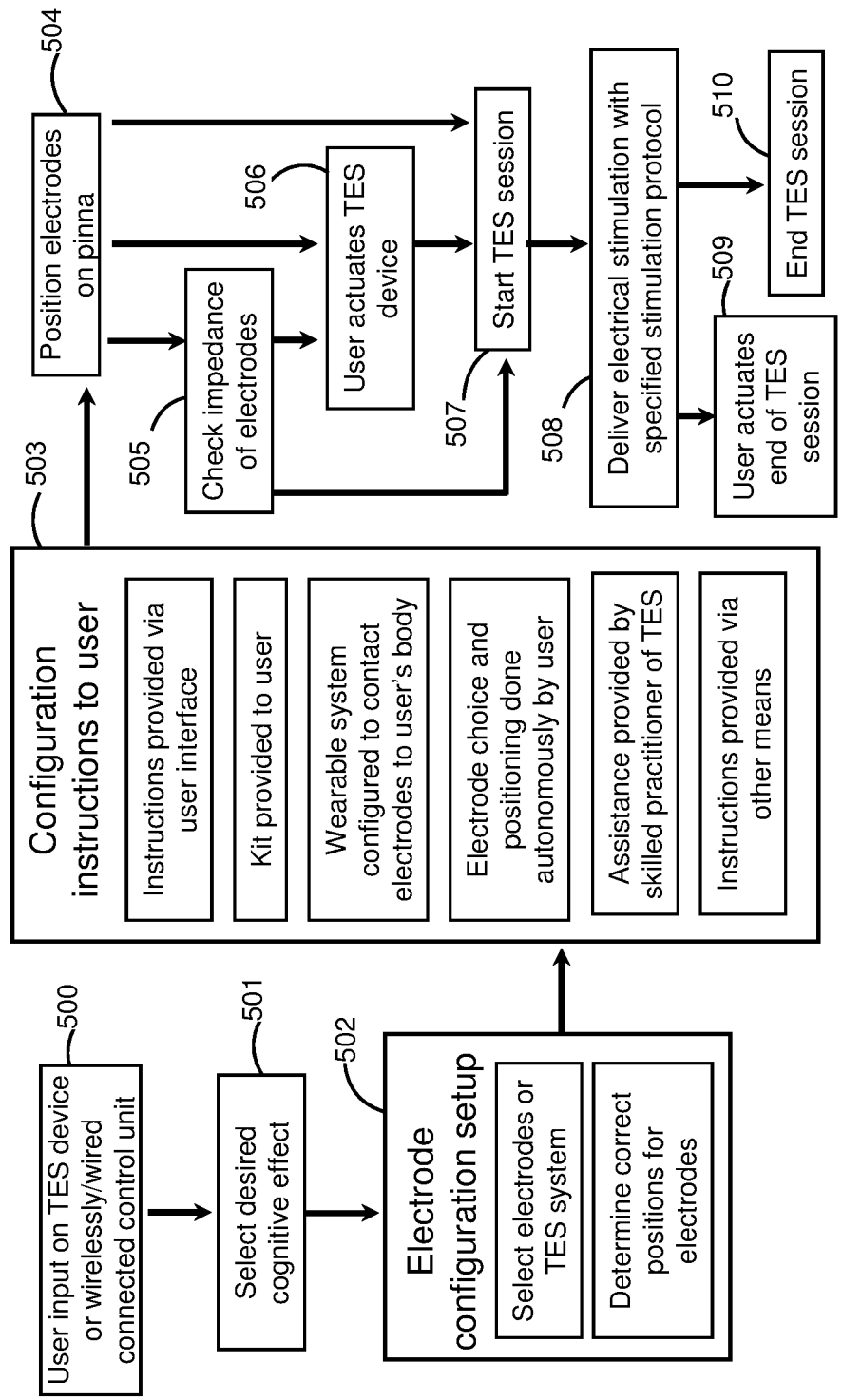
FIG. 5 is a diagram of a workflow for configuring, actuating, and ending a pinna TES session.

FIG. 5 shows an exemplary workflow for configuring, actuating, and ending a pinna TES session. According to an embodiment of the present invention, user input on pinna TES device or wirelessly/wired connected control unit 500 is used to select desired cognitive or physiological effect 501 which determines electrode configuration setup 502 to achieve the desired cognitive or physiological effect, including selection of electrodes or a pinna TES system that contains electrodes and determination of correct positions for electrodes. In an embodiment, configuration instructions to user 503 are provided by one or more ways selected from the list including but not limited to: instructions provided via user interface; kit provided to user; wearable system configured to contact pinna TES electrodes to appropriate portions of a user's pinna; electrode choice and positioning done autonomously by user (e.g. due to previous experience with pinna TES); assistance provided by skilled practitioner of pinna TES; and instructions provided via other means.

Based on these instructions or knowledge, a user or other individual or system positions electrodes on pinna 504. In some embodiments, the pinna TES session starts 507 automatically after electrodes are positioned on the pinna. In other embodiments, the impedance of the electrodes 505 is checked by a pinna TES system before the pinna TES session starts 507. In some embodiments, after impedance of the electrodes 505 is checked by a pinna TES system, user actuates pinna TES device 506 before the pinna TES session starts 507. In other embodiments, after positioning electrodes on the body 504 the user actuates the pinna TES device 506 to start the pinna TES session 507. Once the pinna TES session starts, the next step is to deliver electrical stimulation with specified stimulation protocol 508. In some embodiments, a user actuates end of pinna TES session 509. In other embodiments, the pinna TES session ends automatically when the stimulation protocol completes the pinna TES session 510.

In general, the apparatuses described herein may be neuromodulation devices for pinna TES. For example, miniaturized and wearable neuromodulation devices for pinna TES may generally be lightweight and fit on or in one or both ears. Dermal pinna electrodes connected to the neuromodulation device transmit electrical stimulation waveforms generated by the neuromodulation device in order to modulate the activity of one or more cranial and/or cervical spinal nerves. These neuromodulation devices may also be referred to as neurostimulation devices, neurostimulators, neuromodulators, applicators, neuromodulation applicators, electrical stimulators, or the like.

The TES controller may be wearable on (i.e. around) the ear or within the conch of the ear. Alternatively, the TES controller may be connected by a wire to the housing that places the two or more electrodes on the skin of the pinna and worn either elsewhere on the body, held by the user, or carried in a bag, pocket, or other suitable enclosure for a portable device (e.g. a user computing device such as a smartphone or dedicated hardware). Hardware devices that fit over the ear may be discreet and may rely on the ear itself for structural support to hold the device. Hardware devices that mount within the conch of the ear can use that structure to support and/or hold a miniaturized device, similar to how an earbud headphone is secured in the ear for providing auditory signals.

In some embodiments, the electrode apparatus may include an attachment (such as a mechanical and/or adhesive attachment) configured to couple the electrode apparatus to a pinna of a user or any other device or system. For example, an attachment portion of an electrode apparatus may include an adhesive component that may surround and/or be adjacent to the boundary of a consumptive layer of the electrode. Alternatively, a structural component (e.g. firm and shaped or containing a spring component to hold one or more electrodes in firm contact with the targeted area of the pinna (i.e. concha).

Figure 10:
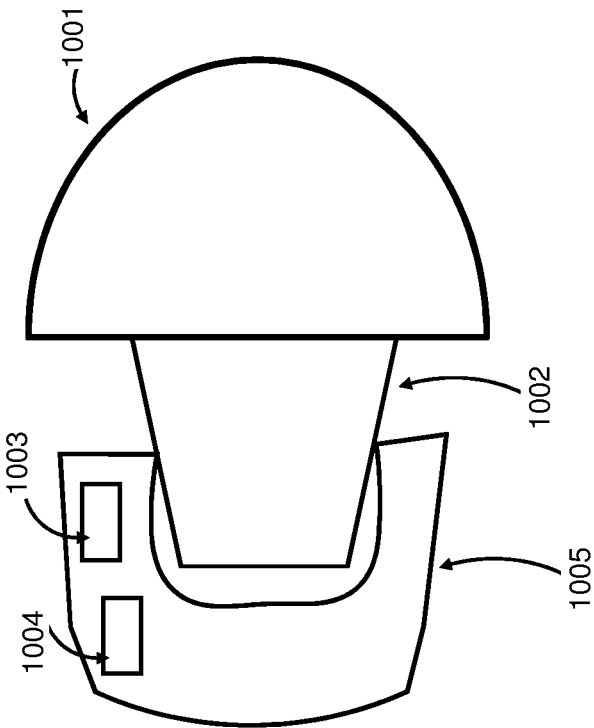
FIG. 10 is a schematic illustrating a wireless earbud-style wearable neurostimulator with an electro-conductive attachment for placement within the meatus, as described herein.

In some embodiments, the PENS apparatus includes a wearable applicator that is configured to connect to at least a portion of a pinna so that the electrode(s) can be in electrical contact with a skin region of the pinna. For example, the apparatus may include a wearable applicator portion that is a soft, conformable attachment to (or configured as) an earbud neurostimulator that has one or more electroconductive polymer (or electroconductive rubber, etc.) attachments that provide improved comfort and fit of the neurostimulator earbud, while also delivering electrical stimulation to the pinna. By securing the earbud neurostimulator in the ear canal, the electroconductive polymer attachment can also form a secure connection for providing auditory stimulation (e.g. music) via a speaker element of the neurostimulator. Conductive electrode attachments to an earbud neurostimulator can be replaceable and consumable, as well as sized and shaped for different ear shapes, and different shapes to target different cranial and cervical spinal nerves as desired for a cognitive effect such as modulation of psychophysiological arousal. FIG. 10 illustrates an earbud-style pinna TES neurostimulator 1001 with a conformable attachment 1005 that may be an electroconductive polymer and improve the fit of the unit within the external auditory meatus of the pinna. Device portion 1002 is configured to sit within the external auditory meatus or portion 1001 is configured to project beyond the pinna when being worn. Electroconductive polymer component 1005 may be insulated except in specific active electrode areas 1003 and 1004 placed at appropriate locations and may be consumable, replaceable and intended for use once or a limited plurality of times.

Figure 9:
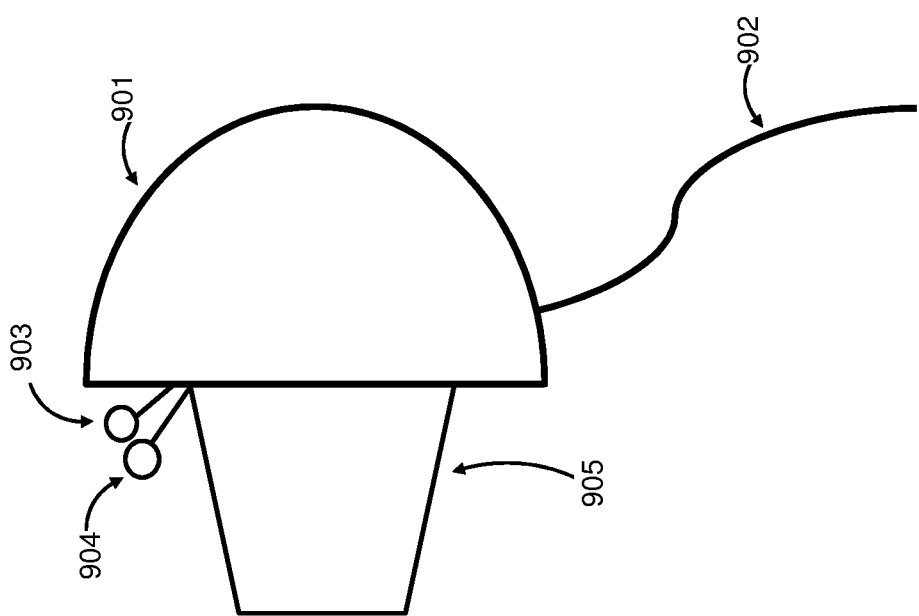
FIG. 9 is a schematic illustrating an earbud-style wearable neurostimulator with ball electrodes for dermal stimulation of the pinna, as described herein.

In another embodiment, one or more ball electrodes (e.g. 903, 904) may be attached to an earbud embodiment designed to be worn in the conch of the ear. Ball electrodes have a conductive portion (e.g. sphere) at an end distal from the neurostimulator, connected by an insulated conductive wire, cable, or other structural component. In one embodiment, an earbud fits into the meatus for providing auditory stimulation such as music while ball electrodes extend from the headphone to make contact with the cymba, triangular fossa, and/or intertragal notch. One advantage of ball electrodes is the robustness to different curvatures as are present within and between pinnae. In this manner, a spherical, ovoid, or other rounded shape may be pressed at any angle and at any portion of the pinna (regardless of the curvature of that region of the pinna) and still maintain a conductive path for stimulation. FIG. 9 illustrates an earbud-style pinna TES neurostimulator with dermal ball electrodes 903, 904 for stimulating the pinna. Preferably, the conductive and insulated structures that couple the ball electrodes to the neurostimulator device (either the portion 905 configured to sit within the external auditory meatus or portion 901 that project beyond the pinna) can be flexibly rotated yet stably held in place once moved into position for pinna stimulation. The pinna TES neurostimulator may be wired 902 and connected to a controller, power source, mobile computing device, etc. Alternatively, the device may have no wires and be controlled autonomously by user interfaces of the wearable device (i.e. a button), by voice commands, or in a wired or wireless manner from a user computing device (smartphone, tablet, laptop, desktop, wearable computer, etc.)

Figure 12:
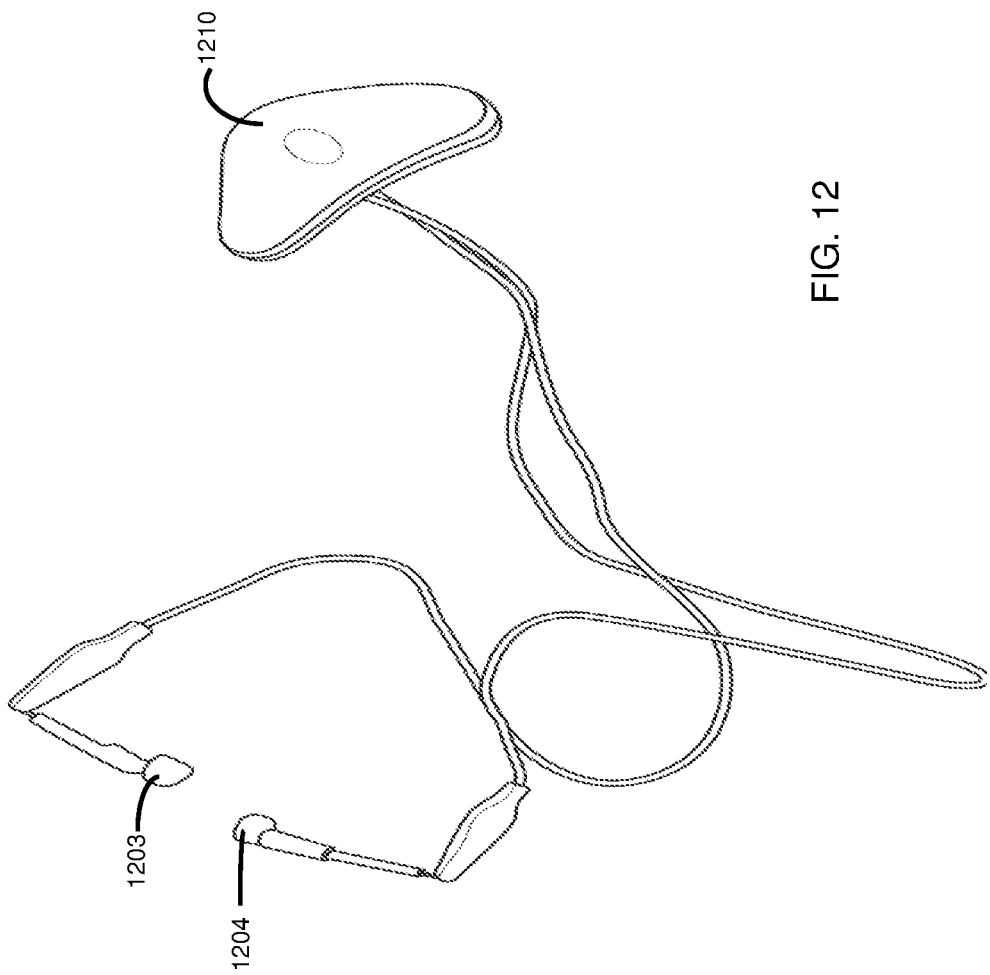
FIG. 12 is a schematic illustrating a TES waveform generator in physical connection with a pair of pinna electrical nerve stimulation (PENS) electrodes.
Figure 11:
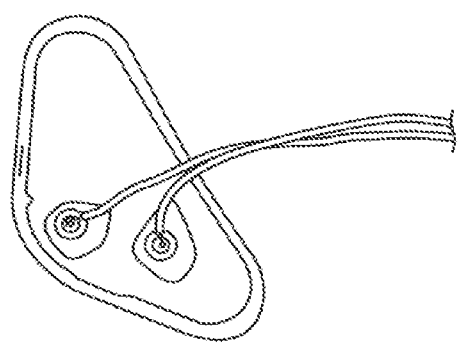
FIG. 11 is a schematic illustrating a series of wires in electrical connection to the TES waveform generator.
Figure 14:
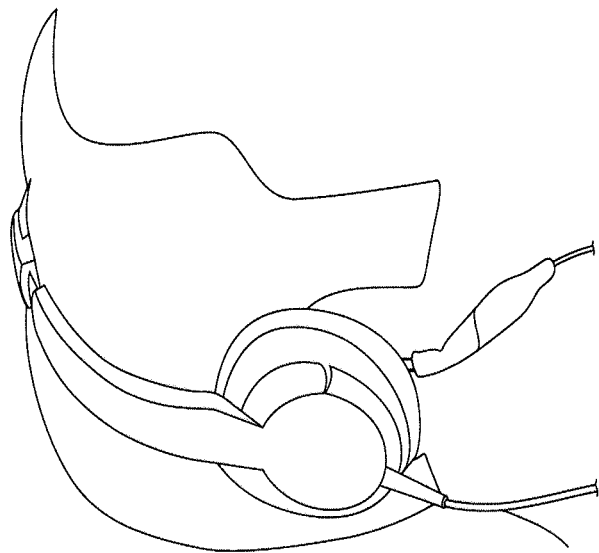
FIG. 14 is a schematic illustrating the use of one example of a pinna electrical nerve stimulation electrode in conjunction with a set of headphones.
Figure 13:
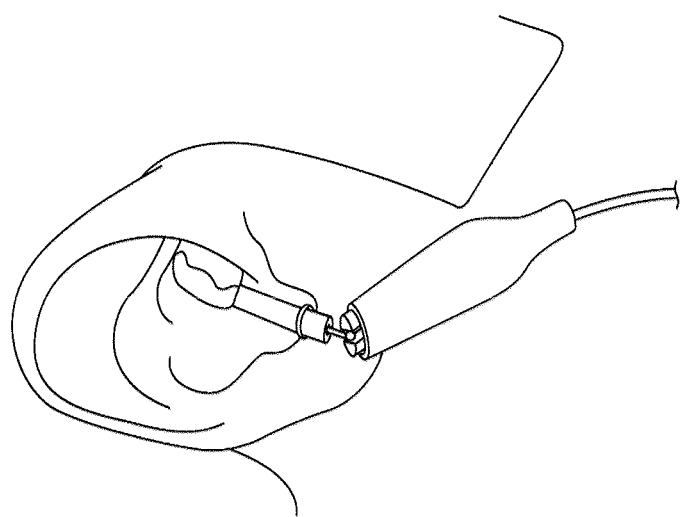
FIG. 13 is a schematic illustrating one example of a PENS electrode inserted into a wearer's ear.

In other embodiments as those shown in FIGS. 11-14, a first PENS electrode 1203 and a second PENS electrode 1204 can be fitted into the right and left ear of the wearer and controlled by triangular controller unit shown in FIG. 11 and FIG. 12 (1210). The first and the second PENS electrode are in wired communication with the neuromodulation device 1210. Either detachable leads or permanently connected wires couple the PENS electrodes to the neuromodulation device. In addition to the use of the PENS system, a wearer can add auditory stimuli (such as music or binaural beats) through use of a set of headphones in conjunction with the PENS system as shown in FIG. 14.

Figure 16:
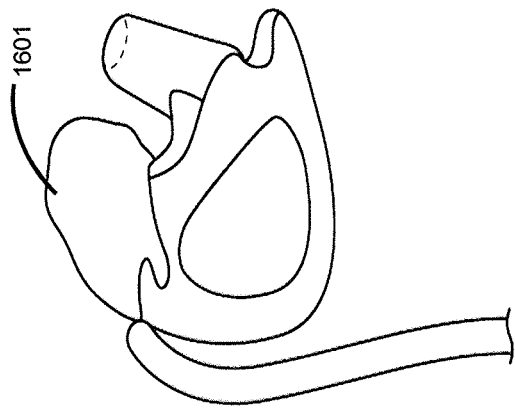
FIG. 16 is a schematic illustrating the variation of the pinna electrical nerve stimulation system shown in FIG. 15 where a pinna module is fitted into a wearer's ear where the pinna electrical nerve stimulation electrodes are permanently connected to wires for connecting the TES waveform generator.
Figure 15:
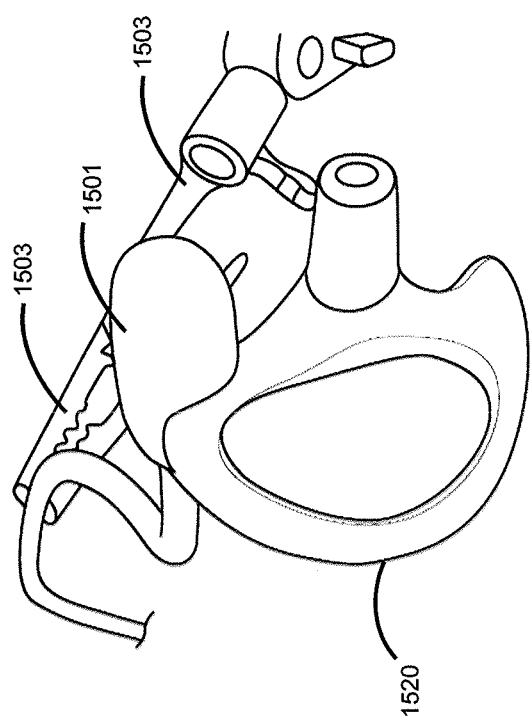
FIG. 15 is a schematic illustrating a variation of the pinna electrical nerve stimulation system where a pinna module is fitted into a wear's ear and a clip is used to hold the pinna module for display purposes only and is not used to couple the pinna electrical nerve stimulation electrode with the TES waveform generator.

Another alternative embodiment of the PENS system can be seen in FIGS. 15-17. In this configuration, right and left ear fitting structures are coupled to PENS electrodes 1501. (Note that the metal clip 1503 shown in FIG. 15 is to hold the system for photography and not a functional part of the system in use.) In FIG. 15, detachable electrical leads couple the PENS electrodes to the neuromodulation device. The PENS electrodes are coupled to generic earbud attachments 1520 that fit comfortably into a wearer's pinna. It should be noted that additional contact points may be made along earbud attachment 1520 to other regions of a wearer's pinna to provide alternate points of stimulation. The illustration in FIG. 15 shows a unipolar PENS electrode assembly for one ear; two such units are required for bipolar stimulation bilaterally in this embodiment. Alternatively in FIG. 16, the PENS electrodes may be hard wired to connect to the neuromodulation device. This particular embodiment has the advantage that there are other possible points of contact with the pinna region of the ear compared to previous embodiments where stimulation is sent to largely the meatus. The ability to contact other regions of the pinna can potentially provide additional neurostimulation that affect other regions of a user's nervous system.

Figure 20:
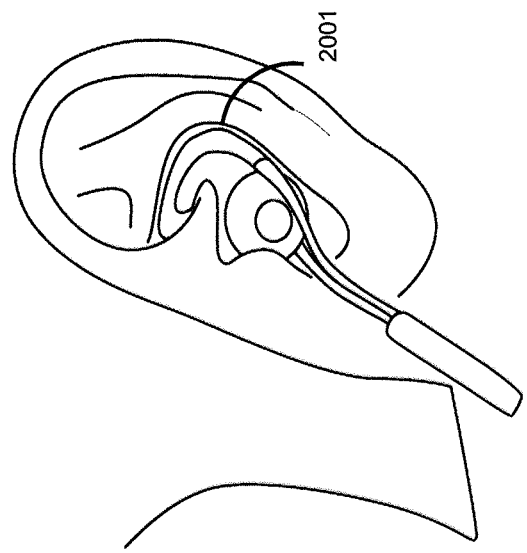
FIG. 20 is a schematic illustrating the second variation of the pinna electrical nerve stimulation system in a wearer's ear.
Figure 19:
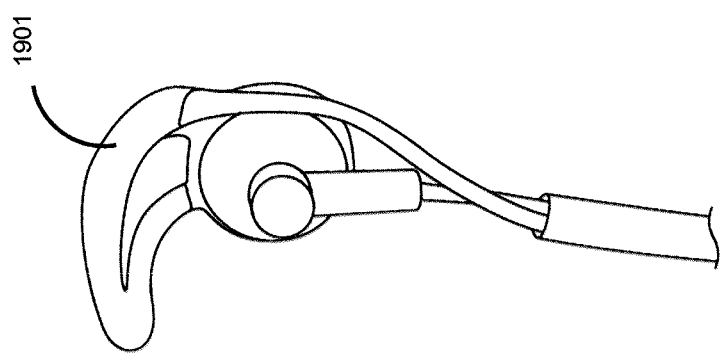
FIG. 19 is a schematic view of the lateral, non-wearer facing side of one of the pinna electrical nerve stimulation system assemblies shown in FIG. 18.

Yet another embodiment of a PENS system is shown in FIGS. 18-20. In this particular embodiment, PENS electrodes 1801 are integrated into a headphone system 1830. Headphones 1830 are wired to the neuromodulation device.

It should be noted that electrodes 1801 can be covered with cushioned conductive material such as conductive rubber, conductive foam, conductive silicon, and so on, to provide not only comfortable fit but also excellent contact between the wearer's skin and electrodes 1801. In some variations, the conductive portion of the electrode assembly has multiple conductive layers configured to distribute current more evenly and/or to provide electrochemical buffering of pH changes caused by charge imbalanced waveforms. See, e.g., FIGS. 22A-22F, described in detail below. For example, a first conductive metal layer (e.g. silver) is coated with a higher impedance material (e.g. conductive rubber, conductive foam, conductive carbon, or another material), which is then covered by a consumptive Ag—$AgCl_2$ layer and a dermal-facing hydrogel. In another example, a two-layer pinna electrode comprises a conductive metal layer covered by a conductive rubber or conductive silicone. Multilayer flexible electrodes are described in U.S. patent application Ser. No. 14/634,664 filed Feb. 27, 2015 by one of the named inventors of this invention and titled "CANTILEVER ELECTRODES FOR TRANSDERMAL AND TRANSCRANIAL STIMULATION," incorporated in its entirety herein by reference. The integration of the PENS electrodes with an audio producing component allows for production of both neuromodulated stimuli as well as an auditory stimulus if desired but still allows for auditory output or neuromodulated stimuli alone.

Figure 21:
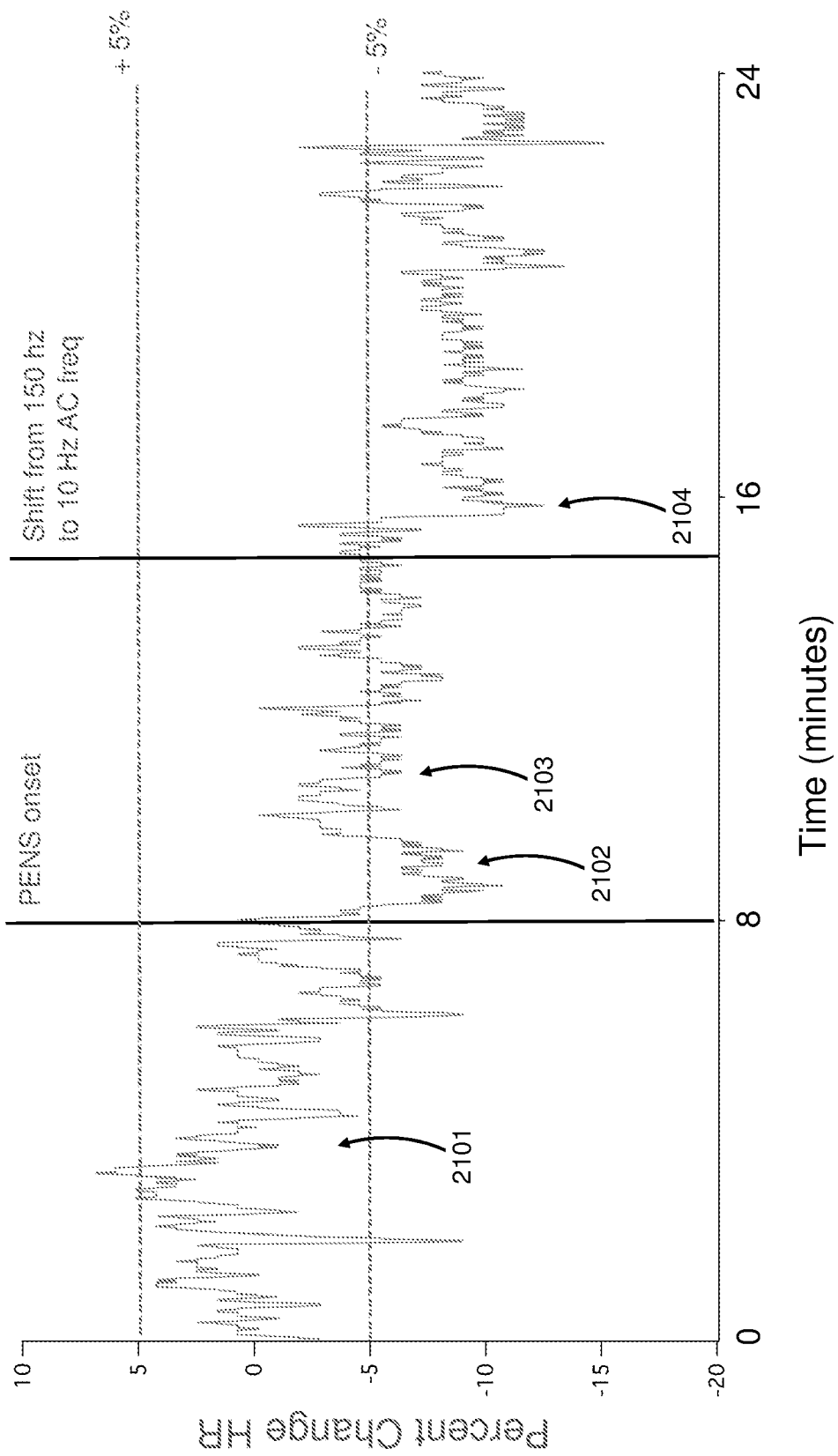
FIG. 21 shows a plot of the relative change in heart rate before and during a pinna TES session in a subject.

The PENS system shown in FIGS. 18-19 was placed bilaterally in both ears of a subject (as shown for one ear in FIG. 20) while the subject's heart rate was measured with an optical heart rate sensor (i.e. by plethysmography). The data of this experiment is shown in FIG. 21. For baseline period 2101 until about the 8 minute mark of the experiment, the subject's heart rate (HR) generally fluctuates within +/−5%. At the onset of bilateral PENS stimulation at about the 8 minute mark of the experiment, the subject's HR drops significantly 2102, reaching a level of 10% HR reduction before rebounding to a stable baseline of about 5% reduction 2103. This pattern of HR reduction and rebound is a known feature of vagal regulation of HR, indicating modulation of vagal pathways by PENS in this subject. At about 15 minutes of the experiment, the bursting frequency (referred to in the figure as 'AC freq') is shifted from 150 Hz to 10 Hz, causing further reduction of HR and a stable reduced HR baseline 2104. For this experiment, the stimulation parameters were about 1 mA peak intensity and 9.4 kHz pulsing frequency with monopolar pulses at 50% duty cycle and no capacitive discharge.

Pinna neuromodulation devices may be wireless and battery-powered and controlled remotely by a smartphone, tablet, or other computerized connected device (i.e. wearable device such as a smartwatch or smart glasses). Communication between the remote controller and the neuromodulation device may use a standard communication protocol such as Bluetooth or a custom communication framework. Instead of or in addition to wireless communication, the neuromodulation device may have wired cables that connect to a controller device (much as wires from earbud headphones connect to an audio controller via a headphone jack port, though in variations of the system it may be configured to connect to a computer bus/power connector (e.g. the Lightning connector on Apple products ca. 2015) to provide control and/or power to the neurostimulator). Wireless and/or wired communication may control electrical stimulation (e.g. waveform parameters, intensity, starting and stopping a waveform, etc.) and/or deliver auditory stimulation (music, spoken word, white noise, structured noise intended to drive specific brain rhythms, or binaural beats, such as stimuli at frequencies of brain rhythms (about 0.5 to 200 Hz) generated by delivering two fundamental frequencies within auditory hearing range (i.e. 1 kHz) that differ by the targeted brain rhythm (i.e. 12 Hz)).

Pinna neuromodulation devices may be bilateral, permitting stimulation of both right and left ears simultaneously or in close temporal proximity (i.e. with a latency between left and right pinna TES of less than about 5 minutes; less than about 4 minutes; less than about 3 minutes; less than about 2 minutes; less than about 1 minute; less than 30 seconds; less than 10 seconds; less than 1 second; etc.). Bilateral stimulation that includes auditory stimuli in addition to electrical stimulation targeting one or more cranial and/or cervical spinal nerves of the pinna may be advantageous for modulating brain physiology (e.g. brain rhythms) via binaural beats.

A bimodal ear stimulator includes PENS electrodes or electrode materials for simultaneously delivering acoustic stimuli to the inner ear and electrical neurosignaling waveforms to the pinna including, but not limited to the triangular fossa, meatus, conchae, tragus, and superficial surface of the auditory canal. In some instances, auditory stimulation may be transmitted by bone conduction speaker components of the neurostimulator mounted near the pinna. In other embodiments, the system may be configured to stimulate multiple regions of the pinna simultaneously or sequentially for targeting two or more branches of cranial and/or cervical spinal nerves, and may optionally be combined with auditory stimulation, such as music.

One or more (e.g., two) electrodes may be positioned on the skin of the pinna to target one or more branches of cranial and/or cervical spinal nerves. Appropriate structural, mechanical, and/or electrode array systems for placement of dermal electrodes are beneficial for targeting cranial and/or cervical spinal nerves projecting to and from the pinna and the brain and/or spinal cord.

The location of electrodes of the PENS apparatus may be fixed relative to the rest of the neurostimulator device. The electrodes may be integrated with a housing of the neurostimulator or attached via a structural component that may extend some distance away from the main housing of the neurostimulator.

Alternatively, an arm, including one or more electrode, or other structure may permit movement of the electrode to a particular position through a high level of force (yet easily exerted by the fingers of a user) while at the same time being sufficiently firm so that the shape and position is retained between uses.

The ability to (in some variations) move the location of one, two, or more electrodes while having a structure, component, or assembly that maintains that positioning during and between uses is beneficial for simplifying autonomous use by a subject. For example, flexibility of electrode location and retention of shape may be achieved by a multi-component structure (i.e. as used commonly in mobile tripods such as that described in U.S. Pat. No. 7,891,615).

A screw, clasp, snap, or other mechanical feature of the wearable neurostimulator may be configured to extend and/or rotate and may have multiple joints and/or axes of movement so that a position is set by the user or a third party, then fixed in place for between-session consistency of electrode position In embodiments, one or more pinna electrodes may be positioned by a skilled practitioner (i.e. medical professional or other individual well-versed in the position of cranial and cervical spinal nerves in the pinna).

In embodiments, a custom-fit aspect of (or attachment to) a pinna transdermal electrical stimulation system—or an electrode assembly configured to attach to a pinna transdermal electrical stimulation system—may be generated for each user by molding, 3D scanning, or another method of determining a complex 3D shape. For example, a custom-fit attachment for interfacing two or more electrodes to the skin of a user's pinna may be 3D printed with biocompatible electroconductive material, such a silicon or similar polymer formulations known in the art. Alternatively, multiple sizes or shapes of electrode assembly or other attachments may be provided to a user, similar to how multiple sizes and shapes of soft attachments are used for speaker earbuds. For example, electroconductive polymer formulations can be molded such that an electroconductive material comprises the portion of an earbud headphone that fits into the outer region of the ear canal (meatus) to provide simultaneous auditory stimulation during the delivery of electrical stimulation waveforms to the nerves innervating the pinna. In a similar embodiment, the PENS earbud may have arms that extend from the earbud base to make contact to multiple regions of the pinna such as the helix, triangular fossa, and cavum conchae.

Figure 8B:
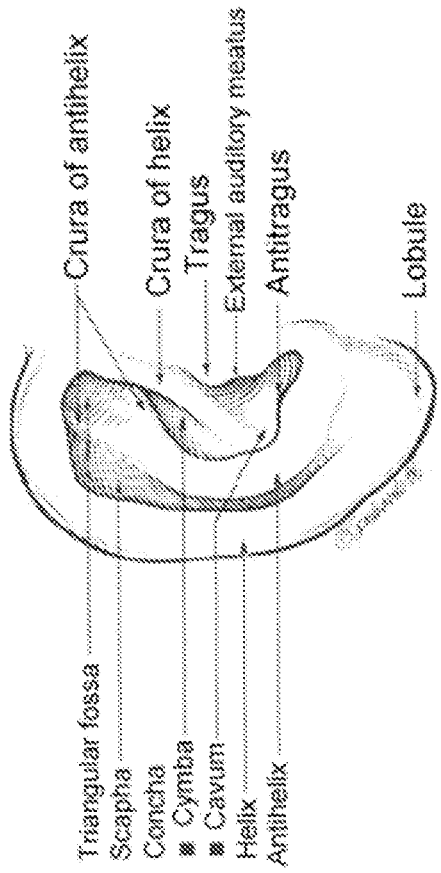
FIG. 8B is a schematic illustration of an ear, including various regions; the apparatuses and methods described herein may contact and/or stimulate any of these regions or groups of regions within the pinna (concha).
Figure 8A:
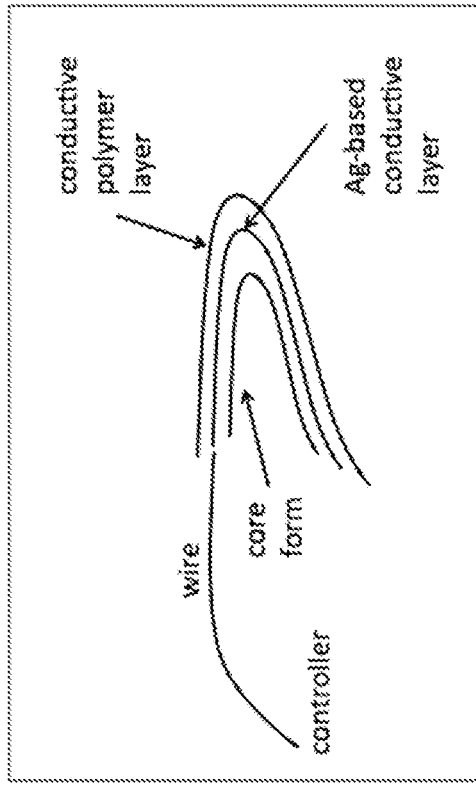
FIG. 8A is a schematic of a transdermal electrical stimulation electrode.

In addition to the methods of providing comfortable, form-fitting electrodes, other suitable materials can be used. These materials include silver-based conductive materials, conductive foams, conductive silicon, conductive rubber, and so forth. These conductive materials are generally the dermally-contacting portion of the electrode assembly and may comprise several layers of materials in order to achieve both relatively uniform current density and comfortable electrochemistry in contact with the skin. For example, FIG. 8A shows a schematic representation of a pinna electrode that derives its shape from a (generally) nonconductive core form covered by a first layer of an Ag-based conductive material (e.g. silver epoxy) which is nonconsumptive, has low internal impedance, and distributes current relatively uniformly across the dermal-facing surface of the electrode, and a second conductive polymer layer (e.g. nickel doped silicon, conductive foam (e.g. a highly resilient Nickel-Copper polyurethane foam that is sandwiched between knitted and non-woven fabrics from Schlegel Electronic Materials (Rochester, NY)), or conductive tubing with a conductive wire or carbon nanotube mesh) that makes direct contact with the skin for more comfortable transmission of the pinna TES waveforms to the user. Generally, a wire connects to or runs within a portion of the first layer of the electrode (i.e. the layer furthest from the user's skin). Electrodes may be formed to contact a varied sizing of pinna as well as contact different regions of the pinna. In the embodiments shown in FIGS. 18-20, a conductive, but also comfortable material (i.e. nickel doped silicon) 1801, 1901, 2001 can encase a region of the PENS electrodes that is in contact with the subject's pinna thereby delivering the neuromodulated stimulation to the desired region of the subject's pinna and at the same time be comfortable to wear. Similarly, the embodiment shown in FIGS. 15-16, concha-facing portion 1501, 1601 may comprise a first layer of silver epoxy and a second layer of nickel doped silicon sized and positioned to achieve a press fit contact with the concha when the earpiece form is placed in a user's ear. Note that in some variations, the electrodes on the apparatus (e.g., on the concha-facing portion(s), etc.) may be formed on any appropriate material. In particular, the material may be formed of multiple layers (e.g., of hydrogel and/or layers of conductive material (e.g., silver, silver chloride) and charge-spreading material (e.g., carbon), as illustrated and discussed below in relation to FIGS. 22A-22F.

In other embodiments, the region of the PENS electrode that is in contact with the subject's skin can be doped with a medicant that numbs or desensitizes the skin to continued contact. The addition of such a medicant can prolong a user's tolerance of having the electrodes against their skin while still providing the appropriate levels of neurostimulation required to elicit a cognitive, behavioral, and/or physiological effect. Useful medicants include topical anesthetics such as lidocaine, benzocaine, and tetracaine. A person skilled in the art would appreciate that there is a plethora of other skin de-sensitizing agents that would be similarly effective.

Pinna TES may be localized by using an array of electrodes positioned on different portions of the pinna and activated selectively based on the cranial nerve, cervical spinal nerve, or set of cranial and/or cervical spinal nerves targeted. For this type of stimulation targeting, personalization can be particularly beneficial so that stimulation targets a particular user's anatomy effectively and can be reliably repeated across PENS sessions. In an exemplar embodiment, a first pinna TES session tests different sets of electrodes within the array while receiving feedback from the user via one or more of: subjective report (i.e. of the comfort of stimulation and any subjectively apparent cognitive or physiological effect); physiological measurement (heart rate, heart rate variability, breathing rate, facial infrared thermography to detect changes in dilation of skin vasculature, galvanic skin conductance, biochemical markers, pupil dilation, etc.); brain recording of neuronal activity in the brain or a nerve; survey, assessment, or cognitive task. The system can then associate a target state (as defined by one or more of subjective reports; physiological measurement; neuronal recording; and cognitive task) with pinna TES via a particular set of electrodes in the array for a specific user, then save this information in a user-dedicated record locally or remotely so that future pinna TES sessions in that user apply stimulation through the effective electrode pads. In at least some instances, different stimulation parameters (i.e. varying intensity, frequency, duty cycle, bursting parameters, or other waveform parameter) may also be assessed while determining the comfort and efficacy of stimulation, then effective stimulation parameters may be saved specifically for the user in order to provide more comfortable and/or effective stimulation in future pinna TES sessions. The information concerning which electrodes to use for stimulation and/or about comfortable and effective waveform parameters may be stored in one or more of: locally in a wearable device that includes a pinna TES controller; a connected device (i.e. smartphone, smartwatch, tablet, etc.) in wired and/or wireless communication with the pinna TES controller; and on a remote server connected via the Internet to the pinna TES controller and/or a connected device in wired/wireless communication with the pinna TES controller.

A pinna electrode of the systems described here may be replaceable and consumable (i.e. disposable or semi-disposable) and may include components for buffering pH for charge imbalanced waveforms to improve the comfort of stimulation.

In general, an electrically active region of an electrode apparatus is shown in FIG. 8A. The electrode includes a core form conductive layer. In FIG. 8A, the core layer is a silver based conductive layer. But it can be conceived that conductive core layers of different compositions such as copper, gold, aluminum and so forth can also be used. Further, conductive alloys can also be used for the core layer. Next, the PENS electrode includes a conductive polymer layer. The conductive polymer layer serves two main functions. First, suitable polymers have to be malleable for comfortable fit within a range of pinna sizes. And second, suitable polymers have to be conductive in order to transmit the appropriate amount of neuromodulation from TES. It can be conceived that adjusting where the conductive polymer layer contacts a wearer's pinna and thus altering the stimulation region could result in different effects. Suitable conductive polymers include but are not limited to conductive foams, conductive silicon, and conductive rubbers.

In general, a neurostimulation system (e.g., a neurostimulation systems for pinna TES) as described herein may include at least two parts: (1) a lightweight, wearable, neurostimulator device (neurostimulator) that is configured to be worn on, in, or near the ear such as behind the ear or around the back of the neck; and (2) a consumable/disposable electrode assembly. In some variations a third component may be a controller that is separate from but communicates with the neurostimulator. For example, in some variations the controller may be a user computing device that wirelessly communicates with the neurostimulator. In some variations, a wired connection is made between the pinna neurostimulator and the user computing device by a communications bus/power connector or headphone jack for two-way communication and, optionally, power supply of the neurostimulator apparatus. In some variations the controller is a mobile telecommunications device (e.g., smartphone or tablet) being controlled by an application that sends instructions and exchanges 2-way communication signals with the neurostimulator. For example, the controller may be software, hardware, or firmware, and may include an application that can be downloaded by the user to run on a wireless-connectable (i.e. by Bluetooth) device (e.g., smartphone or tablet) to allow the user to select the waveforms delivered by the neurostimulator, including allowing real-time or short latency (i.e. less than one second or less than 500 ms) modulation of the delivered neurostimulation to modify the user's cognitive state as described herein.

In variations, the system may be operated to induce either "calm" states of mind or "energetic" states of mind. These changes to psychophysiological arousal can be selected by the user and selectively induced by the application of different waveforms and/or pinna electrode configurations. Operating the system to induce a state of increased energy can be alternatively described as one or more of: enhancing focus and attention; enhancing alertness; increasing focus and/or attention; enhancing wakefulness; increasing subjective feeling of energy; increasing objective physiological energy levels; increasing motivation; increasing physiological arousal; and evoking a physical sensation of warmth in the subject's chest. Such changes in psychophysiological arousal may be mediated through modulation of cranial nerve activity by stimulating the pinna that then projects information back to sensory regions of the brain stem before being integrated by local circuits to affect the activity of the reticular activating system. Operating the system to induce a state of enhancing a calm or relaxed mental state can be alternatively described as one or more of: a state of calm within about 5 minutes of starting a TES session; a care-free state of mind; a mental state free of worry; induction of sleep; facilitating falling asleep; a perception of slowing of a passage of time; muscular relaxation; enhanced concentration; inhibition of distractions; increased cognitive clarity; increased sensory clarity; a dissociated state; a mild intoxication; a euphoric state; a relaxed state; enhanced enjoyment of auditory and visual experiences; reduced physiological arousal; increased capacity to handle emotional or other stressors; a reduction in psychophysiological arousal associated with changes in the activity of the hypothalamic-pituitary-adrenal axis and/or the reticular activating system; a reduction in biomarkers of stress, anxiety, and mental dysfunction; anxiolysis; a state of mental clarity; enhanced physical performance; resilience to stress; a physical sensation of relaxation in the periphery; and a perception of feeling the heartbeat.

The neurostimulator may apply an ensemble waveform for about 5-30 min (or longer) that is made up of different "blocks" having repeated waveform characteristics; the waveform ensemble may include transition regions between the different blocks. In general, at least some of the waveform blocks (and in some variations most or all of them) generally have a current amplitude greater than 0.5 mA (e.g., between 0.5 mA and 5 mA (though higher currents up to 30 mA may be possible in some embodiments), preferably a current amplitude of between 1 mA and 3 mA). The neurostimulator has a frequency range of 3 and 30 kHz, or 5 and 12 kHz, or 7 and 10 kHz (optimally between 6-8 kHz). The current is typically pulsed, biphasic, asymmetric, and has a duty cycle of between 10-99% (e.g., between 20-95%, between 30-80%, between 20-50%, optimally between 50-60%, etc.). Bursting (i.e. burst-modulated) waveforms may be particularly effective for inducing cognitive effects via PENS by using bursting duty cycles between 10-90% (preferably 40-80%) and bursting frequencies of 3-500 Hz.

Bursting waveforms may further permit the induction of both calm and energy cognitive states with fixed electrode locations (e.g. bilateral unipolar concha electrodes) by changing the frequency of bursting. For example, bursting frequencies of 40-500 Hz induce 'energy' cognitive states (e.g. limited amount of alertness at 40-80 Hz and more prominent energizing effects at 150 Hz or greater (i.e. 150-500 Hz)), while lower frequencies less than 10 Hz (and, in particular about 3 Hz) provide a calming, even sedative effect.

Figure 6:
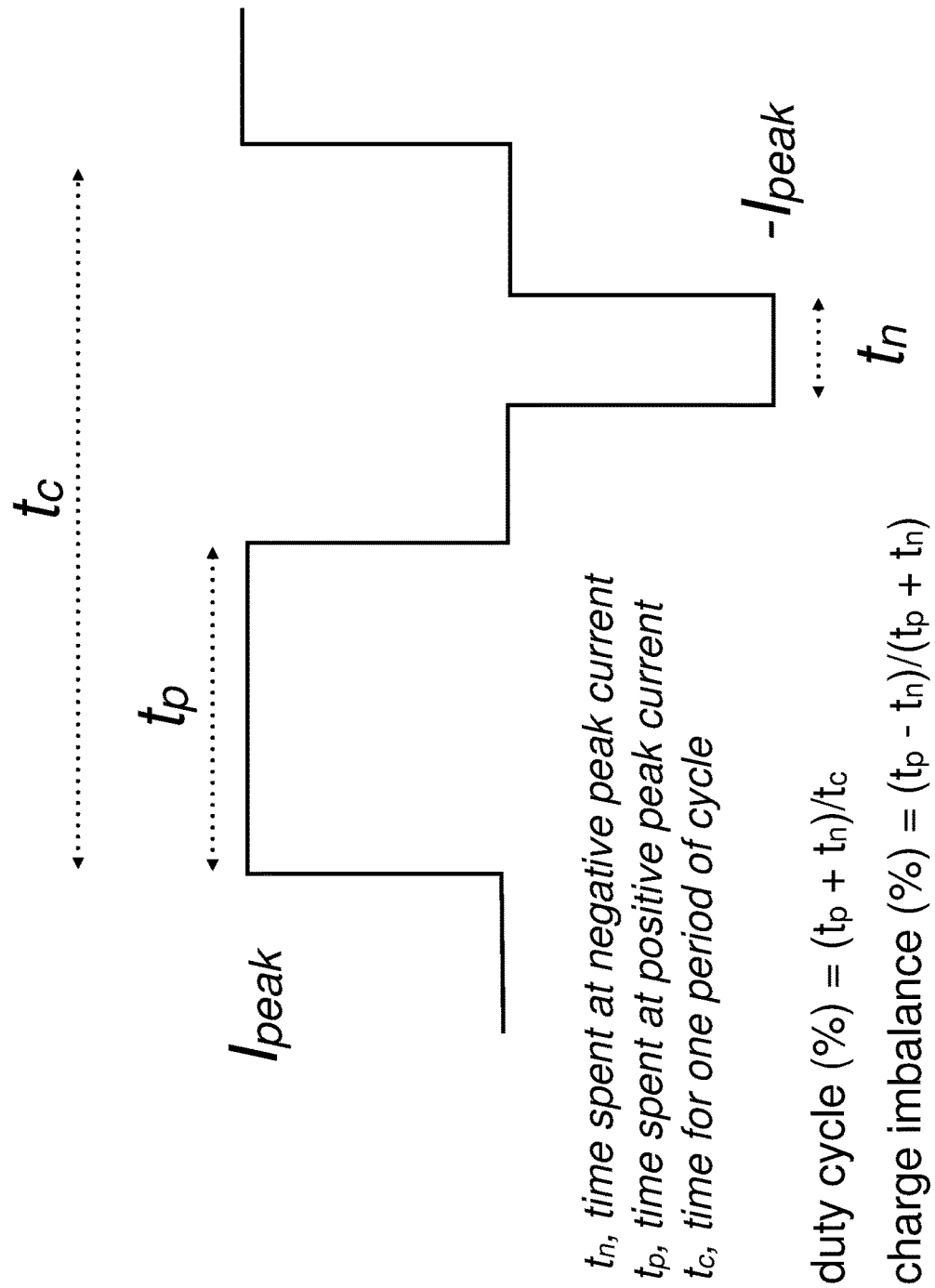
FIG. 6 is a diagram illustrating a cycle of a transdermal electrical stimulation waveform for stimulating one or more cranial and/or cervical spinal nerves in the pinna, as described herein.

One or more waveform characteristics may be changed during stimulation over timescales of every few seconds to minutes. FIG. 6 shows an exemplar cycle of a waveform for pinna TES comprising a positive-going pulse of duration $t_p$, a negative-going pulse of duration $t_n$, and a total pulse duration of $t_c$. As shown in FIG. 6 the peak of the positive- and negative-going pulses may be equal (absolute value). The duty cycle percentage may be defined as $(t_p+t_n)/t_c$ and the charge imbalance percentage may be defined as $(t_p-t_n)/(t_p+t_n)$. Finally, it has also been found that shifting the frequency in "bursts" increases the response to the neurostimulation (For example, having an initial frequency of 3 Hz, going up to 50 Hz, then 100 Hz, and back down).

Any of the PENS neurostimulators described herein may be lightweight (e.g., less than 30 g, less than 25 g, less than 20 g, less than 18 g, less than 15 g, etc.), and self-contained, e.g. enclosing the circuitry, power supply, microcontroller, current source, and, optionally, wireless communication components, rechargeable battery, charging circuit. A neurostimulator may also include safety circuitry.

In use, a user may interact with a controller (e.g., a smartphone controlled by application software/firmware) that pairs with the neurostimulator (e.g. by Bluetooth or a wired connection). The user may operate the controller to select the operational mode, e.g., the type of cognitive effect to be induced, such as an energy mode or calm mode, and/or the device could automatically detect based on the configuration of an electrode to which the apparatus is attached, a previous selection by a user, a physiological measurement of the user, a speech or facial recognition algorithm, or an augmented reality approach based on location, etc. The user may select, for example, from a set of ensemble waveforms which ensemble waveform to execute. There may be separate waveforms to evoke a desired experience/effect (e.g., an effect of enhanced calm or an effect of increased energy or other predominantly non-cognitive physiological effect).

An ensemble waveform may generally be between about 3-90 min (e.g., between about 3-60 min, between about 5-60 min, between about 5-40 min, etc., between about 3-25 minutes, etc.) long, or longer (e.g., greater than 3 min, greater than 5 min, greater than 10 min, greater than 12 min, etc.). In general, an ensemble waveform may be broken up into segments with specific pulsing parameters, i.e. current amplitude, frequency, duty cycle, charge imbalance, shorting/capacitive discharge, bursting frequency and duty cycle, etc., and these parameters may change at pre-specified times as they change to new segments; a transition period may be included to switch between block properties. Once the user selects an ensemble waveform, they can start the neurostimulation and the user can control or change the perceived intensity (e.g., by dialing the perceived intensity up or down), pause, or stop the session using the connected user device. In general, the perceived intensity can be scaled by the user between 0-100% of a maximum perceived intensity (e.g., one or more of a current, frequency, duty cycle, charge imbalance, bursting frequency and duty cycle, and/or shorting/capacitive discharge), using a control such as one or more buttons, sliders, dials, toggles, etc., that may be present on the controller (e.g., smartphone) in communication with the neurostimulator.

The controller may also allow a user to activate ("on demand") a waveform configuration that is designed to evoke a predetermined response. For example, the control device could be adapted to display one or more icons to trigger an audible sound or song—or an intensification of the perceived cognitive effect or skin sensation intensity. In addition, the controller may be configured to allow the user to press an icon to help in applying the electrode apparatus and/or neurostimulator. During or after a session, a user can access help screens, a profile page, social sharing interfaces (i.e. tweet your experience), feedback about a session, and analysis & history of previous use. In general, the system may also be configured to pass data to and from the controller and/or the neurostimulator and to/from a remote server via the Internet. These data may include user information, waveform data, information about the function or state of the hardware device or electrode assembly, etc.

In general, the TES controller may be specifically adapted to deliver an electrical stimulation signal of 10 seconds or longer between the first and second electrodes, where the signal has a frequency of 100 Hz or greater (e.g., 200 Hz or greater, 400 Hz or greater, 450 Hz or greater, 500 Hz or greater, 600 Hz or greater, 700 Hz or greater, etc.; optimally 750 Hz or greater, including 1 kHz or greater, 2 kHz or greater, 3 kHz or greater, 4 kHz or greater, 5 kHz or greater, 7.5 kHz or greater, 10 kHz or greater, 20 kHz or greater, etc.) and an intensity of 0.25 mA or greater (e.g., 0.5 mA or greater, 1 mA or greater, 2 mA or greater, 3 mA or greater, 4 mA or greater, 5 mA or greater, 6 mA or greater, 7 mA or greater, 8 mA or greater, 9 mA or greater, 10 mA or greater, etc.). The stimulation may be monophasic or biphasic. The controller may also be configured to reduce pain when applying the stimulation by controlling the duty cycle (e.g., the percent of time that the current applied is non-zero, and/or greater than zero), e.g. so that the duty cycle of the applied energy is greater than 10 percent (e.g., greater than 15 percent, greater than 20 percent, greater than 30 percent) and less than 90 percent (e.g., less than 75 percent, greater less than 70 percent, less than 60 percent). In addition, the controller may be configured so that the applied current is biphasic and/or is not charge balanced (e.g., has a DC offset, also referred to as DC bias, so that the mean amplitude of the applied waveform is non-zero). Alternatively or in addition, the controller (TES control module) may be configured to deliver waveforms biphasically asymmetric (i.e. not having the same pulse in the positive and negative direction) and/or to discharge capacitance built up on the electrodes (and in the body), e.g., by occasionally or periodically applying an opposite current(s). Alternatively or in addition, the controller (TES control module) may be configured to modulate the waveform at a second, generally lower, frequency that may be greater than 0.01 Hz (e.g. greater than 0.03 Hz, greater than 0.1 Hz, greater than 0.25 Hz, greater than 0.5 Hz, greater than 1 Hz, greater than 3 Hz, greater than 5 Hz, greater than 10 Hz, greater than 25 Hz, greater than 50 Hz, greater than 100 Hz), and provide a full (i.e. square wave, bursting) modulation or a relative modulation (saw tooth, triangular, sine wave, etc.). In general, a controller may be configured to generate stimulation that includes these parameters, and may be configured to prevent stimulation outside of these parameters, in order to avoid inducing pain.

The devices and methods described herein allow the reproducible evoking of cognitive and/or physiological effects, as are described herein. The nature of the cognitive and/or physiological effects resulting from the methods and devices described may depend, at least in part, on the positioning of the electrodes on the pinna and/or the parameters of the waveform being delivered (e.g. bursting frequency, see above). For example, a class of cognitive effects generally results in the subject experiencing an increased mental focus and may include: enhanced focus and attention; enhanced alertness; increased focus and/or attention; enhanced wakefulness; increased subjective feeling of energy; increased objective (i.e. physiological) energy levels; higher levels of motivation (e.g. to work, exercise, complete chores, etc.); increased energy (e.g., physiological arousal, increased subjective feelings of energy); and a physical sensation of warmth in the chest. This class of cognitive effects may be referred to collectively as enhancing (or enhanced) attention, alertness, or mental focus.

Another example of a class of cognitive effects includes those associated with relaxation and a calm mental state, for example: a state of calm, including states of calm that can be rapidly induced (i.e. within about 5 minutes of starting a TES session); a care-free state of mind; a mental state free of worry; induction of sleep; a slowing of the passage of time; enhanced physiological, emotional, or and/or muscular relaxation; enhanced concentration; inhibition of distractions; increased cognitive and/or sensory clarity; a dissociated state; a state akin to mild intoxication by a psychoactive compound (i.e. alcohol); a state akin to mild euphoria induced by a psychoactive compound (i.e. a morphine); the induction of a state of mind described as relaxed and pleasurable; enhanced enjoyment of auditory and visual experiences (i.e. multimedia); reduced physiological arousal; increased capacity to handle emotional or other stressors; a reduction in psychophysiological arousal as associated with changes in the activity of the hypothalamic-pituitary-adrenal axis (HPA axis) and/or by modulating the balance of activity between the sympathetic and parasympathetic nervous systems generally associated with a reduction in biomarkers of stress, anxiety, and mental dysfunction; anxiolysis; a state of high mental clarity; enhanced physical performance; promotion of resilience to the deleterious consequences of stress; a physical sensation of relaxation in the periphery (i.e. arms and/or legs); a physical sensation of being able to hear your heart beating, and the like. This class of cognitive effects may be referred to collectively as "a calm or relaxed mental state".

Another class of effects modifies the subject's physiology through the vagal nerve and affects one or more organ system, including but not limited to the gastric, intestinal, renal, hepatic, pulmonary, cardiac, circulatory, immunological, and nervous systems. Accordingly, transdermal stimulation of auricular vagal nerve branches with the systems and methods described herein may be applied for the treatment or diagnosis of various medical conditions, including but not limited to: alcohol addiction, Alzheimer's disease, anaphylaxis, anxiety disorders, apnea, atrial fibrillation, autism spectrum disorders, bulimia nervosa, burn-induced organ dysfunction, chronic heart failure, chronic intractable hiccups, comorbid personality disorders, concussion and post-concussive syndrome, coronary artery disease, Dravet syndrome, drop-attacks, eating disorders, epilepsy, fibromyalgia, genital self-stimulation after complete spinal cord injury, heatstroke, immune disorders, intestinal epithelial barrier breakdown, Lennox-Gastaut syndrome, memory disorders, migraines, minimally conscious or persistently vegetative states, mood disorders, myocarditis, multiple sclerosis, obsessive compulsive disorder, peripheral arterial occlusion disease, obesity, psychiatric disorders, Rasmussen's encephalitis, sepsis, sleep disorders, tinnitus, transient focal cerebral ischemia, trauma-hemorrhagic shock, and traumatic brain injury.

Any of the waveforms described herein may be applied continuously or intermittently, including with variations such as transitions states (e.g., ramps) from outside of these ranges into these ranges or within the ranges of current and frequency (and in some variations, duty cycle, charge imbalance, and/or bursting frequency and/or duty cycle). In general, ramping and other waveform features can be incorporated in order to shift a waveform between different effective ranges of parameters for inducing a particular cognitive effect and thus achieve a more intense, longer lasting cognitive effect. Shifting between effective waveforms may be iterative (i.e. one parameter changes, than another changes) and may be repetitive (i.e. change from one waveform to a second waveform, then back to the first waveform, etc.; or toggling between three or more effective waveforms). In some embodiments, rapidly shifting one or more waveform parameters within an effective range induces a stronger cognitive effect, wherein rapid generally refers to less than 15 seconds and may be as short as one second or less.

As mentioned, the apparatuses described herein may include a controller having components operating at high voltage so that sufficiently high peak currents can be achieved (i.e. greater than 10 V, greater than 15 V, greater than 20 V, greater than 25 V, greater than 30 V, greater than 35 V, greater than 40 V, greater than 45 V, greater than 50 V, greater than 55 V, greater than 60 V, greater than 65 V, and greater than 75V). Impedances of a subject's tissue (mostly due to skin impedance) and hardware components of the system including electrodes are generally between 1 kOhm and 20 kOhm (though occasionally up to 30 kOhm or higher), so high voltage current sources above 50 V are beneficial for delivering higher peak currents required for inducing a cognitive effect.

Pinna TES may include electrically stimulating the at least two electrodes with the neurostimulator, such that the neurostimulator delivers stimulation waveforms to the at least two electrodes for transdermal electrical stimulation. This may deliver stimulation waveforms to the electrode apparatus from the neurostimulator. Stimulation waveforms may include one or more waveforms selected from the group including: constant direct current; pulsed direct current stimulation (also referred to as pulsed monophasic alternating current stimulation); pulsed direct current stimulation with a constant direct current offset; alternating current stimulation (also referred to as biphasic alternating current stimulation); pulsed biphasic stimulation; or combined direct current stimulation and alternating current stimulation (also referred to as biased alternating current stimulation). In some embodiments, modifications or changes to the pulse sequence may occur at discrete time points during naturalistic auditory stimulation, such as when the tempo, beats per minute, instrumentation, melody, etc. in a song changes.

In some variations, any waveform described above can be combined in series or in parallel (i.e. concurrently) to create a hybrid waveform, or ensemble waveform. In embodiments, any waveform described above can be added, subtracted, convolved, or otherwise amplitude modulated. Moreover, in embodiments, any waveform above can have its amplitude ramped using linear, exponential, or another ramp shape including by one or more controllers that the user may manually adjust during stimulation.

In some embodiments, pinna electrical stimulation waveforms may comprise square waves, sine waves, sawtooth waves, triangular waves, rectified (unimodal) waves, pulse-width modulated, amplitude-modulated, frequency-modulated, or other pattern of waveform. For preferred embodiments, a primary frequency of stimulation is between 100 Hz and 35 kHz (e.g., between a lower frequency value of 100 Hz, 200 Hz, 300 Hz, 400 Hz, 500 Hz, 600 Hz, 650 Hz, 700 Hz, 750 Hz, 800 Hz, 900 Hz, 1 kHz, 2 kHz, 3 kHz, 4 kHz, 5 kHz, 6 kHz, 8 kHz, 9 kHz, 10 kHz, and an upper frequency value or 1 kHz, 2 kHz, 3 kHz, 4 kHz, 5 kHz, 6 kHz, 8 kHz, 9 kHz, 10 kHz, 12 kHz, 15 kHz, 17 k Hz, 18 kHz, 19 kHz, 20 kHz, 21 kHz, 23 kHz, 25 kHz, 27 kHz, 30 kHz, 35 kHz, etc.); optionally between 5 kHz and 30 kHz; optionally between 7 kHz and 25 kHz; optionally between 5 kHz and 12 kHz. Alternatively, the primary frequency stimulation may be in any suitable range such that a cognitive effect is induced.

In some embodiments, the maximum intensity of pulses delivered to a subject via pinna TES is generally greater than 0.1 mA and less than 30 mA; optionally greater than 1 mA, greater than 2 mA, greater than 3 mA, greater than 4 mA, greater than 5 mA, etc.). For example, the amplitude may be between a lower value of about 0.1 mA, 0.2 mA, 0.3 mA, 0.4 mA, 0.5 mA, 0.6 mA, 0.7 mA, 0.8 mA, 0.9 mA, 1 mA, 1.5 mA, 2 mA, 2.5 mA, 3 mA, etc., and an upper value of about 1 mA, 2 mA, 3 mA, 4 mA, 5 mA, 6 mA, 7 mA, 8 mA, 9 mA, 10 mA, 11 mA, 12 mA, 13 mA, 14 mA, 15 mA, 16 mA, 17 mA, 18 mA, 19 mA, 20 mA, 25 mA, 30 mA, etc.). The maximum intensity may be of any suitable maximum intensity such that a cognitive effect is induced. In preferred embodiments using pulsed direct current stimulation and/or alternating current stimulation, efficacious peak current intensities are generally between about 0.25 mA and 5 mA.

As discussed above, any of the apparatuses described herein (transdermal neurostimulator apparatuses, also referred to as PENS apparatuses or pinna transdermal electrical stimulation apparatuses) may include a housing enclosing a high-voltage power supply having maximum voltage or may be coupled to a high-voltage power supply (e.g., of greater than 10V, greater than 15V, greater than 20V, greater than 25V, greater than 30V, etc.) and further configured to provide a supply voltage of less than the maximum voltage, wherein the supply voltage is adjustable. These apparatuses generally include a first connector configured to electrically connect with a first electrode and a second connector configured to electrically connect with a second electrode. Any of these apparatuses may also include a controller (e.g., coupled to or within the housing enclosing the power supply) that includes, e.g., a waveform generator configured to deliver a pulsed, asymmetric, monophasic and/or biphasic electrical signal between the first and the second connectors, wherein the waveform generator receives the supply voltage from the high-voltage power supply. Any of these controllers may also include a sensing circuit configured to detect an applied voltage between the first and second connectors (the $V_{applied}$). The sensing circuit may comprise an amplifier connected to one or both of the first and second connectors. The controller may also be configured to compare a difference between the supply voltage ($V_s$) and the applied voltage ($V_{applied}$) with a predetermined target voltage offset, and to adjust the supply voltage by decreasing the supply voltage if the difference between the supply voltage and the applied voltage is greater than the target voltage offset and to adjust the supply voltage by increasing the supply voltage if the difference between the supply voltage and the applied voltage is less than the target voltage offset.

In general, any appropriate high-voltage power supply may be used. For example, the high-voltage power supply may be configured to provide between 20V and 100V.

As mentioned above, the controller may be configured to decrease the supply voltage if the difference between the supply voltage and the applied voltage is above the target voltage offset and to increase the supply voltage if the difference between the supply voltage and the applied voltage is below the target voltage offset. The controller may be configured to adjust the supply voltage as a function of the difference between the supply voltage and the applied voltage.

In any of the apparatuses and methods described herein, the controller may be configured to determine if the apparatus is in an overheating state based on an applied current and the difference between the supply voltage and the applied voltage.

As mentioned above, in various embodiments, the controller of the neurostimulator (e.g., PENS apparatus) may include a capacitive discharge circuit configured to discharge a capacitance on the electrodes during the delivery of the biphasic electrical stimulation signal. Neurostimulators that incorporate discharging the capacitance on the electrodes may be useful for pulsed stimulation regimes, and may help reduce or prevent pain and discomfort. In some variations the apparatus includes capacitance discharging circuitry in connection with the electrodes. For example, as described above, capacitance discharging circuitry may include electronic components and firmware features that short the anode-cathode path to permit discharge of capacitance that builds up during a pulse (e.g., in the subject's skin). In some instances, short-circuiting is beneficial for reducing discomfort and accordingly increasing the cognitive effects induced by pinna TES (due to one or both of: reducing the distraction of discomfort so that other cognitive effects can be experienced by a subject and permitting higher peak current intensities to be delivered that induce more significant cognitive effects). In general, controlling the maximum current of a capacitance discharging pulse may be beneficial for tuning the comfort of a TES waveform (e.g. to vary the maximum current of discharge based on the estimated amount of capacitance built up, which is expected to correlate with increasing imbalance (i.e. duration and/or peak current) between positive-going and negative-going pulses, as well as by frequency, where lower frequency stimulation at a fixed duty cycle will cause relatively more capacitance build-up per cycle).

As used herein, the term "TES" may refer to pinna TES (e.g., application of TES at entirely or in part, the pinna using an apparatus such as a pinna TES applicator, including, e.g., PENS apparatuses and pinna transdermal electrical stimulation apparatuses). These apparatuses may generally be wearable, e.g. configured to be worn on a subject's ear(s), and worn on the subject's body. They may be worn on one ear (e.g., with one or both electrodes contacting the ear region, or with one electrode on the ear, e.g., pinna, and another on another region of the body, such as the neck, temple, or mastoid), or on both ears (e.g., one electrode on each ear).

As mentioned, the transdermal electrical stimulator (e.g., PENS) may comprise a controller having the capacitive discharging features (which may be referred to as a 'short circuiting' applicator) described. For example, the wearable transdermal electrical stimulator may include: a housing configured to be connected to a first electrode and a second electrode, a controller at least partially within the housing including: a processor, a waveform generator configured to deliver a biphasic electrical stimulation signal between the first electrode and the second electrode, and a capacitive discharge circuit configured to discharge a capacitance on the first electrode and the second electrode during the delivery of a monophasic or biphasic electrical stimulation signal. The controller may be adapted to deliver a electrical stimulation signal of 10 seconds or longer between the first and second electrodes having a frequency of between 100 Hz and 35 kHz (e.g., 400 Hz or greater, 750 Hz or greater, etc.), a duty cycle of greater than 10 percent, an intensity of 0.25 mA or greater, with a DC offset; and a capacitive discharge circuit, wherein the controller (control module) may be configured to occasionally trigger the capacitive discharge circuit to discharge capacitance on the electrodes during the delivery of the electrical stimulation.

FIG. 7A schematically illustrates a biphasic electrical stimulation waveform with a positive pulse and a negative pulse in one cycle. In some embodiments, the apparatus (e.g., the firmware, hardware and/or software) may create segments in a waveform cycle. The smallest segment may be limited by the clock of the processor. For example, in some embodiments, the shortest segment per cycle can be 2, 5, or 10 microseconds or any values there between. For example, in some embodiments, the firmware may create 10, 12, 15, or 20 segments per cycle. For each segment of the cycle, the controller may instruct the waveform generator to generate a positive intensity value, a negative intensity value, a value of "zero" which indicates an open circuit mode, or a capacitive discharge.

In some embodiments, the capacitive discharge (which may be referred to as "short-circuiting" although it is not the result of shorting) can be triggered immediately after the positive pulse or negative pulses as shown in FIGS. 7B-7D. For example, as shown in FIG. 7B, at the time when the positive pulse ends, the controller triggers the capacitive discharge circuit to short the anode-cathode path, resulting in a capacitive discharging pulse to permit discharge of capacitance. The minimum duration of the capacitive discharging pulse may be limited by the shortest segment of the cycle as discussed above. Thus the duration of the pulse can be larger than 2, 5, or 10 microseconds. However, the duration of the pulse may not be too short. It might be advantageous to have a more gradual pulse to prevent pain in the subject. It might be advantageous to have a limited peak value of the pulse to further prevent pain and discomfort. The peak value and the time constant of the capacitive discharging pulse may be controlled by the capacitive discharge circuit. In some other embodiments, the capacitive discharge can be triggered immediately after the negative pulse as shown in FIG. 7C. In some embodiments, the capacitive discharge can be triggered both after the positive pulse and after the negative pulse as shown in FIG. 7D.

Figure 7E:
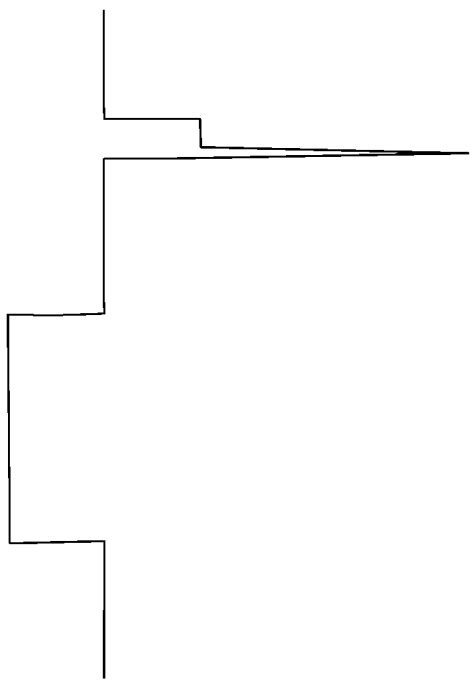
FIG. 7E is an example of another variation of a TES unit waveform that may be used, e.g., repeated alone or in combination with any of the other variations of unit waveforms shown in FIGS. 7A-7D, including a capacitive discharge current applied at the start of the second, negative-going, pulse.

In some alternative embodiments, the capacitive discharging pulse can be triggered at the onset of each negative-going pulse in the negative-going direction as shown in FIG. 7E. For example, in an "energy" mode (e.g., enhancing attention, alertness, or mental focus), the capacitive discharging pulse can be triggered at the onset of each negative-going pulse in the negative-going direction to induce an enhanced cognitive state. In some other embodiments, the capacitive discharging pulse may be triggered at the onset of each positive-going pulse in the positive-going direction. In some other embodiments, the capacitive discharging pulse can be triggered both at the onset of each negative-going pulse in the negative-going direction and at the onset of each positive-going pulse in the positive-going direction.

Figure 24:
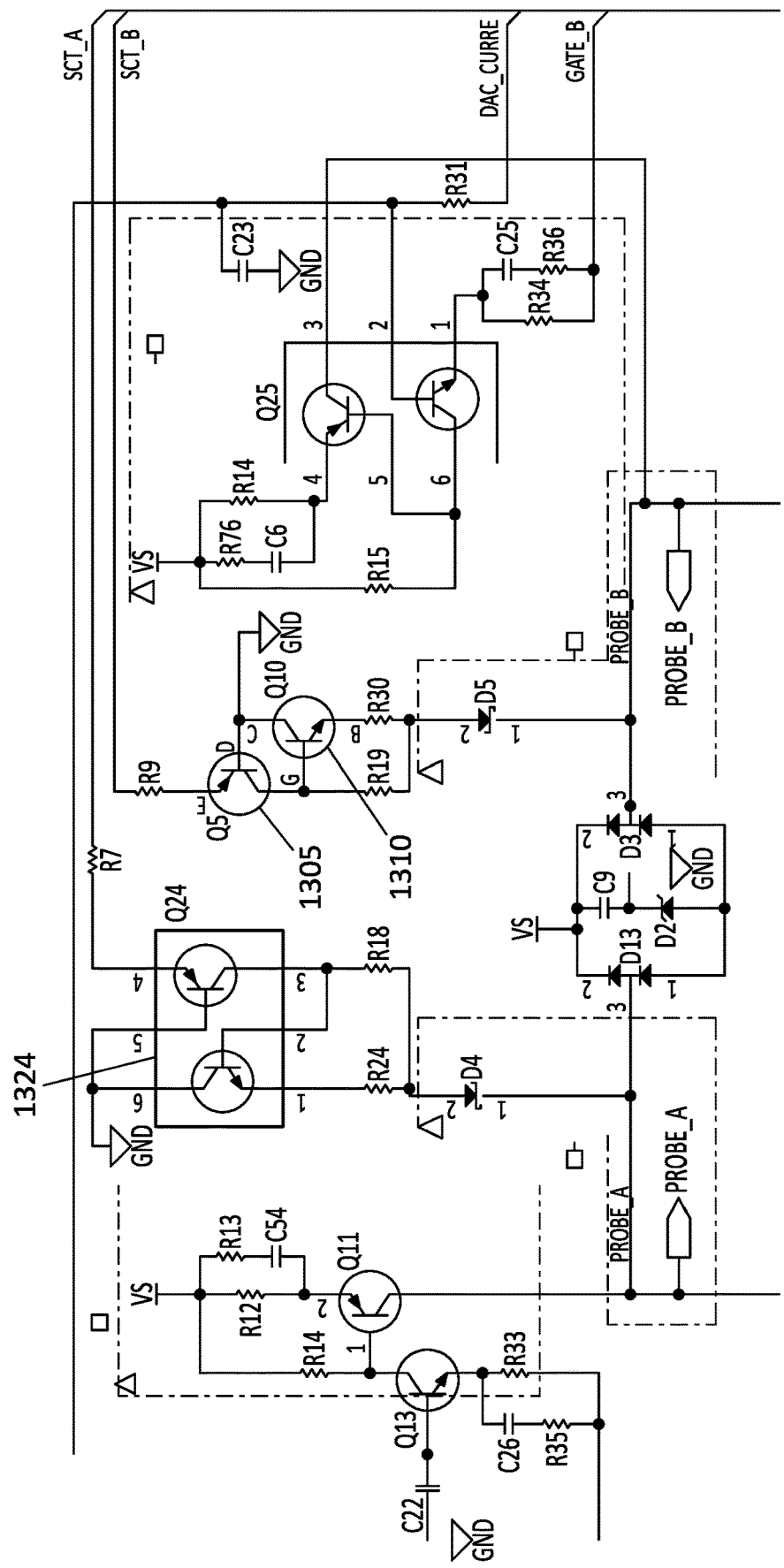
FIG. 24 schematically illustrates an example of a capacitive discharge circuit including a double H-bridge according to some embodiments of the disclosure.

FIG. 24 schematically illustrates an example of a capacitive discharge circuit including a double H-bridge according to some embodiments of the disclosure, which may be part of the controller described herein. The double H-bridge circuit can be configured to generate a gradual capacitive discharging pulse with controlled time constant and peak value. As discussed above, the outside H-bridge can be configured to adaptively adjust the applied voltage $V_s$ based on feedback signals. In addition to the outside H-bridge, the circuit can further comprise an inside H-bridge including transistors 1324, 1305 and 1310. The transistors 1305 and 1310 can be configured to form a current source, driving the current to the ground. When probe B is negatively charged, and probe A is positively charged, the transistors 1305 and 1310 can pull probe B to ground with a gradually discharging pulse. In the other direction, the transistors 1324 can be configured to form a second current source, driving the current to the ground. When probe A is negatively charged, and probe B is positively charged, the transistors 1324 can pull probe A to ground with a second gradually discharging pulse. Therefore, the inside H-bridge including transistors 1324, 1305 and 1310 can be configured to generate gradual capacitive discharging pulses with controlled time constants and peak values. In general, the double H-bridge circuit can be configured to generate gradual capacitive discharging pulses, in addition to adaptively adjust the applied voltage Vs using feedback signals.

For example, the waveform may have a frequency of 11 kHz, the time constant of the capacitive discharging pulse can be between 0.00001 to 100 microseconds. The peak value can be controlled to be between 0.001 and 10 mA in some embodiments. In some embodiments, the controller of the neurostimulator may include a switch configured to turn off the current source when the capacitive discharge circuit is triggered.

Figure 25A:
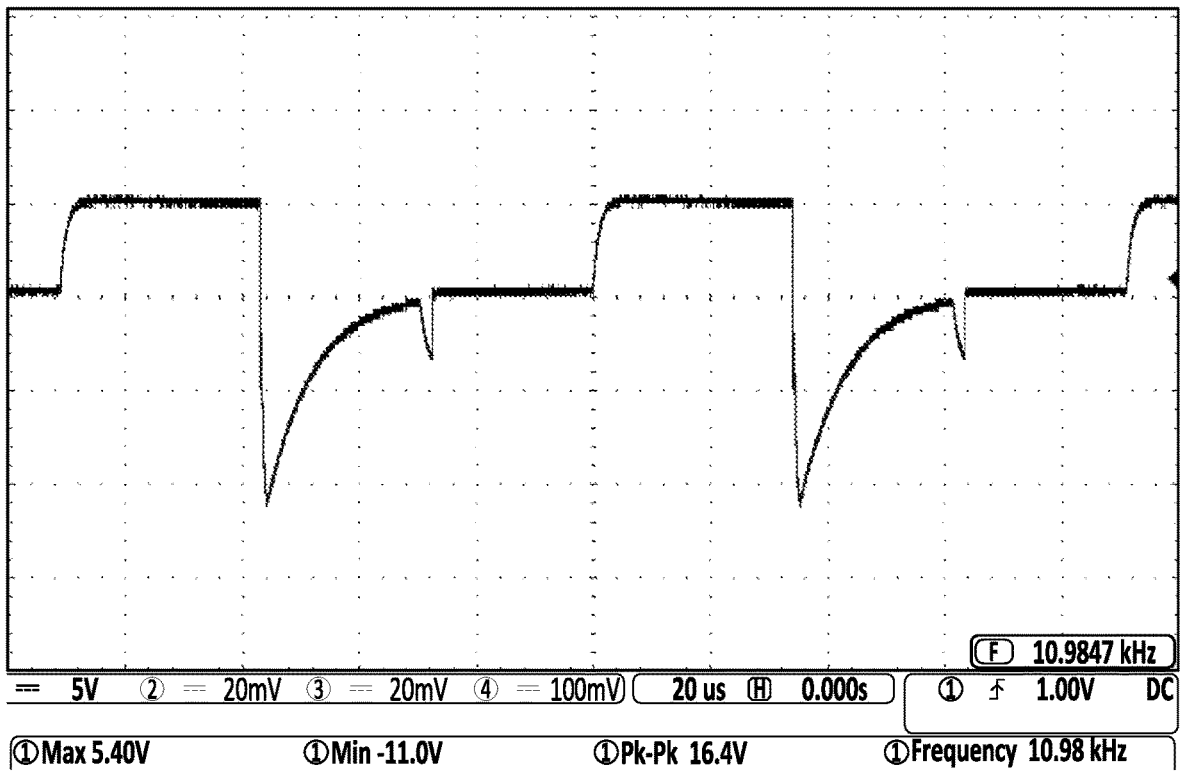
FIG. 25A illustrates an example of capacitive discharging pulses from the double H-bridge capacitive discharge circuit.

FIG. 25A illustrates an example of the capacitive discharging pulse from the double H-bridge capacitive discharge circuit, measured from the electrodes (e.g., the probes are at the electrodes). The discharging pulse immediately after the positive pulse can be controlled to have a gradual slope with a controlled peak value. The discharging pulse immediately after the negative pulse is small because there is only small amount of capacitance built up.

Figure 25B:
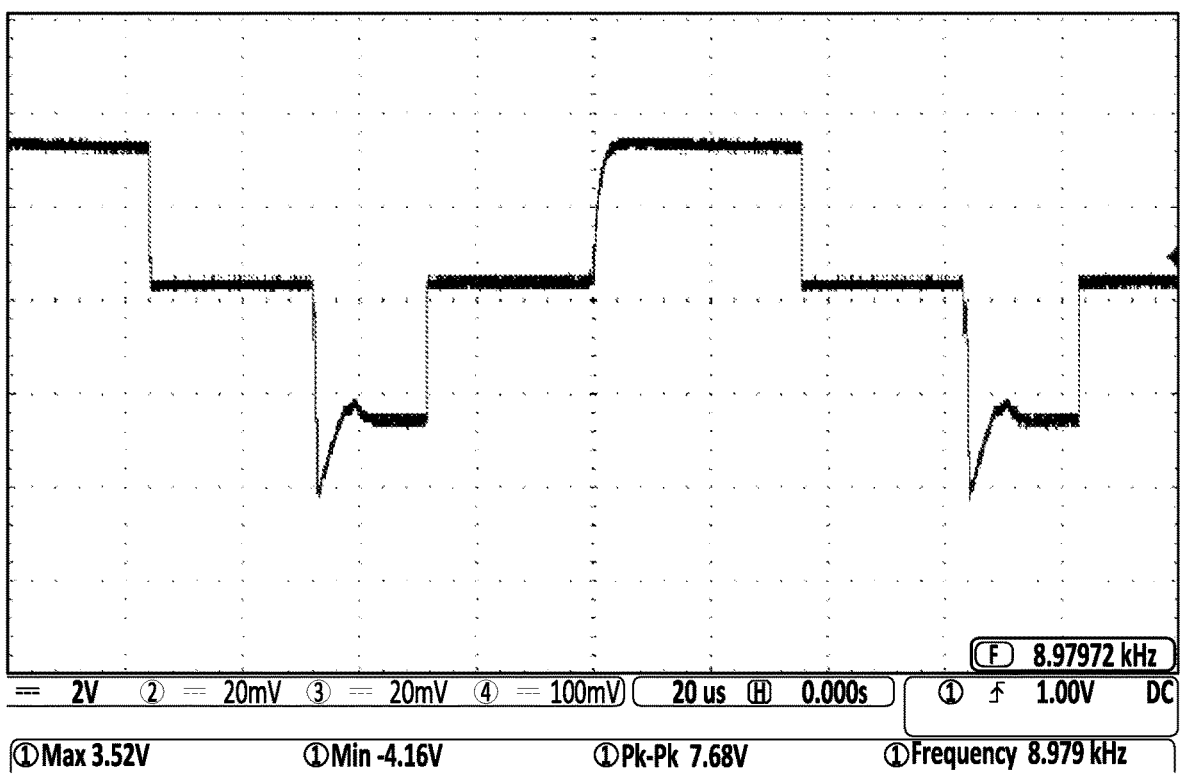
FIG. 25B illustrates another example of capacitive discharging pulses from the capacitive discharge circuit with the double H-bridge.

FIG. 25B illustrates another example of the capacitive discharging pulse from the capacitive discharge circuit with the double H-bridge. The discharging pulse is triggered at the onset of the negative going pulse in the negative going direction with a controlled time constant and peak value. The discharging pulse can be configured to enhance the "energy" cognitive state and minimize user discomfort.

In some other embodiments, the capacitance discharging circuitry may include electronic components and firmware features that short the anode-cathode path with a low ohm resistor (e.g. 50 Ohms) to permit discharge of capacitance that builds up during a pulse (e.g., in the subject's skin). In some other embodiments, the capacitive discharging circuitry may include a fixed current source similar to the main current source in the device, but saturating at 0V and allowing discharge of the accumulated charges. The discharge time may be fixed or may depend on the voltage and electrode capacitance. In one example a nominal short-circuit current may be adjustable (e.g., to 40 mA), which could be changed by changing a resistor. The discharge could be made by the regular current source with an adjustable current inside the range, e.g., up to 20 mA; turning on the two rectified bottom switches may avoid reverse charging in this case. In general, a capacitive discharge can be very quick (e.g. on the microsecond timescale) and could use a very high current, e.g., tens of mA to 100 mA.

In general, a biphasic pulse may include a positive-going pulse following (either immediately or after some delay) by a negative-going pulse. As described herein, these pulses are not limited to square-wave pulses, but may be saw tooth, or other shapes. In some variations, the positive-going and negative-going pulses may have different shapes. In some variations, the biphasic pulse includes a positive-going (or negative-going) monophasic square wave pulse and a capacitive discharge (from a capacitive discharge circuit) in the other direction. For example, the apparatus may be configured to apply a uniphasic square wave pulse (positive or negative going) and a capacitive discharge in the opposite direction. In general, waveforms may include bursting regimes wherein cycles of stimulation occur intermittently.

Figure 26:
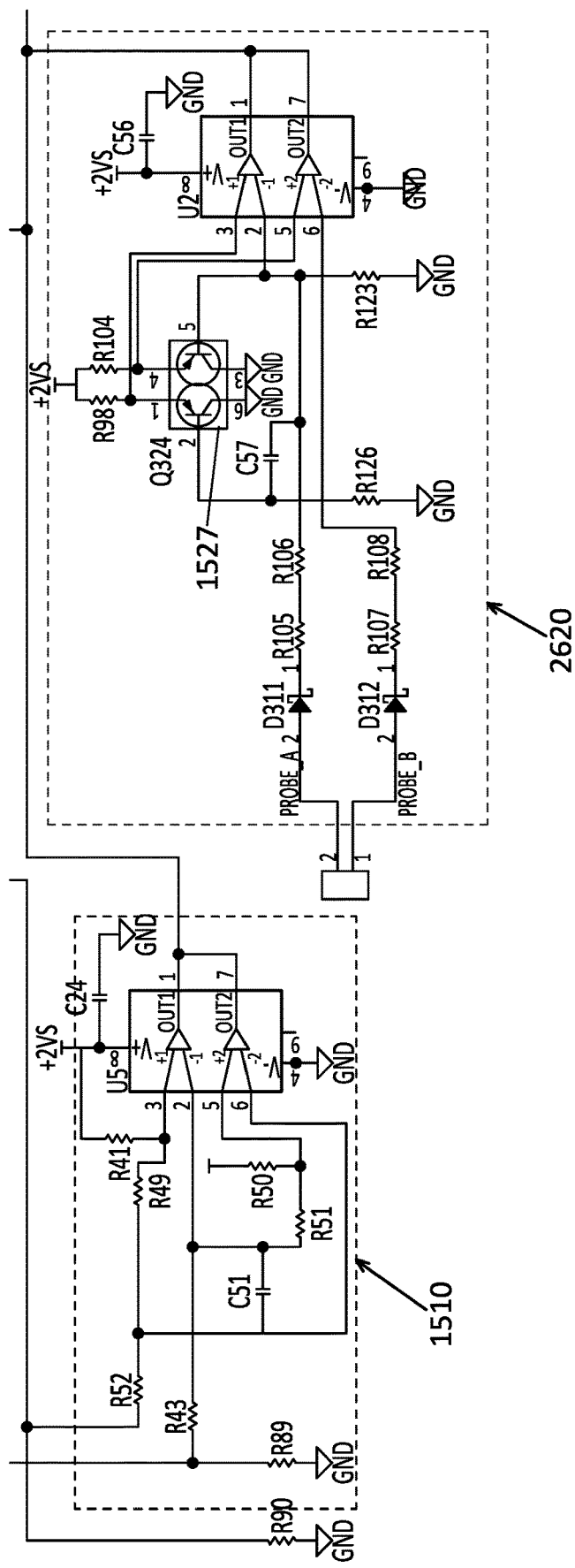
FIG. 26 schematically illustrates an example of a safety comparison circuit according to some embodiments of the disclosure.

FIG. 26 schematically illustrates an example of safety comparison circuits according to some embodiments of the disclosure. In various embodiments, the controller of the neurostimulator (PENS apparatus) can include safety comparison circuits configured to prevent the current and/or the voltage from exceeding maximum values. For example, the maximum DC current may be set at 5 mA, 8 mA, or 10 mA, or any values therebetween. Similarly, the voltage may have a maximum value for the safety of the subject as well. The circuit can be configured to shut down the power supply when the current or voltage exceeds the maximum value. For example, the safety circuit can comprise a current safety comparison circuit section 1510. The section 1510 can be configured to compare the current values in both directions and output a fault signal to the microprocessor if the current value in any direction exceeds the maximum value. The safety circuit can further comprise a voltage safety comparison circuit section 2620. The section 2620 can be configured to compare the voltage values in both directions and output a second fault signal to the microprocessor if the voltage value in any direction exceeds the maximum value. The voltage safety comparison circuit section 2620 can comprise a transistor 1527 to increase the sensitivity of the safety circuit.

The systems, devices, and methods of the preferred embodiments and variations thereof can be embodied and/or implemented at least in part as a machine configured to receive or include a computer-readable medium storing computer-readable instructions. The instructions are preferably executed by computer-executable components preferably integrated with the system including the computing device configured with software. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, but any suitable dedicated hardware or hardware/firmware combination can alternatively or additionally execute the instructions.

In any of the apparatuses described herein, an electrically conductive tethering wire may be a durable portion of the TES system and intended for long-term use. The tethering wire may connect to the electrode(s) and to a controller, such as a wearable microprocessor (e.g., smartphone, etc.). FIG. 27A shows exemplar schematic embodiments of a TES system comprising primary durable housing 2402, secondary durable housing 2401, connectors 2403 & 2404, and electrically conductive tethering wire 2405. Not shown are disposable electrodes that couple electrically and mechanically to housings 2401 (and in some variations 2402) and may contain a dermally-facing adhesive. In some variations the apparatus may include an adhesive so that the PENS system can be wearably attached to the user. Other variations of PENS systems as described herein may be non-adherent and otherwise wearably attached to a user's body (e.g. by a headband, headset, cap, etc.).

As shown in FIG. 27A the tethering wire may be permanently attached to the primary and secondary units, or it may be configured to unplug from either or both of the primary or secondary system housing (FIG. 27B, FIG. 27C) with standard or custom connector 2406, 2407.

In some embodiments, one of the durable primary and/or secondary housing may have a standard plug component (e.g. a male USB or male micro-USB connector) for charging and communication with other electronic or computing devices. For example, the smaller, secondary durable housing may contain a male USB connector, a charging circuit, and a battery.

In general, PENS systems may contain an electrically conductive cable that is permanently or detachedly attached may contain all components in a single housing. In such instances, the electrically conductive cable would include at least a connector at or near its end distal from the unit containing the electrical components to which a disposable electrode can be electrically connected.

Figure 28:
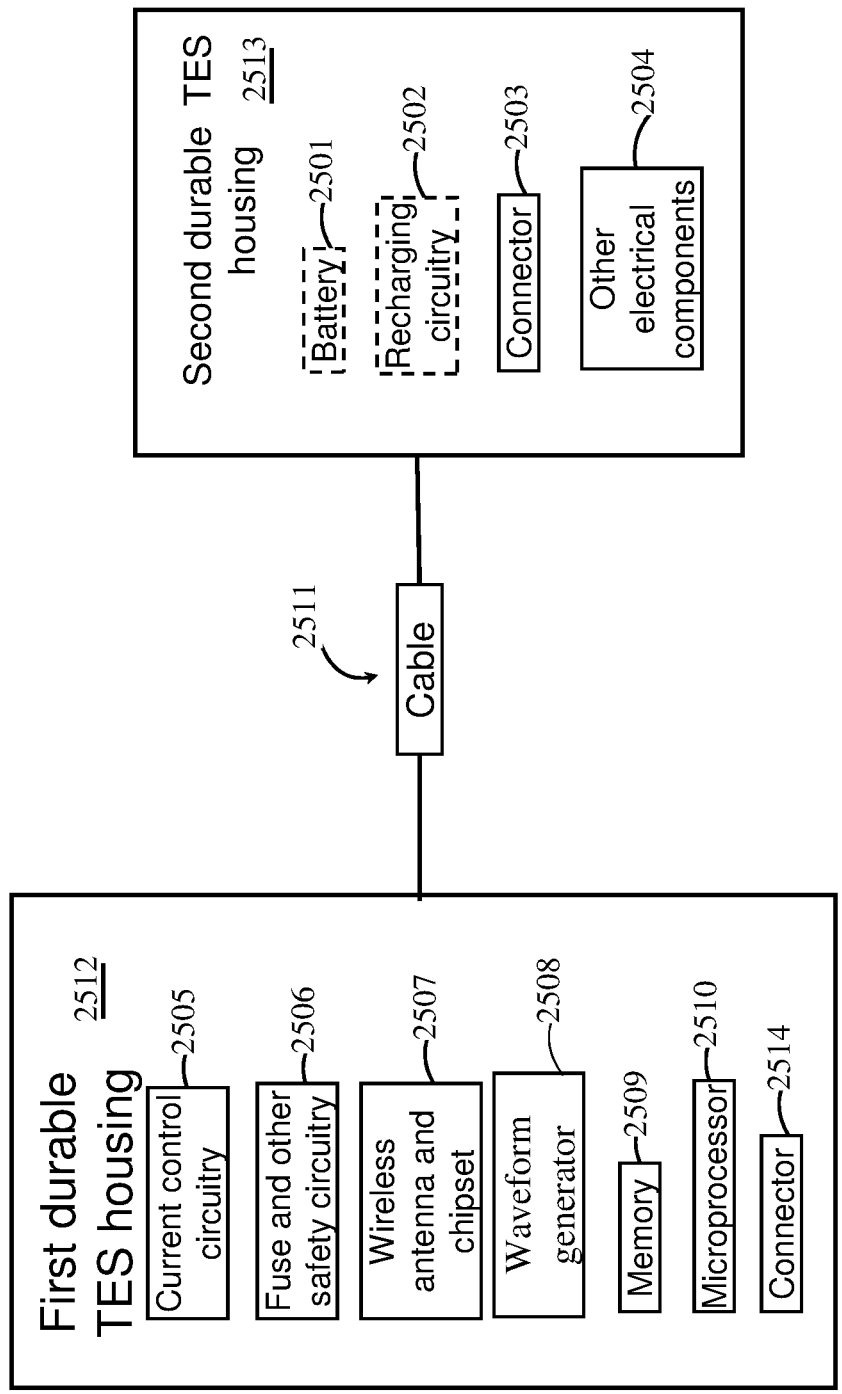
FIG. 28 shows the hardware features in a first durable TES housing and a second durable TES housing connected by a cable.

In general, a PENS system may contain an electrically conductive cable that is permanently or detachedly attached may contain components in two or more housings. These embodiments may be advantageous because they may permit miniaturization of each of the housings relative to having all components in a single housing. This miniaturization may improve comfort, wearability, durability, and/or fit of a PENS system. Any set of necessary or optional components may be selected to be in a first housing or a second housing (or a third housing, etc.). FIG. 28 shows an exemplary schematic of a PENS system schematic with first durable TES housing 2512, which may contain current control circuitry 2505, fuse and other safety circuitry 2506, wireless antenna and chipset 2507, waveform generator 2508, memory 2509, microprocessor 2510, and may include a connector (2514) to a first electrode. The connector may be part of or distinct from an electrically conductive cable 2511 that may connect to a second durable TES housing 2513. In variations having the second housing, the second housing may at least partially enclose a battery 2501, recharging circuitry 2502, connector to an electrode (e.g., a first electrode or in some variations a second electrode) 2503, and other electrical components 2504. The housing may be coupled to one or both electrodes directly. In some variations, where there are distinct electrodes (e.g., coupling to different ears), the controller (e.g., electronics) may be part of a housing that is coupled directly to one or both electrodes, without a connector wire, or it may be connected via a connector wire.

A method of using the PENS systems described herein can include connecting two controller housings with a detachable, reusable electrically-conductive cable, followed by connecting the two electrodes to the cable and/or TES controller. Alternative methods can employ the opposite ordering of connecting necessary and detachable system components.

A PENS apparatus with a durable cable connecting two housings with electrode connectors—or a single housing with two or more electrode connectors—may be used with disposable electrodes that do not have a wire connecting them. This system architecture may reduce the cost and complexity of a disposable set of transdermal electrodes, which typically only require a connector (e.g. electrically conductive button snap connector) configured to connect with the PENS controller system.

Electrode Configuration

As already discussed above, any of the electrodes described herein may be configured to have layers that help distribute the charge applied/received, enhance efficacy, and reduce irritation. For example, any of the variations described herein may include a sacrificial layer (e.g., Siver/Silver Chloride layer) that may be consumed during operation. The apparatus may also include one or more layers that comprises a pH buffer. Also, in some variations, the electrodes may include a current spreading layer (e.g., carbon black, etc.) that prevents local current maxima during operation.

Figure 22A:
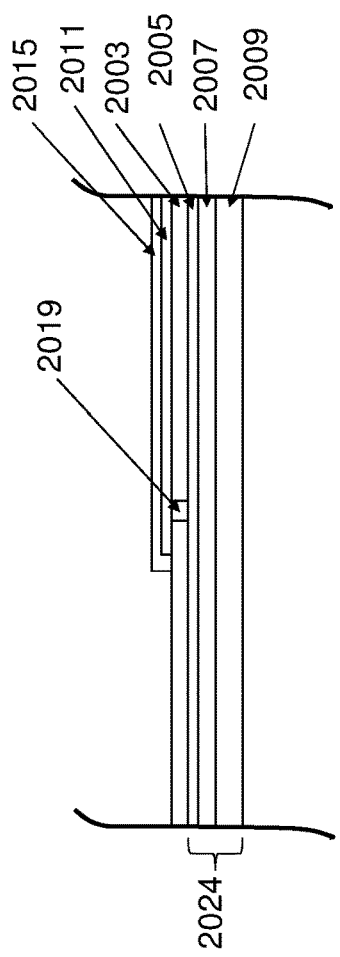
FIG. 22A shows an exemplary (not to scale) sectional view through an active region of an electrode fed by a conductive trace.

For example, FIG. 22A is a section through one variation of an active region of an electrode, showing different layers that may be used to form the active region, including a connector for connecting (and removing). For example, in FIG. 22A, an electrode trace 2011 extends on a top surface of a substrate 2003 (such as a polymeric material). This trace 2011 may be insulated (e.g., by an insulating covering) 2015 and may make an electrical contact with the controller. In this example the electrode is printed on a substrate with the electrical connection being made through the substrate. This is optional; the connection could be made on the same side of the substrate as the rest of the electrode. In this example, an opening through the substrate (e.g., flex circuit), e.g., hole 2019, may include a conductive material (e.g., carbon black, silver, etc.) resulting in electrical communication between the trace 2011 connecting to the controller and a portion of the electrically active region 2024, that (in this example) includes a layer of conductive metal (e.g., Ag) 2005, a layer of sacrificial conductor (e.g., Ag/AgCl) 2007 that completely covers the Ag layer and an outer, skin-contacting layer of hydrogel 2009 that is in electrical contact with the Ag/AgCl layer, and may also completely cover it (or cover it in conjunction with an insulator). The sacrificial Ag/AgCl layer 2007 in this example may also extend beyond the border of the conductive (i.e. Ag) layer 2005 to avoid shorts between the conductive (i.e. Ag) layer and the skin-contacting layer of hydrogel 2009 (i.e. extends beyond it around its entire circumference, including any internal exclusions or holes in the layer, for instance to permit a snap conductor to be placed).

Figure 22C:
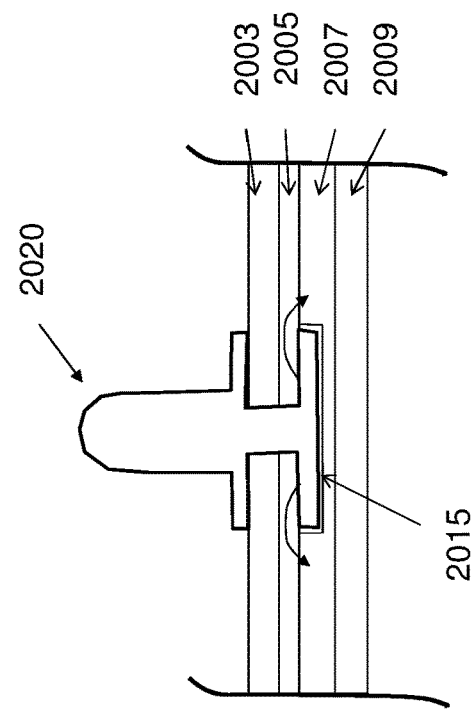
FIG. 22C is a slightly enlarged view of FIG. 22B.
Figure 22B:
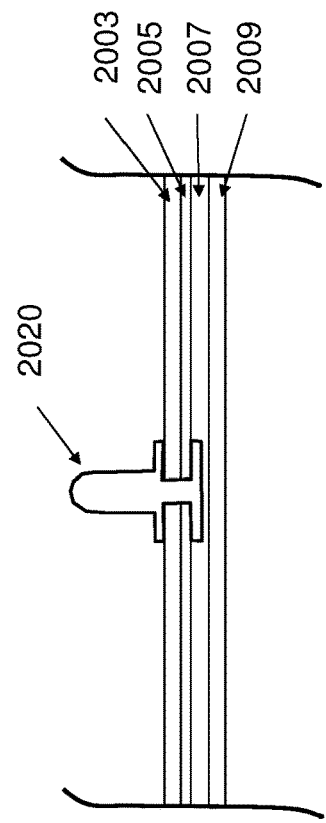
FIG. 22B shows a section view though an active region directly connected to a (snap) connector for coupling to a neurostimulator.

FIG. 22B shows a partial section through a portion of an active region that is electrically connected to an electrical and/or mechanical connector via an indirect connection pathway and thereby connects to an electrical stimulator (e.g., such as a neurostimulator). In some variations the electrode includes an active region that is directly connected to a connector to releasably connect to the controller (e.g., snap, etc.). An example of this arrangement is shown in FIG. 22B and in detail in FIG. 22C, illustrating a snap that may be releasably coupled to a connector for coupling to the controller.

In FIG. 22B the active region of the electrode includes a contact (shown as a snap or pin) for connection to the electrical stimulator (e.g., neurostimulator). In this example, the connector 2020 penetrates the substrate 2003 and a layer of conductive material (shown as a conductive metal, e.g., Ag) 2005 and makes electrical contact with this Ag layer. The bottom of the post or connector 2020 is electrically insulated (visible in FIG. 22C as the insulating layer 2015). A sacrificial layer of Ag/AgCl covers the Ag layer (and the insulated base of the post 2020), and a skin contacting layer of conductive hydrogel 2009 contacts the Ag/AgCl layer. FIG. 22C shows a slightly enlarged view of FIG. 22B, and schematically illustrates the current flowing from the electrical/mechanical connector 2020 into the hydrogel 2009 through the sacrificial Ag/AgCl layer 2007 and the Ag conductive layer 2005. In this example, the connection is configured so that the current does not flow directly into the Ag/AgCl 2007 or hydrogel 2009, but first passes from an upper surface of the connector that is in electrical contact with the Ag layer 2005 and then down into the Ag/AgCl layer 2007 and the hydrogel to contact the user. Thus, in this example, the portion of the connector base in contact with the silver/silver chloride layer is insulated 2015 so that the current primarily passes through the silver layer 2005.

In general, an electrically active region of an electrode portion(s) of the apparatus may include a nonconsumptive conducting layer (e.g., 2005 in FIGS. 22A-22C), a consumptive conducting layer (e.g., 2007 in FIGS. 22A-22C), and a conductive hydrogel layer (e.g., 2009 in FIGS. 22A-22C). In some embodiments, the consumptive layer may be a buffer layer disposed between the nonconsumptive layer and the hydrogel layer. Further, the consumptive layer may extend beyond the boundary of the nonconsumptive layer at each edge of the nonconsumptive layer and may be configured to reduce hydrolysis in the hydrogel layer, such that the consumptive layer donates electrons for redox reactions. Examples of the conductive nonconsumptive layers may include silver, gold, copper, or any other type of conductive metal or non-metallic material, such as carbon or conductive polymers (e.g. poly(3,4-ethylenedioxythiophene). Preferably, the nonconsumptive and consumptive layers include silver. An important feature of the nonconsumptive layer is that any electrochemical reactions occurring in that layer do not cause the quality of the layer as an electrical conductor (i.e. impedance) to change during a transdermal (e.g., transcranial) stimulation. This feature ensures that current delivered to the layer is, for the most part, distributed evenly over its surface first before entering the consumptive layer. In some variations, an additional, higher impedance, layer is disposed between the nonconsumptive layer and the consumptive layer to more evenly spread current across the nonconsumptive layer before entering the higher impedance layer and, subsequently, the consumptive layer. In some embodiments, the nonconsumptive layer experiences reduced consumption, such that the nonconsumptive layer includes silver. Alternatively, the nonconsumptive layer may experience essentially zero consumption, such that the nonconsumptive layer includes carbon. In some embodiments, the nonconsumptive layer experiences reduced consumption since it does not include an anion that can be electrically consumed during electrical stimulation. The nonconsumptive layer may disperse the electrical current over its surface area before the current reaches the consumptive layer (i.e. there is lower impedance within the nonconsumptive layer than between the nonconsumptive layer and the consumptive layer). If the electrical current is not dispersed over the surface area of the nonconsumptive layer before reaching the consumptive layer, the consumptive layer may be overconsumed, such that AgCl becomes Ag(0) in a local area of the consumptive layer surface, causing uneven current distribution and the potential for local hydrolysis and local pH changes that may lead to discomfort in the subject. In embodiments, the consumptive layer is composed of a ratio of silver to silver chloride (Ag:AgCl) for efficient consumption and electrochemistry. Optimal ratios can be selected based on the charge balance of stimulation. In some embodiments, the ratio of Ag to AgCl particles in the consumptive layer may be between 40%:60% to 95%:5%, preferably 65%:35% to 85%:15%. Alternatively, the consumptive layer may include any suitable ratio of Ag:AgCl such that the chloride may be consumed but not depleted during an electrical stimulation session of sufficient length to induce a beneficial cognitive effect in a subject. The AgCl in the consumptive layer is consumed during alternating current or direct current stimulation (DC) because it acts as a sacrificial anode/cathode and is converted to Ag and a Cl$^-$ ion. The Ag+ in the consumptive layer is consumed during alternating current or direct current stimulation (DC) because it acts as a sacrificial anode/cathode and is converted to AgCl. In some embodiments, if the consumptive layer does not fully cover the dermal side of the nonconsumptive layer, the current may travel directly to the hydrogel layer and cause a site of high current density, for example a current hotspot. In some embodiments, the conductive hydrogel layer ensures that the current is transmitted substantially evenly to the skin of a user. Further, the hydrogel layer creates a uniform connection between the multi-electrode assembly and the skin of a user.

In any of the electrode apparatuses described herein, an additional layer may be positioned between the conductive layer in electrical contact with the connector (e.g., snap connector) and the sacrificial anode/cathode layer in contact with the hydrogel. The additional layer may be a material that is less conductive than the adjacent conductive metal (e.g., Ag) layer and sacrificial (e.g., Ag/AgCl) layer, or even a weakly insulating material. In this example, the material is carbon, although other materials may be used. In general this layer may be less conductive than the layers immediately above (e.g., Ag) and below (e.g., Ag/AgCl). For example, FIGS. 22D-22F illustrate another variation of section through an active region of an electrode apparatus, showing different regions that may be used to form the active region and including an additional carbon layer. In FIG. 22D, the electrode trace 2011 extends on a top surface of a substrate 2003 (such as a polymeric material appropriate for use in a flexible circuit). This trace 2011 may be insulated (e.g., by an insulating layer 2015). An opening through the flex circuit (e.g., hole 2019) may include a conductive material (e.g., carbon black, silver, etc.) making an electrical communication between the trace 2011 and a portion of the electrically active region 2024, that includes a layer of conductive metal (e.g., Ag) 2005, a layer (e.g., carbon) having a lower conductance than the adjacent layers 2044, a covering layer of sacrificial Ag/AgCl 2007 that completely covers the Ag layer and it itself covered by the carbon layer 2044, and an outer, skin contacting layer of hydrogel 2009 in electrical contact with the Ag/AgCl layer.

In any of the electrode apparatuses described herein, the first conductive layer (e.g., a Ag layer) connects to the connector (e.g., pin, snap, clamp, etc.) and thus the electrical stimulator. This first conductive layer is separated from the sacrificial layer (e.g., Ag/AgCl layer) that connects to the gel (e.g., hydrogel) by the intermediate, less conductive layer. This less conductive layer may also be referred to as a weakly conductive layer, a weakly insulating layer, or a more resistive layer (all in reference to the adjacent first conductive layer and sacrificial layer). In general, this weakly conductive layer has an electrical conductance that is lower than either the adjacent first conductive layer or the sacrificial layer, although the electrical properties of the sacrificial layer may change with use. Thus, in general the weakly conductive layer may be more resistive than the first conductive layer; for example, the weakly conductive layer may have a resistivity that is greater than 3×, 4×, 5×, 6×, 7×, 8×, 9×, 10×, 15×, 20×, etc., the resistivity of the first conductive layer. In some variations, the resistance of the weakly conductive layer is greater than 5× the resistance of the first conductive layer that it covers. In general, each successive layer distal from the flexible substrate (i.e. a polymeric material appropriate for use in a flexible circuit) extends beyond the edge of the more proximal layer along its entire circumference to ensure that current cannot short between non-successive layers.

The weakly conductive layer may be formed of any appropriate material having the electrical properties described herein. For example, the weakly conductive layer may include carbon. For example, the weakly conductive material may be a polymeric material (including rubbers, polyvinyl chlorides, etc.) that is mixed with or incorporates carbon (e.g., carbon particles), etc.

FIG. 22E shows a partial section through a portion of another active region that is in electrical contact with a connector configured to couple with the controller of the electrical stimulator (e.g., the electrical and/or mechanical connector that contacts with the neurostimulator). The electrode may include an active region that is connected to the connector as shown in FIG. 22E and in detail in FIG. 22F. In this example, the active region of the electrode includes a contact (shown as a snap or pin) for connection to the electrical stimulator (e.g., neurostimulator). The connector 2020 penetrates the substrate 2003 as well as a layer of conductive material (shown as a conductive metal, e.g., Ag) 2005 and (in some variations) a layer of less conductive material (e.g., carbon) 2044, to make electrical contact with this Ag layer. The bottom of the post/connector 2020 is electrically insulated (shown in FIG. 22E as an insulating layer 2015). In this example, the Ag layer 2005 is separated from the sacrificial layer of Ag/AgCl 2007 by a less conductive (than either the Ag or Ag/AgCl layers) layer of carbon 2044, and a skin-contacting layer of conductive hydrogel 2009 contacts the Ag/AgCl layer 2007. FIG. 22F shows a slightly enlarged view of FIG. 22E, and schematically illustrates the current flowing from the electrical/mechanical connector 2020 into the hydrogel 2009 through the sacrificial Ag/AgCl layer 2007, less conductive layer 2044 and the conductive Ag layer 2005. In this example, current does not flow directly into the Ag/AgCl 2007 or hydrogel 2009, but first passes from an upper surface of the connector that is in electrical contact with the Ag layer 2005, either directly (not shown) or through the less conductive (e.g., carbon) layer 2044, and then flows down into the Ag/AgCl layer 2007 and the hydrogel to contact the user.

The optional less conductive layer 2044 described above may be helpful to spread the current as it moves from the highly conductive metal layer such as the Ag layer 2005 shown in FIGS. 22A-22F to the sacrificial layer (e.g., Ag/AgCl layer 2007) and into the hydrogel. In effect, this carbon layer (or similar less-conductive layer) may make the electrodes much more comfortable for the user to wear them, even when delivering relatively high intensity current signals, by improving the uniformity of current density and electrochemistry occurring in the consumptive layer and/or hydrogel.

In some embodiments, the electrode apparatus (flexible electrode assembly) may include an adhesive component. The adhesive component may be configured to couple the electrode apparatus to a body portion of a user or any other device or system. An adhesive component may surround and/or be adjacent to the boundary of the consumptive layer. In some embodiments, the adhesive component and the three layers (consumptive, nonconsumptive, and hydrogel) of the electrode active region may be substantially the same thickness, such that substantially all areas of the flexible assembly may be flush with the skin of a user. In some embodiments, the hydrogel layer may extend slightly beyond the adhesive layer so that the hydrogel makes a more uniform contact through slight compression when the electrode is adhered to the skin.

Any of the electrodes formed as described herein may include a substrate and a connector (e.g., pin) as mentioned above, for removably connecting to the rest of the apparatus; thus the electrodes may be electrode pads that are disposable and/or easily replaceable by a removable attachment. The substrate (e.g., polymeric insulating material substrate, such as a flexible substrate, e.g., Kapton) may be connected to the apparatus and then coupled to the skin of the user. The electrode may be adhesively held in addition to or alternative to a friction hold, e.g., a headband, helmet, head scarf, or any other type of wearable device. For example the electrode may be connected to a body configured to fit within a portion of the pinna of the user's ear, as described above.

As described above, any of these apparatuses may include two or more electrodes (active regions) for electrical stimulation.

As mentioned any of these apparatuses may optionally or additionally include one or more sensors, safety features, or identification features or devices embedded in the flexible substrate and/or integrated with the controller (e.g., in the PENS neurostimulator). One or more sensors may include an accelerometer, thermometer, gyroscope, GPS, pH sensor, one or more biosensors, or any other type of sensor. One or more safety features may include an automatic off trigger, for example when the current reaches a certain threshold, when the temperature and/or pH of the device exceeds a threshold, or when the controller does not contain enough power to complete an entire TES session. One or more identification features may include a Bluetooth beacon, an RFID tag, a barcode, a near-field communication device, a biometric sensor for reading, for example a fingerprint of a user, or any other type of identification feature or device, including the capacitive identification system described above.

Figure 23:
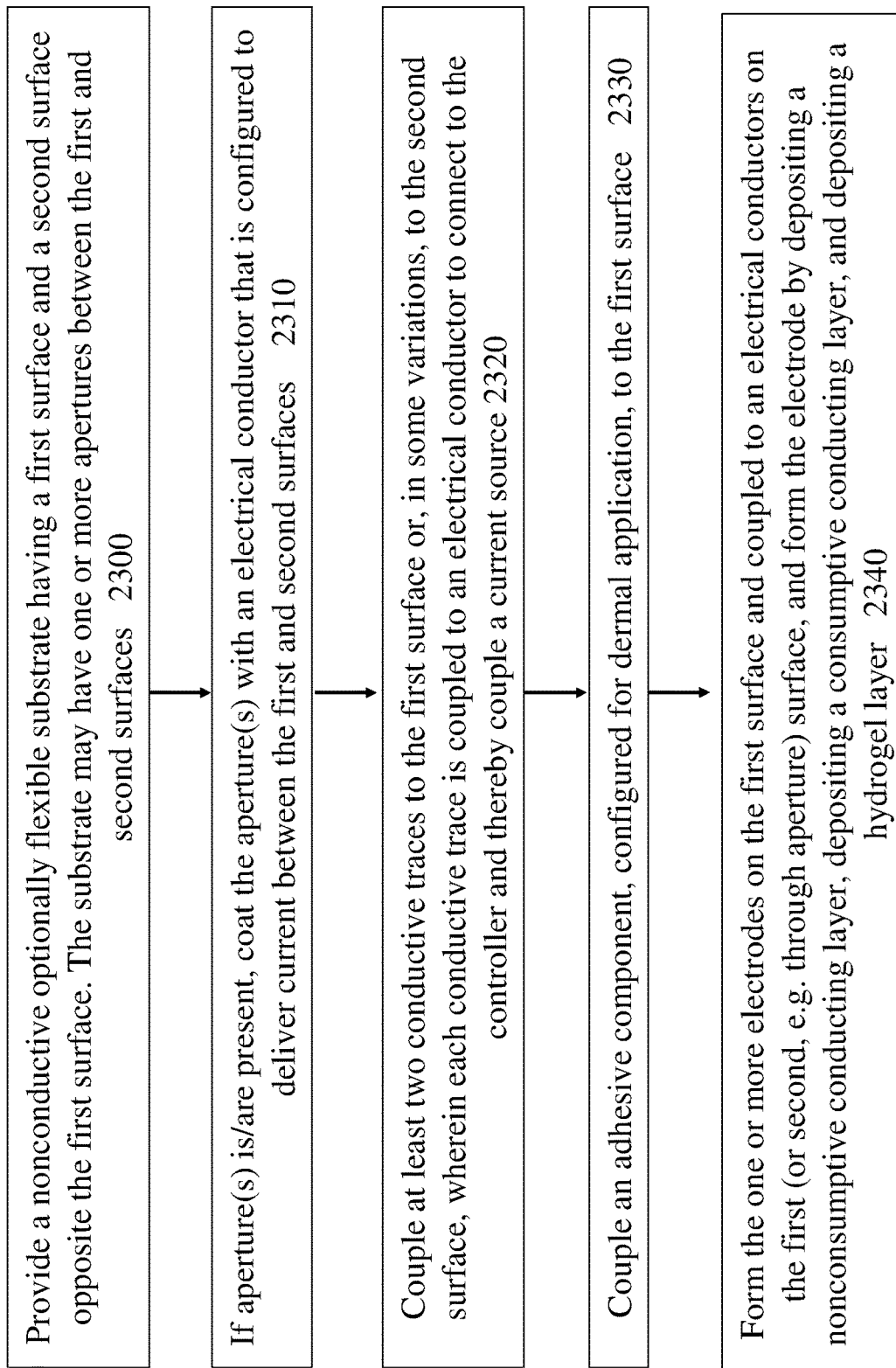
FIG. 23 schematically illustrates one method of forming an electrode apparatus such as a PENS electrode apparatus.

FIG. 23 illustrates one method of making an electrode portion (including a disposable electrode portion) of any of the apparatuses described herein. In this example a nonconductive (e.g., optionally flexible) substrate 2300 having a first surface and a second surface opposite the first surface may be coated with the multiple layers to form the electrode. In some variations the electrical connection to the controller may be made through a via or hole in the substrate, from the opposite side of the substrate. This hole may be filled with a conductive material so that the apertures are at least partially filled (and more preferentially completely filled) with an electrical conductor that is configured to deliver current between the first and second surfaces 2310. Alternatively, when the electrode active region is formed on the same surface as the connecting conductive trace, this step may be unnecessary. When forming on the opposite surface, the connector may be formed on the second surface, such that a conductive trace is coupled to the electrical conductor on the second surface. In either example, the conductive trace is configured to couple a current source to the electrical conductor 2320. An adhesive component, configured for dermal application, may then be placed (e.g., coated) to the first surface 2330; and at least one electrodes may be formed or connected to the first surface and coupled to the electrical conductor on the first or second surface 2340. Connecting or forming the electrode may include depositing a nonconsumptive conducting layer, depositing a consumptive conducting layer, and depositing a hydrogel layer, such that the consumptive layer is a buffer layer disposed between the nonconsumptive layer and the hydrogel layer that extends beyond the boundary of the nonconsumptive layer at each edge of the nonconsumptive layer and is configured to reduce hydrolysis in the hydrogel layer.

One embodiment of manufacturing an electrode apparatus for electrical stimulation to modulate a cognitive function may therefore generally include forming an aperture through a nonconductive flexible substrate having a first surface and a second surface opposite the first surface. In general, the flexible substrate may include polyimide, volara foam, or any other type of nonconductive material. The flexible substrate may be poured, dispersed, or otherwise positioned in a mold. The mold may include two or more protrusions, such that the flexible substrate, once set, includes two or more apertures. The flexible substrate in the mold may be thermoset and/or cured (e.g. form cross-links) by heat, a chemical reaction, and/or irradiation. In some embodiments, the cured flexible substrate may include a higher melting temperature than the temperature used to cure it. Thus, the cured flexible substrate may not be re-melted and/or deformed with the application of low intensity heat, such as the low intensity heat experienced during electrical stimulation. In some embodiments, additional components may be positioned in the flexible substrate before curing the flexible substrate, such that the additional components are embedded in the flexible substrate. The apertures formed in the flexible substrate may function to electrically connect the second surface with the first surface, such that the first surface may deliver electrical stimulation to a body portion of a user, as described above.

An alternative manufacturing process may use a substrate that is cut, severed, or otherwise carved from a large sheet or the substrate may be poured, dispersed, or otherwise positioned in a mold. The substrate may be rigid, semi-rigid or flexible and may include one or more electrode areas and a thin structure that has at least one conductive trace, e.g., on the first (nondermal) side, or in an internal layer insulated on both dermal and nondermal sides, for delivering current from a connector to a portion of the substrate containing the electrode pad/active region. Electrode layers may be printed on the first (dermal facing) side of the substrate. Hydrogel pieces having the same or very similar shape to the electrode areas may be placed over them. Adhesive regions adjacent to or surrounding a hydrogel and electrode area may also be placed on the first dermal facing side of the flexible assembly. Multiple sheets may be bonded, glued, or otherwise fastened together to form the electrode assembly, and conductive connections to the controller (e.g., PENS electrical stimulation controller) may be made with connectors such as male studs or snap connectors riveted through flexible substrate layers. Each snap connector may be conductively connected to one of the electrode areas either directly or via a conductive path printed on the substrate.

In some embodiments, the electrode layers may be coated, silkscreened, painted, or printed (e.g., with a conductive metal). For example, the conductive metal may include gold, silver, copper, aluminum, or any other type of conductive material. A method of manufacturing an electrode assembly may include coupling a conductive trace to the first or second surface, such that the conductive trace is coupled to an electrical conductors/connector and configured to couple with the current source (controller). A conductive trace may be coupled to the surface by printing, silk-screening, soldering, welding, gluing, or any other type of coupling process. In some embodiments, multiple conductive traces may be electrically connected to the same electrode, such that each trace electrically controls a subset (e.g. electrode area) of the electrode.

Further, a method of manufacturing an electrode portion of a PENS apparatus (including a disposable/removable electrode) may include coupling an adhesive component, configured for dermal application, to the first surface of the electrode. The adhesive component may be adhered, secured, coupled, fastened, bonded, or otherwise attached to the (e.g., flexible) substrate adjacent to and/or surrounding the electrode active region, or (if appropriately conductive) overlapping it. In some embodiments, an adhesion promoter may be used to help couple the adhesive component to the flexible substrate. Once coupled to the flexible substrate, the adhesive component may be flush with and/or not extend beyond the height of the other components coupled to the flexible substrate. Further, in some embodiments, the adhesive component may include a protective layer on the skin facing side, such that a user would need to peel the protective layer off before adhering the adhesive component to a body portion of the user. The protective layer may include plastic, synthetic rubber-like material, wax paper, or any other type of material that can be removably detached from the adhesive without significantly reducing dermal adhesion.

A method of manufacturing a flexible transdermal multi-electrode assembly for electrical stimulation of a neural target may also include forming and/or bonding the electrode to the first surface and coupling it to an electrical conductor on the second surface, such that the step of bonding the electrode further includes depositing a nonconsumptive conducting layer, depositing a consumptive conducting layer, and depositing a hydrogel layer, such that the consumptive layer is a buffer layer disposed between the nonconsumptive layer and the hydrogel layer that extends beyond the boundary of the nonconsumptive layer at each edge of the nonconsumptive layer and is configured to reduce hydrolysis in the hydrogel layer. The nonconsumptive and consumptive layers may be printed or silkscreened on the substrate. The silver ink in the nonconsumptive and consumptive layers may include 60-70% silver solids plus ethylene glycol and additional solvents. The ethylene glycol and additional solvents are flashed off while drying each of the layers after depositing each of the layers. Alternatively, other methods of printing the silver on the substrate may be used. In some embodiments, the method may further include applying an adhesion promoter to enhance the coupling of the nonconsumptive and consumptive layers to the substrate. In some variations the substrate forms a part of the body of the earbud or insertable piece held in the user's ear.

Waveform Controller

Figure 29B:
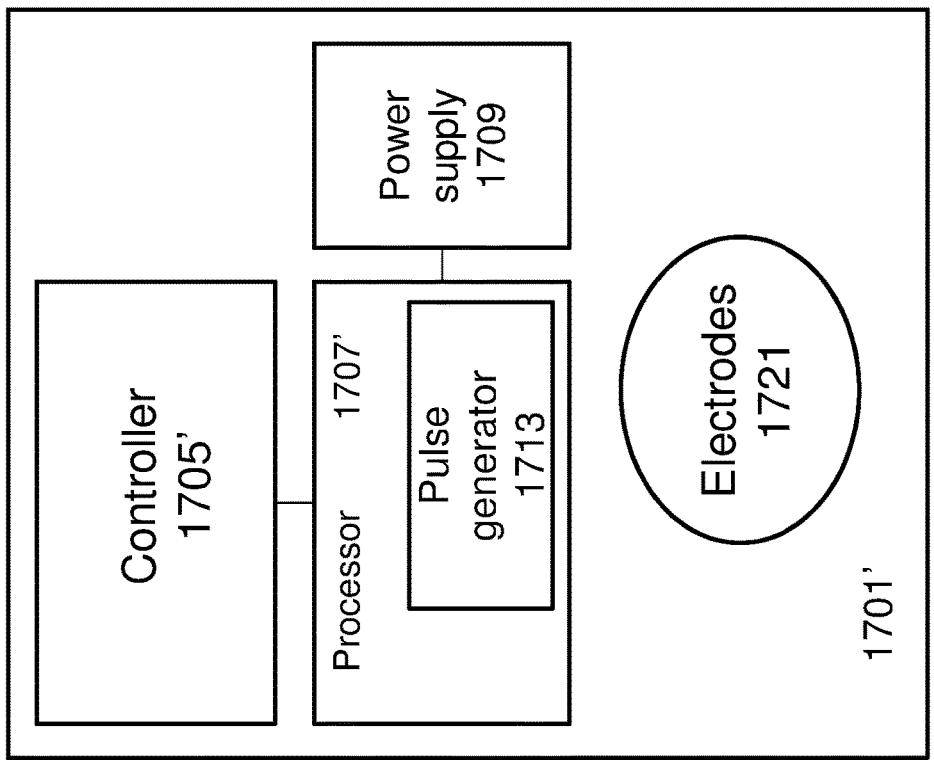
FIG. 29B is a schematic illustration of another example of a system in which the controller and processor are directly connected, rather than wirelessly connected.
Figure 29A:
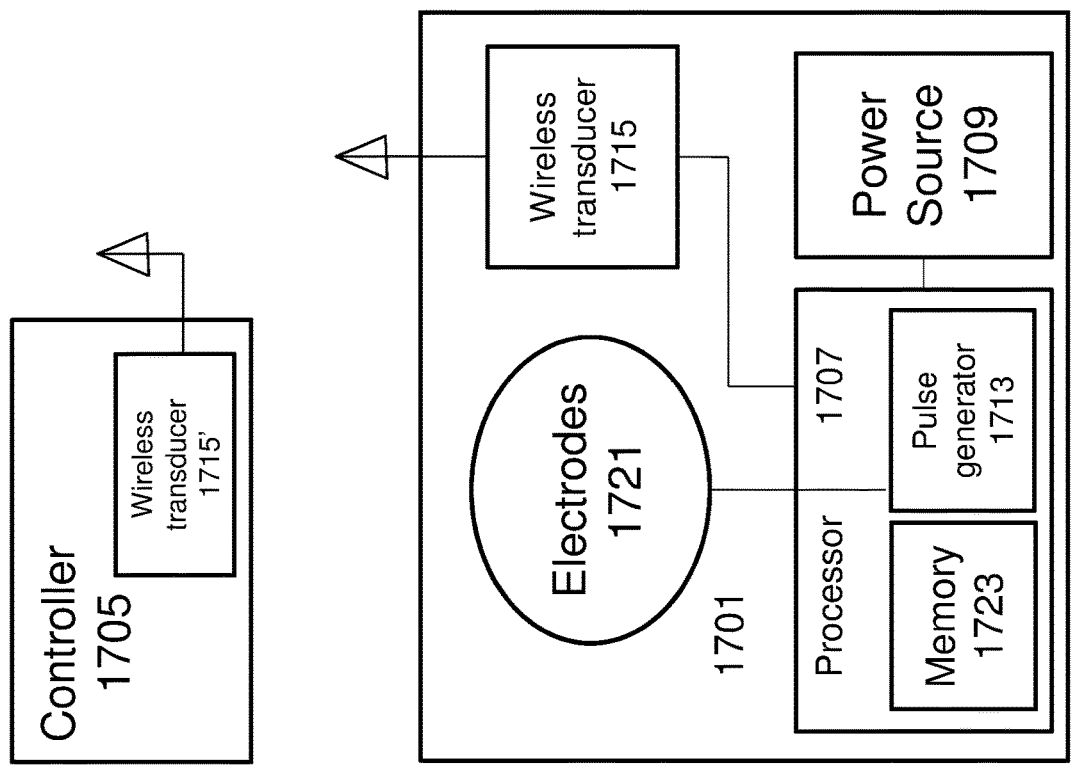
FIG. 29A is a schematic illustration of one example of an apparatus (e.g., system) including a wireless controller that sends command instructions, including ensemble waveform information, to a wearable neurostimulator having a processor adapted to receive and interpret this information, which may be sent in an abbreviated and efficient message encoding system.

Also described herein are methods and apparatuses for efficient, compact and rapid communication of control currents (e.g., ensemble waveforms) including transmitting and receiving information to form the applied waveforms for evoking the appropriate cognitive response. For example, control information may be transmitted to a controller including a waveform controller of the wearable neurostimulator from a separate device (e.g., smartphone, wearable electronics, etc.). The controller may be part of the wearable apparatus or remotely located relative to the wearable neurostimulator. FIG. 29A is a schematic illustration of a wearable neurostimulator 1701 such as the ones described herein which may wirelessly receive control information (e.g., ensemble waveform information and/or command controls from a waveform controller 1705). In this example, the wearable neurostimulator includes at least two electrodes 1721 that are integral with or connectable to the neurostimulator 1701, and a processor 1707 that connects to wireless communication circuitry 1715 (e.g., wireless transducer), a power source 1709, and a pulse generator 1713 to apply the waveforms via the electrodes 1721. The processor may also include a memory 1723 having one or more registers for storing waveform information, including one or more of a: a current and/or next component waveform. The waveform controller 1705 may also include wireless communication circuitry 1715' for transmitting (and/or receiving) control information, including component waveform control information.

The processor 1707 is generally configured to receive and handle waveform information. Specifically, the processor described herein is configured to operate in real-time to communicate with and receive information from the waveform controller. The waveform controller may transmit (e.g., in real-time or near-real time) sequential component waveforms from the series of waveforms forming an ensemble waveform; to achieve this, the controller and processor share a specific communication architecture that allows the rapid and reliable transmission of component waveforms to the wearable apparatus, allowing the wearable apparatus to deliver the potentially complex ensemble waveform in an energy-efficient and reliable manner. In this example in FIG. 28A, the PENS apparatus may include a body portion that is worn so that the electrode(s) are in connection with one or both ears. The wearable apparatus 1701 may be formed to fit into, over or around the ear, and may connect wirelessly (or via a cable/wire, not shown) to the controller that determines the waveform shape and pattern to be applied (via controller 1705). The separate controller may be part of a smartphone or other wearable electronics.

Specifically, the controller may transmit one or more control codes that may be received by the processor. A variety of control codes may be transmitted, for controlling any of the functions of the wearable neurostimulator, including self-reporting codes (instructing the device to run and/or return diagnostic information including power charge status), LED controls, pairing controls, power-down controls, and the like. In particular, the controller may transmit control codes instructing the neurostimulator to receive waveform information and in particular component waveform information. A command control may tell the processor to prepare to receive and/or deliver a new component waveform, or it may tell the processor to edit or modify an existing component waveform; the command control may also specific the number of segments to expect for the new component waveform or which segments in a stored (including currently running) component waveform to modify.

For example, a first command message (e.g., "new waveform" message/command control) may instruct the processor of the wearable apparatus to prepare a memory register ("shadow register") to receive waveform information. This message may indicate that the processor should start a "new" component waveform or use a component waveform already stored (which may be the waveform most recently delivered by the device). In general, the command messages may be structured to include a message identifier (message ID) that indicates what the message will contain (e.g., which may be recognized by the processor via a look-up table or other mechanism), and/or routing information (e.g., destination and/or source endpoints), and a message payload, which may be the message, such as the new waveform message or the waveform segment message discussed below. FIG. 29B illustrates another variation including a processor 1707' in which the controller 1705' is integrated into the wearable portion 1701'.

Other variations of TES neurostimulation apparatuses that are not integrated, but may include external power and/or control are also described herein, as mentioned above. For example, FIGS. 30A-31B illustrate variations of a TES apparatus in which the electrode assembly 486, 485 is coupled via connectors (shown as snaps, but any connector may be used) and configured to be worn in, over, or around the ear, so that one or more electrodes are in contact with the pinna of the ear. A connector such as a snap connector or other mechanical and electrical connectors may be connected to a cable 499, and (through the cable) to a hand-held or otherwise portable computing device 490, such as a general-purpose smartphone (e.g., iPhone™ Android™, Google phone) or other portable or wearable electronics. The portable computing device may function by running software and/or firmware for controlling operation of the neurostimulator, including in some variations, selecting and preparing the PENS waveforms (ensemble waveforms) to be delivered, confirming connection of the electrode assembly to the user, and/or confirming the type/state of the electrode apparatus. Although the electrode apparatus may be single-use or limited-use, and may include no or very little of the control circuitry, the cable 499 may be configured as a "smart" cable, which includes control circuitry receiving power and control information from the portable computing device (control device) and forming the waveform(s) for delivery by the electrode assembly. The smart cable may also be referred to herein as a TES (or PENS) cable neurostimulator, and it may include all or some of the control circuitry described above, including at least amplification circuitry for amplifying the power provided by the control device to the waveforms.

In FIG. 30A, the cable neurostimulator 499 is configured to plug into the control device 490, so that it may drive delivery of waveforms appropriate for the type of electrode assembly (e.g., calm 485 or energy 486). In FIG. 30A, the proximal end of the TES cable neurostimulator includes a housing region which may house some of the TES control circuitry as well as forming the connector (e.g., a "Lightning" type connector when connecting to an appropriate iPhone). The distal end of the TES cable neurostimulator may include a set of connectors (e.g., snap connectors, magnetic connectors, multi-pin connectors, concentric connectors, etc.) complimentary to the connectors on the electrode assembly. In FIG. 30A the connectors are held in a fixed spacing appropriate to mate with the mechanical/electrical connectors on the electrode assembly. FIG. 30B shows another example of the distal end region of an apparatus in which the connectors are separately positionable relative to each other (the distance separating them is not to scale; for example when connecting to both ears on each side of a user's head the separate cable regions may be longer). In other variations of the cable neurostimulator, a larger housing containing control circuitry may be present at or near the distal end of the cable (i.e. near the electrode assembly) or in-line along the cable, similar to how music controls may be present along the cable of earbuds.

Figure 30C:
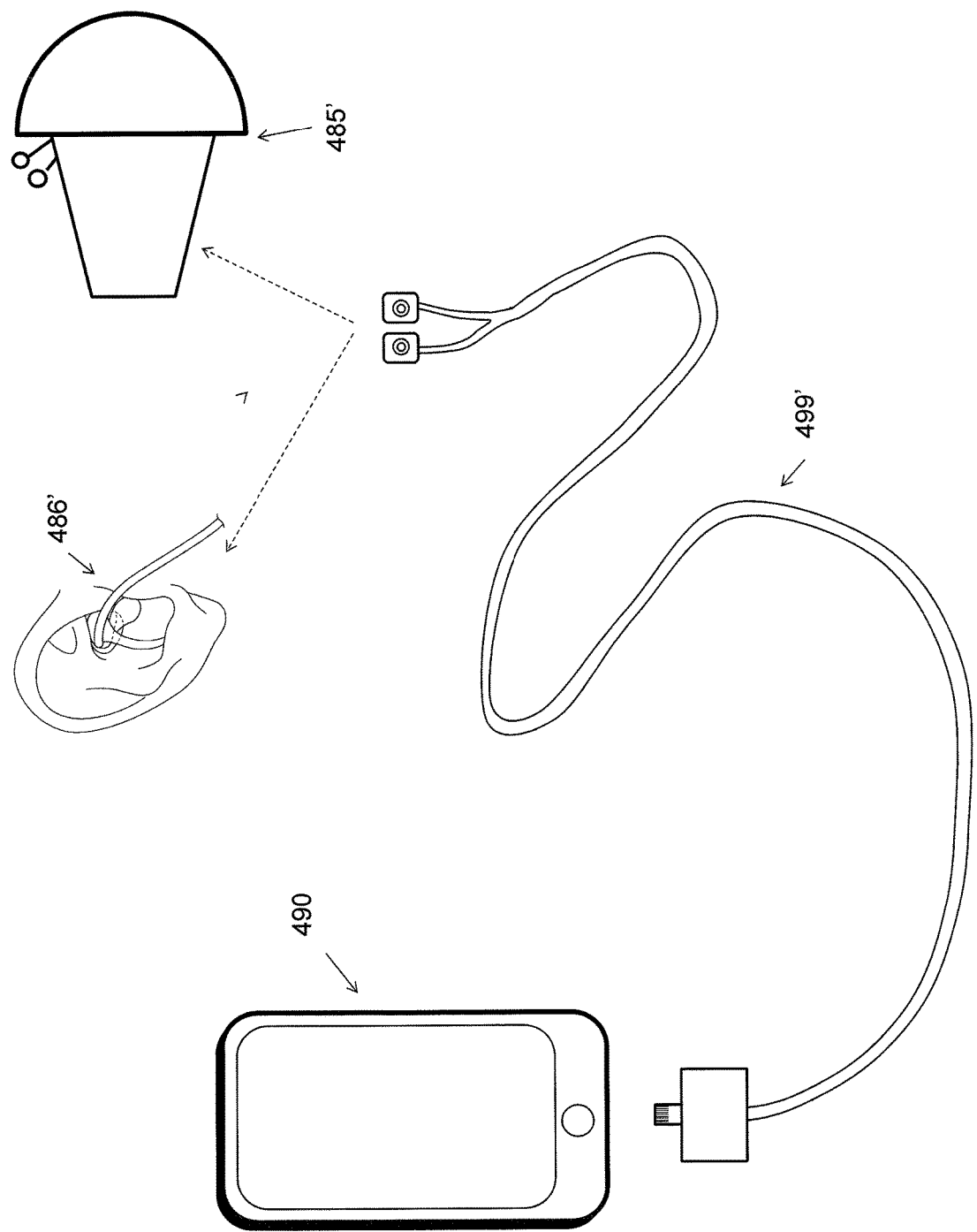
FIG. 30C illustrates another example of a TES cable neurostimulator connecting to another pair of electrode assemblies having connectors on a region of the electrode assembly that is configured to be worn on or in a user's pinna (outer ear).

FIG. 30C illustrates an alternative view of a cable neurostimulator 499' connectable to two alternative configurations of PENS electrode assemblies 485', 486'. In this example, the cable neurostimulator is configured to be connected to a region of the electrode assembly that is worn away from the face (e.g., on the back of the neck and/or behind the ear).

Figure 31B:
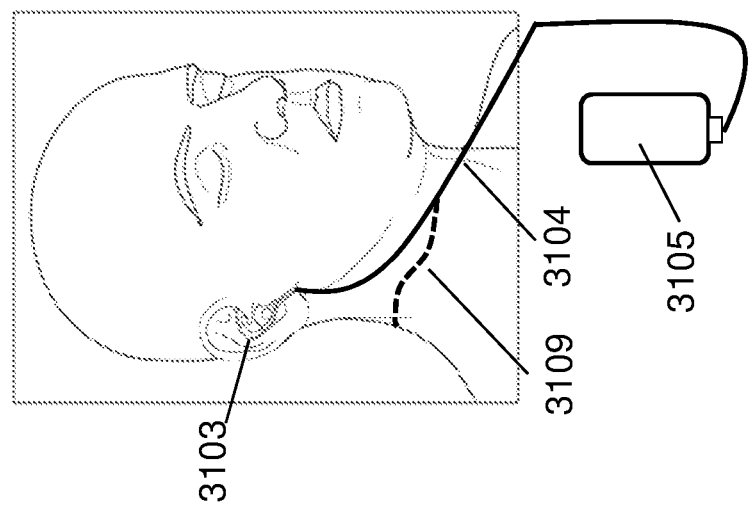
FIG. 31B illustrates a pinna TES embodiment with an electrode apparatus in one ear. A second electrode may optionally connect to another (non-ear) region of the skin on the subject's body (dashed line), or it may also connect to the same ear.
Figure 31A:
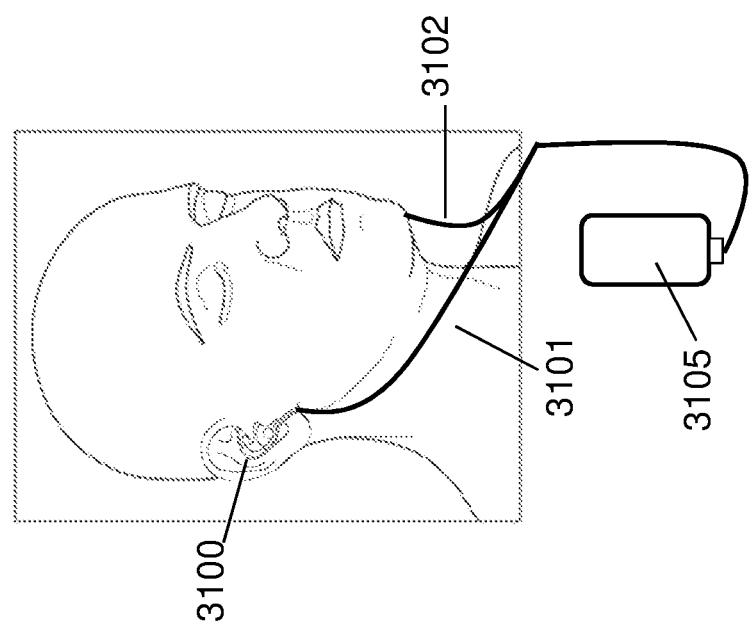
FIG. 31A illustrates a pinna TES neurostimulator with an electrode in each ear, controlled by a smartphone.

FIGS. 31A and 31B show connection between some variations of the PENS apparatuses described herein (e.g., 3100, 3103) connected to the skin of a pinna region of one or both ears (FIGS. 31A and 31B, respectively). A cable 3101, 3102, 3104, 3109, such as but not limited to the "smart" cables shown in FIGS. 30A-30C may be used to connect to a source of control information and/or power, and in some variations the controller, such as a smartphone or wearable electronics 3105. In FIG. 31B the PENS apparatus connects to both of the user's ears for delivery of current between the two electrodes (one on each ear). For comparison, a system such as that shown in FIGS. 30A-30B is illustrated worn on a user in FIG. 31A. The dashed line 3109 shows the optional separate cable portion for connecting a second electrode to a separate portion of the body (e.g., the back of the neck, shoulder, head, etc.).

Embodiments of External Ear TES

The apparatuses and methods described herein may include methods of modifying a subject's cognitive state to induce or enhance attention, alertness, or mental focus or to induce or enhance a calm or relaxed mental state as described above. For example, as described above, a method may include: activating a portable transdermal electrical stimulation (TES) applicator to deliver a pulsed transdermal electrical stimulation having a frequency of 250 Hz or greater and an intensity of greater than 0.25 mA between a first and second electrode positioned on the subject's pinna so that at least one of the first and second electrodes are in contact with the subject's meatus; and modifying the subject's cognitive state by applying the biphasic transdermal electrical stimulation between the first and second electrodes for 10 seconds or longer. In some variations the electrodes may be positioned bilaterally with unipolar electrodes or unilateral with a bipolar electrode. In some variations, the electrical stimulation waveform may be asymmetric and biphasic.

For example, a method as described herein may use at least one of the first and second electrodes in contact with the meatus for modifying a subject's cognitive state with a TES stimulus having a frequency of 250 Hz or greater and an intensity greater than 0.25 mA between the first and second electrode on the subject's pinna to enhance attention, alertness, or mental focus during skill training, such as in the learning of a computer language or foreign language.

As mentioned above, enhancing cognition includes enhancing training or learning, e.g., reducing time to train and/or learn, increase retained knowledge/skills, etc.

For example, a method as described herein may include using at least one of the first and second electrodes in contact with the meatus for modifying a subject's cognitive state with a TES stimulus having a frequency of 250 Hz or greater and an intensity greater than 0.25 mA between the first and second electrode on the subject's pinna to enhance attention, alertness, or mental focus during skill training, such as in the learning of an autonomous vehicle or unmanned aerial vehicle.

In some variations the methods described herein include methods of using at least one of the first and second electrodes in contact with the meatus for modifying a subject's cognitive state with a TES stimulus having a frequency of 250 Hz or greater and an intensity greater than 0.25 mA between the first and second electrode on the subject's pinna to enhance attention, alertness, or mental focus during skill training, such as learning proficiency on a weapon like marksmanship training.

A method as described above may include using at least one of the first and second electrodes in contact with the meatus for modifying a subject's cognitive state with a TES stimulus having a frequency of 250 Hz or greater and an intensity greater than 0.25 mA between the first and second electrode on the subject's pinna to enhance attention, alertness, or mental focus during learning of information that may be presented through digital media, such as streaming audio or video information from a tablet, phone, computer, screen, or across a network.

Any of the apparatuses and methods described herein may be used to treat a sleeping disorder, or generally to improve sleep (even in the absence of a sleep disorder), including reducing sleep onset, increasing sleep duration, etc. For example, a method as described may include using at least one of the first and second electrodes in contact with the meatus for modifying a subject's cognitive state (e.g., improving the subject's sleep) with a TES stimulus having a frequency of 250 Hz or greater and an intensity greater than 0.25 mA between the first and second electrode on the subject's pinna to induce a state of relaxation for inducing sleep and/or for the treatment of sleep disorders. In some variations, these methods or apparatuses may be used to treat sleep apnea. For example, a method as described herein may include using at least one of the first and second electrodes in contact with the meatus for modifying a subject's cognitive state with a TES stimulus having a frequency of 250 Hz or greater and an intensity greater than 0.25 mA between the first and second electrode on the subject's pinna to induce a state of relaxation to treat sleep apnea.

As mentioned above, any of these methods and apparatuses may be used for treating a disorder such as, but not limited to, tinnitus or other auditory dysfunction. For example, a method as described herein may include using at least one of the first and second electrodes in contact with the meatus for modifying a subject's cognitive state with a TES stimulus having a frequency of 250 Hz or greater and an intensity greater than 0.25 mA between the first and second electrode on the subject's pinna to treat tinnitus or auditory dysfunction.

In some variations the methods and apparatuses described herein may be used for treating headache. For example, a method as described may include using at least one of the first and second electrodes in contact with the meatus for modifying a subject's cognitive state with a TES stimulus having a frequency of 250 Hz or greater and an intensity greater than 0.25 mA between the first and second electrode on the subject's pinna to induce a state of relaxation for treating headache.

These methods and apparatuses may also or alternatively be useful for treating pain, such as one or more of: rheumatoid arthritis, arthritis, headache, and general pain. For example, a method as described herein may use at least one of the first and second electrodes in contact with the meatus for modifying a subject's cognitive state with a TES stimulus having a frequency of 250 Hz or greater and an intensity greater than 0.25 mA between the first and second electrode on the subject's pinna to induce a state of relaxation for treating inflammatory conditions or pain conditions like rheumatoid arthritis, arthritis, headache, and general pain.

Any of these methods and apparatuses may be used in combination with one or more chemical agents (e.g., drugs). In particular, the methods and apparatuses described herein may be used in conjunction with one or more pharmaceutical agents such as a psychotropic or psychedelic drug. The use of a chemical agent in conjunction with the methods described herein may enhance, modulate, modify and/or amplify the effect of either the drug or the electrical stimulation alone. The drug may be administered before, during or after the application of electrical energy through the subject's pinna as described herein. For example, described herein are methods of using at least one of the first and second electrodes in contact with the meatus for modifying a subject's cognitive state with a TES stimulus having a frequency of 250 Hz or greater and an intensity greater than 0.25 mA between the first and second electrode on the subject's pinna to induce a state of relaxation prior to, during, or after the use of psychotropic or psychedelic drugs.

As described above, enhancing cognition may include reducing anxiety and/or treating depression. For example, the methods described herein may be used to treat anxiety. A method as described herein may include using at least one of the first and second electrodes in contact with the meatus for modifying a subject's cognitive state with a TES stimulus having a frequency of 250 Hz or greater and an intensity greater than 0.25 mA between the first and second electrode on the subject's pinna to induce a state of relaxation to treat anxiety. In some variations, these methods or apparatuses may be used to treat depression. For example, a method as described herein may include using at least one of the first and second electrodes in contact with the meatus for modifying a subject's cognitive state with a TES stimulus having a frequency of 250 Hz or greater and an intensity greater than 0.25 mA between the first and second electrode on the subject's pinna to induce a state of relaxation to treat depression.

In some variations enhancing cognition may include reducing the effects of substance abuse (including addiction-related disorders). For example, a method as described herein may include using at least one of the first and second electrodes in contact with the meatus for modifying a subject's cognitive state with a TES stimulus having a frequency of 250 Hz or greater and an intensity greater than 0.25 mA between the first and second electrode on the subject's pinna to induce a state of relaxation to treat substance abuse disorder or addition.

Enhancing cognition may include improving mental health generally, including increasing feelings of well-being. For example, a method as described herein may include using at least one of the first and second electrodes in contact with the meatus for modifying a subject's cognitive state with a TES stimulus having a frequency of 250 Hz or greater and an intensity greater than 0.25 mA between the first and second electrode on the subject's pinna to induce a state of relaxation to improve mental health or well-being.

Any of the methods and apparatuses described herein may be used for treating a disorder such as post-traumatic stress disorder (PTSD) and/or treating post-traumatic stress. For example, a method as described herein may include using at least one of the first and second electrodes in contact with the meatus for modifying a subject's cognitive state with a TES stimulus having a frequency of 250 Hz or greater and an intensity greater than 0.25 mA between the first and second electrode on the subject's pinna to induce a state of relaxation to treat post-traumatic stress disorder or post-traumatic stress.

As described above, any of the methods and apparatuses described herein may be used to treat hypertension and/or high blood pressure. For example, a method as described herein may include using at least one of the first and second electrodes in contact with the meatus for modifying a subject's cognitive state with a TES stimulus having a frequency of 250 Hz or greater and an intensity greater than 0.25 mA between the first and second electrode on the subject's pinna to induce a state of relaxation to treat hypertension or high blood pressure.

Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of inducing or enhancing attention, alertness, and/or mental focus, the method comprising:
    placing a first electrode of a portable transdermal electrical stimulation (TES) applicator into a subject's first ear in contact with a first pinna, and placing a second electrode of the portable TES applicator into the subject's second ear in contact with a second pinna, wherein the first and second electrodes include a conductive hydrogel that contacts the skin of the subject;
    activating the TES applicator to deliver pulsed electrical stimulation between the first and second electrodes at an intensity of 2 mA or greater, a duty cycle of greater than 50% and a frequency of between 200 Hz and 2 kHz; and
    delivering the pulsed electrical stimulation between the first and second electrodes for 10 seconds or longer to enhance attention, alertness, and/or mental focus without causing discomfort caused by the pulsed electrical stimulation.

2. The method of claim 1, wherein placing comprises placing the first and second electrodes so that the first and second electrodes are held in the subject's first and second ears, respectively, by a friction fit.

3. The method of claim 1, further comprising connecting the portable transdermal electrical stimulation (TES) applicator to a portable computing device worn or held by the subject via a cable.

4. The method of claim 1, further comprising allowing a user to adjust the delivered pulsed electrical stimulation.

5. The method of claim 1, further comprising adjusting the delivered pulsed electrical stimulation from a portable computing device coupled to the portable transdermal electrical stimulation (TES) applicator.

6. The method of claim 1, wherein activating the portable TES applicator comprises triggering activation of the portable TES applicator from a portable computing device held or worn by the subject.

7. The method of claim 1, wherein the pulsed electrical stimulation is an asymmetric, biphasic transdermal electrical stimulation.

8. A method of inducing or enhancing attention, alertness, and/or mental focus, the method comprising:
- placing a first electrode of a portable transdermal electrical stimulation (TES) applicator into a subject's first ear in contact with a first pinna and placing a second electrode of the portable TES applicator into the subject's second ear in contact with a second pinna, wherein the first and second electrodes include a conductive hydrogel that contacts the skin of the subject;
- activating the TES applicator to deliver pulsed electrical stimulation between the first and second electrodes with an intensity of 2 mA or greater, a duty cycle of greater than 50% and a frequency of between 200 Hz and 2 kHz; and
- modifying the subject's cognitive state to enhance attention, alertness, and/or mental focus without causing discomfort caused by the pulsed electrical stimulation by delivering the pulsed electrical stimulation between the first and second electrodes for 10 seconds or longer.

9. The method of claim 8, wherein the activating comprises delivering the pulsed electrical stimulation that is asymmetric, biphasic transdermal electrical stimulation having a frequency of 300 Hz or greater.

10. The method of claim 8, wherein the activating comprises delivering the pulsed electrical stimulation that is asymmetric, biphasic transdermal electrical stimulation having a frequency of 750 Hz or greater.

11. The method of claim 8, wherein the activating comprises activating the TES applicator to deliver a biphasic transdermal electrical stimulation.

12. A method of non-invasively stimulating the vagus nerve to induce or enhance attention, alertness, and/or mental focus, the method comprising:
- placing a first electrode of a portable transdermal electrical stimulation (TES) applicator into a subject's first ear in contact with a first pinna, and placing a second electrode of the portable TES applicator into the subject's second ear in contact with a second pinna, wherein the first and second electrodes include a conductive hydrogel that contacts the skin of the subject, wherein the first and second electrodes are held to the skin by mechanical means;
- stimulating the vagus nerve by activating the TES applicator to deliver pulsed electrical stimulation between the first and second electrodes at an intensity of 2 mA or greater, a duty cycle of greater than 50% and a frequency of between 200 Hz and 2 kHz; and
- delivering the pulsed electrical stimulation between the first and second electrodes for 10 seconds or longer to enhance attention, alertness, and/or mental focus without causing discomfort caused by the pulsed electrical stimulation.

13. The method of claim 12, wherein placing the first electrode comprises the subject wearing the first electrode on the first pinna in contact with a cymba of the subject's first ear.

14. The method of claim 12, further comprising varying the delivered pulsed electrical stimulation while the pulsed electrical stimulation is applied.

15. The method of claim 12, further comprising ramping the pulsed electrical stimulation during the delivery by decreasing one or more of the intensity, frequency, or duty cycle and then increasing one or more of the intensity, frequency, or duty cycle.

16. The method of claim 12, wherein the pulsed electrical stimulation is applied between the first and second electrodes for 15 minutes or longer.

17. The method of claim 12, wherein placing comprises placing the first and second electrodes so that the first and second electrodes are held in the subject's first and second ears, respectively, by a friction fit.

18. The method of claim 12, further comprising delivering an audible signal to the subject from the TES applicator.

19. The method of claim 18, wherein delivering audio output comprises delivering music.

* * * * *